(12) United States Patent
Licha et al.

(10) Patent No.: US 11,045,560 B2
(45) Date of Patent: Jun. 29, 2021

(54) THERAPEUTIC CONJUGATES WITH SULFATED DENDRIMERS FOR INTRACELLULAR TARGETING

(71) Applicant: IC DISCOVERY GMBH, Berlin (DE)

(72) Inventors: Kai Licha, Falkensee (DE); Michael Schirner, Berlin (DE)

( * ) Notice: Subject to any disclaimer, the term of this patent is extended or adjusted under 35 U.S.C. 154(b) by 0 days.

(21) Appl. No.: 15/313,084

(22) PCT Filed: May 21, 2015

(86) PCT No.: PCT/EP2015/061258
§ 371 (c)(1),
(2) Date: Nov. 21, 2016

(87) PCT Pub. No.: WO2015/177279
PCT Pub. Date: Nov. 26, 2015

(65) Prior Publication Data
US 2017/0182193 A1    Jun. 29, 2017

(30) Foreign Application Priority Data

May 21, 2014    (EP) .................................. 14169362

(51) Int. Cl.
*A61K 9/00* (2006.01)
*A61K 49/00* (2006.01)
(Continued)

(52) U.S. Cl.
CPC ........ *A61K 49/0054* (2013.01); *A61K 31/537* (2013.01); *A61K 31/553* (2013.01);
(Continued)

(58) Field of Classification Search
CPC .............................................. A61K 49/0054
See application file for complete search history.

(56) References Cited

FOREIGN PATENT DOCUMENTS

| EP | 2100621 A1 | 9/2009 |
| WO | 2010/000713 A1 | 1/2010 |

OTHER PUBLICATIONS

Friedler, A Peptide that binds and stabilizes p53 core domain: Chaperone strategy for rescue of oncogenic mutants, PNAS, 2002, 99(2), 937-942.*

(Continued)

*Primary Examiner* — Paul W Dickinson
(74) *Attorney, Agent, or Firm* — Prismatic Law Group, PLLC

(57) ABSTRACT

The present invention relates to novel dendrimer conjugates, methods for their preparation and their use for treatment of diseases. The invention discloses a new method for the delivery of dendrimer conjugates with therapeutically active molecules into the cell by utilizing transmembrane solute carrier proteins enabling uptake of the inventive dendrimer conjugates. Particular subject-matter of the present invention is a conjugate of the formula $E\text{-}[G\text{-}L\text{-}D(OSO_3^-M^+)_n]_m$, wherein E is a therapeutic or diagnostic effector molecule, wherein $D(OSO_3^-M^+)_n$ is a dendrimer D carrying a number n of sulfate groups $OSO_3^-M^+$, wherein the number n of sulfate groups is selected from 6 to 96, wherein M is a cationic inorganic or organic counter ion to the anionic sulfate group, wherein L is a linker or spacer between D and E, wherein G is a connecting functional group forming the attachment between L and E, and wherein m is an integer from 1 to 20.

25 Claims, 8 Drawing Sheets

Specification includes a Sequence Listing.

(51) Int. Cl.
*C08G 83/00* (2006.01)
*A61K 38/00* (2006.01)
*A61K 38/43* (2006.01)
*A61K 47/60* (2017.01)
*A61K 47/59* (2017.01)
*A61K 31/537* (2006.01)
*A61K 31/553* (2006.01)
*A61K 38/10* (2006.01)
*A61K 38/17* (2006.01)
*A61K 38/46* (2006.01)
*A61K 38/50* (2006.01)
*A61K 39/395* (2006.01)
*A61K 39/00* (2006.01)

(52) U.S. Cl.
CPC .............. *A61K 38/00* (2013.01); *A61K 38/10* (2013.01); *A61K 38/1767* (2013.01); *A61K 38/43* (2013.01); *A61K 38/465* (2013.01); *A61K 38/50* (2013.01); *A61K 39/395* (2013.01); *A61K 47/59* (2017.08); *A61K 47/60* (2017.08); *A61K 49/0021* (2013.01); *A61K 49/0032* (2013.01); *A61K 49/0041* (2013.01); *A61K 49/0043* (2013.01); *A61K 49/0056* (2013.01); *C08G 83/004* (2013.01); *A61K 2039/505* (2013.01); *C12Y 301/21001* (2013.01); *C12Y 305/01001* (2013.01)

(56) References Cited

OTHER PUBLICATIONS

Albert, Noxa and cancer therapy, Molecular and Cellular Oncology 1, 2014, e29906, 1-7.*
Licha et al., "Fluorescence Imaging with Multifunctional Polyglycerol Sulfates: Novel Polymeric near-IR Probes Targeting Inflammation", Bioconjugate Chemistry, vol. 22, No. 12, Dec. 21, 2011 (Dec. 21, 2011), pp. 2453-2460, XP055204924, ISSN: 1043-1802, DOI: 10.1021/bc2002727.
Szent-Gyorgyi et al., "Fluorogenic Dendrons with Multiple Donor Chromophores as Bright Genetically Targeted and Activated Probes", Journal of the American Chemical Society, vol. 132, No. 32, Aug. 18, 2010 (Aug. 18, 2010), pp. 11103-11109, XP055204989, ISSN: 0002-7863, DOI: 10.1021/ja9099328.
International Search Report dated Aug. 6, 2015 in PCT/EP2015/061258 (3 pages).

* cited by examiner

B

A

A

SEQUENCE LISTING

```
<160> NUMBER OF SEQ ID NOS: 7

<210> SEQ ID NO 1
<211> LENGTH: 22
<212> TYPE: PRT
<213> ORGANISM: Artificial Sequence
<220> FEATURE:
<223> OTHER INFORMATION: BIM

<400> SEQUENCE: 1

Cys Gly Met Arg Pro Glu Ile Trp Ile Ala Gln Glu Leu Arg Arg Ile
1               5                   10                  15

Gly Asp Glu Phe Asn Ala
            20

<210> SEQ ID NO 2
<211> LENGTH: 19
<212> TYPE: PRT
<213> ORGANISM: Artificial Sequence
<220> FEATURE:
<223> OTHER INFORMATION: BIM
```

```
<400> SEQUENCE: 2

Cys Gly Asp Met Arg Pro Glu Ile Tyr Ile Gln Glu Leu Arg Arg Ile
1               5                   10                  15

Gly Asp Tyr

<210> SEQ ID NO 3
<211> LENGTH: 26
<212> TYPE: PRT
<213> ORGANISM: Artificial Sequence
<220> FEATURE:
<223> OTHER INFORMATION: Bcl9

<400> SEQUENCE: 3

Cys Gly Leu Ser Gln Glu Gln Leu Glu His Arg Glu Arg Ser Leu Gln
1               5                   10                  15

Thr Leu Arg Asp Ile Gln Arg Met Leu Phe
            20                  25

<210> SEQ ID NO 4
<211> LENGTH: 25
<212> TYPE: PRT
<213> ORGANISM: Artificial Sequence
<220> FEATURE:
<223> OTHER INFORMATION: Bcl9/2

<400> SEQUENCE: 4

Cys Gly Leu Ser Lys Glu Gln Leu Glu His Arg Glu Arg Ser Leu Gln
1               5                   10                  15

Thr Leu Arg Asp Ile Glu Arg Leu Leu
            20                  25

<210> SEQ ID NO 5
<211> LENGTH: 27
<212> TYPE: PRT
<213> ORGANISM: Artificial Sequence
<220> FEATURE:
<223> OTHER INFORMATION: PUMA

<400> SEQUENCE: 5

Cys Gly Glu Glu Gln Trp Ala Arg Glu Ile Gly Ala Gln Leu Arg Arg
1               5                   10                  15

Met Ala Asp Asp Leu Asn Ala Gln Tyr Glu Arg
            20                  25

<210> SEQ ID NO 6
<211> LENGTH: 24
<212> TYPE: PRT
<213> ORGANISM: Artificial Sequence
<220> FEATURE:
<223> OTHER INFORMATION: BID

<400> SEQUENCE: 6

Cys Gly Glu Asp Ile Ile Arg Asn Ile Ala Arg His Ala Ala Gln Val
1               5                   10                  15

Gly Ala Ser Ala Asp Arg Ser Ile
            20

<210> SEQ ID NO 7
<211> LENGTH: 24
<212> TYPE: PRT
<213> ORGANISM: Artificial Sequence
<220> FEATURE:
<223> OTHER INFORMATION: c-myc
```

```
<400> SEQUENCE: 7

Cys Pro Lys Val Val Ile Leu Lys Lys Ala Thr Ala Tyr Ile Leu Ser
1               5                   10                  15

Val Gln Ala Glu Glu Gln Lys Leu
            20
```

THERAPEUTIC CONJUGATES WITH SULFATED DENDRIMERS FOR INTRACELLULAR TARGETING

INCORPORATION OF SEQUENCE LISTING

This application contains a sequence listing submitted electronically via EFS-web, which serves as both the paper copy and the computer readable form (CRF) and consists of a file entitled "15-313084_seqlist_of_3-26-21.txt", which was created on Mar. 25, 2021, which is 2,503 bytes in size, and which is herein incorporated by reference in its entirety.

FIELD OF THE INVENTION

The present invention relates to novel dendrimer conjugates, methods for their preparation and their use for treatment of diseases. The invention discloses a new method for the delivery of dendrimer conjugates with therapeutically active molecules into the cell by utilizing transport proteins enabling uptake of the inventive dendrimer conjugates and interaction of these therapeutically active molecules with molecules relevant for disease directly within the cell.

BACKGROUND

During the last decades much progress has been made to improve the efficacy of diagnostic and therapeutic drugs. Several strategies were followed during the last decades to avoid severe unwanted drug effects on healthy tissues and organs. Predominantly, drug research was focused on new drug targets that promised a disease-specific expression of the target mechanism. With respect to the discovery of signal transduction mechanisms in proliferating and activated cells, numerous new targets have been identified. However, with few exceptions therapeutic attack of the majority of newly discovered drug targets remained less effective, since the therapeutic molecule has to possess the physicochemical properties to penetrate tissues, membrane barriers and cells to reach the target, in particular when the target is expressed inside of cells. Thus, much effort has been devoted to improve the bioavailability of clinically established therapeutic drugs. In order to improve bioavailability drug research focused on the chemical modification or pharmaceutical formulations of the therapeutic molecules. The majority of therapeutic drug molecules does not reach the site of the disease and are only applied into the human body in order to achieve necessary drug concentration in the blood, thereby not having a certain degree of selectivity for diseased tissues. Therefore, the utmost portion of the applied drug is eliminated from blood circulation without reaching the site of the disease.

Many therapeutic molecules based on proteins and peptides are used as highly specific and effective therapeutic agents. Their use is, however, complicated by their physicochemical properties, which is due to the inherently polar nature of the amino acid composition and polypeptide backbone of polar amide connections. In particular, their molecular size and charge of the proteins hamper bioavailability at the desired target. The application of therapeutic proteins is further complicated by the circumstance that many protein and peptide drugs have their therapeutic targets inside cells. Here, the major challenge to be addressed in order to find new drugs or drug delivery technologies is the permeation of the cell membrane to bring these types of drugs into the cytoplasm or nucleus of the target cells. It is well known that single molecules with a molecular weight greater than 1 kDa do not enter the cytoplasm, directly.

Many diagnostic molecules, such as fluorescent dyes, contrast agents for Magnetic resonance imaging, CT, and radiochelates for nuclear imaging, are of hydrophilic nature and are not capable to enter the cell, similarly to the above described properties of polypeptides (van der Molen A J, Eur. J. Radiol, 2008, 66, 168). Thus, there is no general pathway available, which permits to select a diagnostic agent for the purpose to characterize intracellular pathways of disease and detect the interaction of therapeutic molecules with intracellular molecules.

Traditional methods of intracellular delivery are electroporation or microinjection of proteins. Here, the intactness of the cell membrane is disturbed for a short period of time enabling the intracellular delivery of macromolecules with a size of greater 1 kDa. However, the method is invasive and only applicable for in vitro experiments, but not for clinical conditions. Another disadvantage is the low efficacy of the procedure which can be measured by the number of tumour cells loaded with the target protein. Electroporation or microinjection usually leads to intracellular delivery in about 20-40% of the treated cells but the reproducibility is very low.

Most recently, novel pharmaceutical approaches have been established in order to deliver therapeutic polypeptides, proteins and antibodies into tumour cells. Pharmaceutical nanocarriers, such as liposomes, self-assembly micellar systems, or polymeric nanoparticles can be used for intracellular delivery of therapeutic proteins (Du et al., Curr Drug Metab, 2012, 13, 82-92). They are able to escape endosomal metabolism but lack specificity to the tumour cell. In this regard, targeting ligands can be used to direct such nanocarriers towards tumour cells. However, liposomal and other nanoparticular formulations carrying therapeutic polypeptides, antibodies, and proteins in combination with targeting ligands (van der Meel et al., Adv Drug Deliv Rev. 2013, 65, 1284-98) are costly and considered as complex chemical entities. The optimization of these entities is often complicated due to the fact that the interaction between carrier material and therapeutic payload has to be carefully adapted. With respect to diagnostic payloads, the physicochemical properties of the diagnostic agent has to be carefully adapted to the carrier in a similar way to receive functional chemical entities.

Albeit the opportunities of pharmaceutical combination with nanoparticular carrier systems, the use of proteins and peptides as therapeutic agents is hampered per se by the whole set of their intrinsic properties associated with their nature as complex macromolecules, which are, as a rule, foreign to the recipient organism. This leads to low stability of the majority of peptide and especially protein drugs at physiological pH values and temperatures, particularly when these proteins have to be active in the environment different from their normal one. Different processes leading to the inactivation of various biologically active proteins and peptides in vivo include conformational protein transformation into inactive form due to the effect of temperature, pH, high salt concentration or detergents. Very often, aggregation of proteins leads to loss of function and metabolism, which is difficult to exactly determine in pharmaceutical nanocarrier systems.

Solution to the Problem Underlying the Present Invention

The inventors of the present application have surprisingly found a methodology of delivering therapeutic molecules, particularly polypeptides, specifically into cells of disease. The solution to the problem is based on a surprising finding that such polypeptides and proteins can be delivered into tumour cells without a pharmaceutical formulation based on nanoparticles, polymers, micelles or liposomes. Instead, it was found that a group of compounds based on defined dendrimers covalently linked to the therapeutic effector is capable of being transported as dendrimer conjugate into the target cell. In particular, it was found that the type of dendrimer carrying a defined plurality of sulfate groups ($-OSO_3^-M^+$) can act as active transporter moiety, when this dendrimer is covalently connected to the respective therapeutic polypeptide or other type of effector, including therapeutic and diagnostic molecules.

Subject-matter of the present invention is the provision of dendrimer conjugates, methods for their preparation and their use for treatment and diagnosis of diseases.

Therapeutic and diagnostic molecules that are impermeable to cells are hampered from being taken up into normal cells and are directed only to those cells which have uptake mechanisms based on transmembrane solute carriers, thereby improving selectivity and decreasing toxicity to the organism. Surprisingly and unexpectedly, by the present invention, dendrimer conjugates are provided that enable transmembrane delivery of therapeutically active molecules via transport proteins. It was found that therapeutically active molecules as well as diagnostic molecules that are as single compounds alone not capable of being taken up into cells due to the properties described above, are surprisingly applicable for being transported into cells and exhibiting a therapeutic or diagnostic effect directly within the cell. Moreover, specific targeting to the cells in the organism is enabled by the dendrimer conjugates of the invention. In this context, the defined dendrimer conjugates enable the improvement of the bioavailability and selectivity of a broad spectrum of therapeutic and diagnostic effector molecules, including polypeptides as well as small molecule therapeutics. Therapeutic and diagnostic molecules that are not capable of entering cells are transported into cells utilizing transport proteins. Surprisingly and unexpectedly, this could be achieved by the homogeneity of the molecular weight of each dendrimer within the claimed conjugates, in combination with the covalent conjugation between the effector molecules and sulfated dendrimers.

A pharmaceutical formulation with the therapeutic molecule physically embedded or encapsulated in a carrier particle or polymer (without covalent bonding to the carrier) has shown the disadvantage that the therapeutic effector molecules can redistribute in the organism by carrier decomposition and/or leakage from the carrier, thereby exhibiting its parent toxicity to the organism. Accordingly, diagnostic molecules can redistribute and thereby generating signals which make the examiner detect the wrong molecular situation not connected with the uptake mechanism.

DETAILED DESCRIPTION OF THE INVENTION

The described features of the invention are substantiated by the following descriptions of exemplary embodiments which are presented in order to support the invention and are not intended to be limiting thereof.

Subject-matter of the present invention is a conjugate of the formula

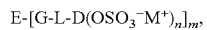

wherein E is a therapeutic or diagnostic effector molecule, wherein $D(OSO_3^-M^+)_n$ is a dendrimer D carrying a number n of sulfate groups $OSO_3^-M^+$, wherein the number n of sulfate groups is selected from 6 to 96, wherein M is a cationic inorganic or organic counter ion to the anionic sulfate group, wherein L is a linker or spacer between D and E, wherein G is a connecting functional group forming the attachment between L and E, and wherein m is an integer from 1 to 20.

In a preferred embodiment, subject-matter of the present invention is a conjugate comprising a polysulfated dendrimer D and a therapeutic or diagnostic effector molecule E that is covalently conjugated to said polysulfated dendrimer.

In a more preferred embodiment, the subject-matter of the present invention is a conjugate of the formula E-[G-L-D$(OSO_3^-M^+)_n]_m$, wherein each of the dendrimers D of said conjugate has the same molecular weight. Within the embodiment, the dendrimer structures have a defined and unique molecular weight. The means the resulting conjugate is not composed of many different dendritic molecules each having another structure, branching, size, charge, volume or polarity, which is the result of a polymeric nature. In WO2011/095311, the use of conjugates of therapeutic proteins with sulfated polyols is described, wherein these sulfated polyols are of polymeric nature with a non-defined molecular weight. They are characterized by an average molecular weight based on polydispersity, with statistical conjugation with therapeutic molecules. It was surprisingly found that a defined dendrimer system (24, 32 or 48 sulfate groups) with defined linker conjugated to a toxin protein leads to higher efficacy in treating tumor cells in cell culture when compared to a polydisperse polyglycerolsulfate of comparable average molecular weight (see Example 19).

Suprisingly and unexpectedly, another advantage of using defined dendrimer systems of single molecular weight in comparison to polymeric sulfated polyglycerol could be identified by the present invention. After labeling with a fluorescent dye (ICC), yielding for example compounds of Example 8 (ICC-d01, ICC-d12, ICC-d18), cellular uptake studies were conducted in comparison to polymeric ICC-polyglycerolsulfate (average molecular weight 12000 Da). ICC-d01, ICC-d12, ICC-d18 resulted in an intracellular distribution in the cytosol, whereas polymeric ICC-polyglycerolsulfate showed substantial localization additionally in endosomal compartments, probably due to partial endocytotic uptake of the polymeric mixture. Endocytotic uptake for polymers becomes predominant above 20 kDa, as also described in WO2011/095311 for sulfated polymers. In general, uptake of therapeutic proteins by the endosomal compartment needs to be circumvented for major reasons. First, the endosomal membrane represents a barrier for the translocation of therapeutic effector molecules towards the cytosol. Usually, therapeutic effector molecules become not available at the therapeutic target molecules in the cytosol. Second, many metabolizing and catalytic enzymes may destroy the therapeutic effector molecules before they can be translocated to the cytosol. This aspect is of particular importance for protein therapeutic effector molecules. The synthesis of polyglycerolsulfates involving anionic ring-opening polymerization to synthesize the polyglycerol backbone is published state-of-the-art usually leading to a certain molecular weight distribution around an average molecular weight $M_n$ with a polydispersity index of 15-1.8 (Gröger et al., Bioconjug. Chem. 2013, 24, 1507-14). Thus, for an average molecular weight $M_n$ within 5-10 kDa with a polydispersity index of 1.5-1.8 has always a substantial amount of higher molecular weight structures (>20 kDa) in the mixture which are difficult to quantify. Accordingly, in Example 18, a clear independency from endocytosis is apparent only for protein conjugates with sulfated dendrimers (Asp-d02) and not for conjugates with polyglycerolsulfate.

Furthermore, a person skilled in the art is aware of the methods to prove that each dendrimer has the same molecular weight, e.g. 1H-NMR spectroscopy, 13C-NMR spectroscopy, elementary analysis, mass spectroscopy that are classical techniques of organic chemistry.

In a specific embodiment, subject-matter of the present invention is a conjugate of the formula E-[G-L-D(OSO$_3^-$M$^+$)$_n$]$_m$, wherein the number n of sulfate groups is the same for each dendrimer D. Therefore, each dendrimer of said conjugate can only encompass one selected number n of sulfate groups, for example only 6 or only 8 or only 12 or only 16 sulfate groups, whereby the number n of sulfate groups is selected from 6 to 96.

Further subject-matter of the present invention is a conjugate, wherein the sulfate groups OSO$_3^-$M$^+$ are preferably derived from hydroxyl groups which are converted into sulfate groups (monoesters of sulfonic acid) by a sulfation process.

Preferred agents to conduct a sulfation process of hydroxyl groups are complexes of sulfurtrioxide (such as SO$_3$-pyridine complex, SO$_3$-triethylamine complex, SO$_3$-trimethylamine complex, SO$_3$-DMF complex) or sulfamic acid (Mol J A et al., Carbohydr Res. 2003 338:1397-401).

In another embodiment, subject-matter of the present invention is a conjugate, wherein the repeating units of monomers to build the dendritic structure are selected from the group comprising 1,2-substituted glycerol, 1,3-substituted glycerol, pentaerythritol, glucose, mannose, galactose, lysine, tris(hydroxymethyl)aminomethane, tris(propionic acid)aminomethane, 1,1'-bis(hydroxymethyl)-propionic acid, succinic acid, glutaric acid, maleic acid, glycolic acid, diglycolic acid, adipic acid, lactic acid, citric acid, propionic acid (2-aminoethyl)amide, propyleneimine, ethyleneimine, propyleneoxide, ethyleneoxide.

In another specific embodiment, subject-matter of the present invention is a conjugate, wherein the connection of monomers in the dendrimer is based on functional groups selected from ether, thioether, carboxylic ester, sulfonylester, sulfonamide, carboxylamide, amine, carbamate, thiocarbamate, urea, thiourea, hydrazone, imine, disulfide, phosphate, phosphonate, triazole, acetal, ketal.

In another embodiment, subject-matter of the present invention is a conjugate of the formula E-[G-L-D(OSO$_3^-$M$^+$)$_n$]$_m$ wherein the dendrimer D contains a central dendrimer core unit (CDCU) with the covalent attachment of a linker unit. The CDCU comprise structures selected from pentaerythritol, glycerol, triglycerol, glycerolamine, tris(propionic acid)methyl, tris(hydroxymethyl)methyl, tetraoxaspiro(5.5)undecane, adamantyl.

Preferred are structures, wherein central dendrimer core units (CDCU) with the covalent attachment of a linker unit comprise structures such as pentaerythritol, glycerol, triglycerol, glycerolamine, tris(propionic acid)methyl and structures as depicted below.

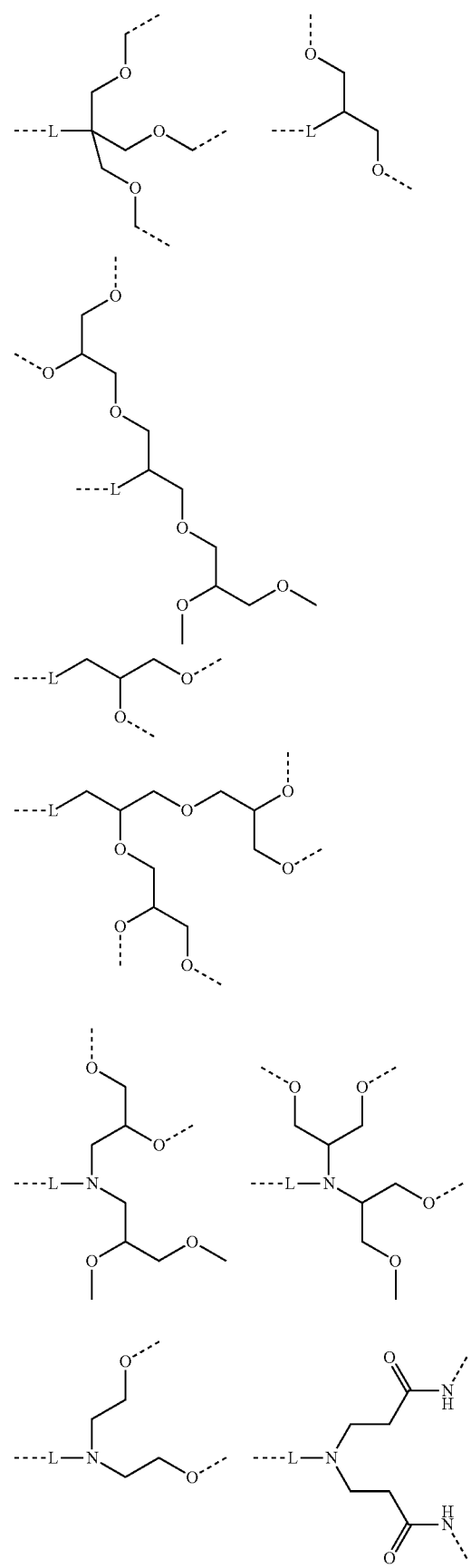

-continued
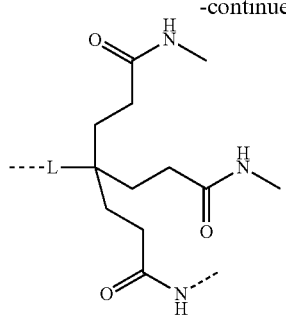
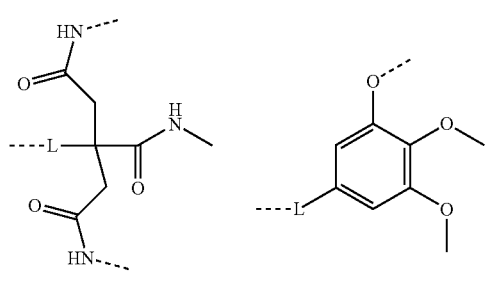
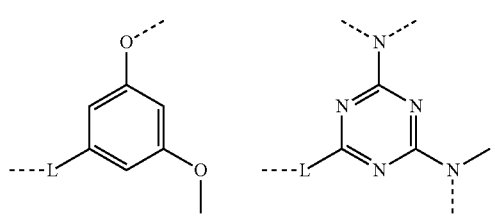
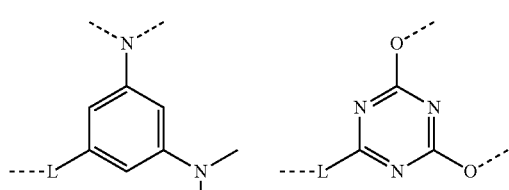
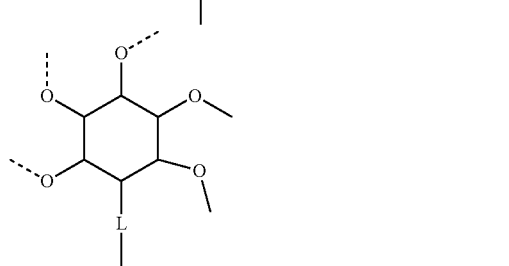
-continued
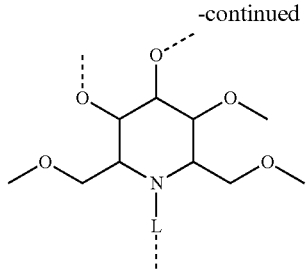
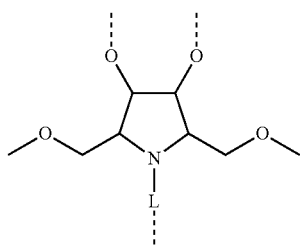
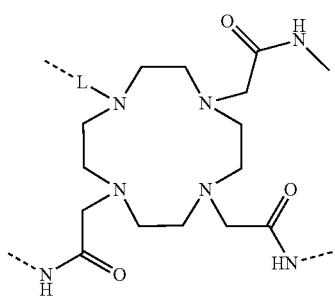
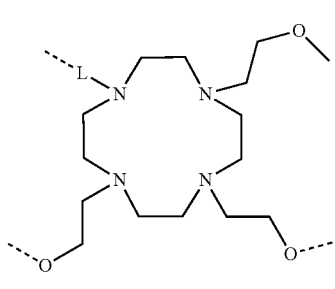
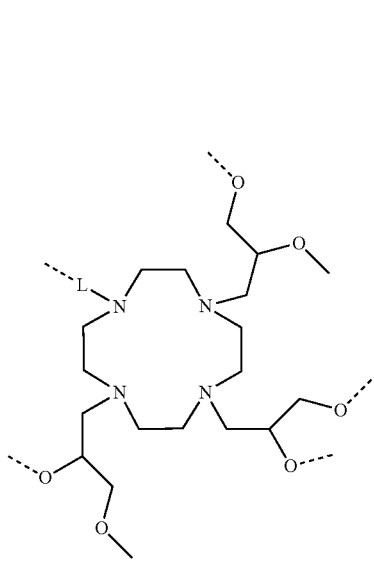

Subject-matter in another specific embodiment of the present invention is a conjugate, wherein D contains terminal groups selected from 1,2-disulfatoalkyl, 1,3-disulfatoalkyl, N,N'-di(1-sulfatoalkyl)amine, tris(sulfatomethyl)methyl, 1,2,4-trisulfato-3-alkyl, 1,2,3,4,5-pentasulfatoalkyl derived from glucosamine.

To achieve a high density of sulfate groups, their position at alkyl moieties has to be such that they are in close proximity to each other. This can be achieved by structural motifs of 1,2-disulfatoalkyl, 1,3-disulfatoalkyl, N,N'-di(1-sulfatoethyl)amine. There are different structures possible which comprise 1,2-disulfato- or 1,3-disulfato structural motifs. Under such structures fall also sugar or glycan moieties which, after sulfation, comprise also the 1,2-disulfato- or 1,3-disulfato units within the structure. Mono-, di- or oligoglycane moieties are possible, and within these structures, cyclic or open chain (reduced) structures are possible. Scope of the invention includes 1,2,3,4,5-pentahydroxyhexyl structures derived from hexose (glucose, galactose, mannose) sugars, such as glucosamine or glucamine. D-glucamine can be used in dendrimer systems leading to 5 sulfate groups per glutamine residue. Another scope includes cyclodextrins (α, β or γ-cyclodextrins), which are monofunctionalized (such as 6-deoxy-6-azido-cyclodextrins or other functional groups known to the skilled person; Roux M et al., Eur Biophys J. 2007, 36, 861-7) to connect the linker L, and can be modified at each hydroxyl group with glycerol followed by sulfation.

Thus, in a preferred embodiment subject-matter of the present invention are dendrimers D with a terminal 1,2,3,4,5-pentasulfato unit, which is derived from sugars, preferably glucosamine, dendrimers D with terminal 1,2-disulfato unit, which is derived from smaller hydroxylated units comprising glycerol structures, dendrimers D with terminal 1,3-disulfato units derived from bis-(hydroxymethyl)alkyl moieties. More preferred as structural entity in D is the 1,2-disulfatoalkyl structure based on a terminal 1-substituted 1,2-disulfatopropyl which is derived from a glycerol unit.

Within the context of this embodiment, 1,2-substituted glycerol means that two adjacent hydroxyl groups are forming a connection to the subsequent monomer unit of the next generation shell in the dendrimers structure. 1,3-substituted glycerol means that the two outer hydroxyl group form this connection.

In a preferred embodiment, subject-matter of the present invention is a conjugate, wherein D contains sulfate groups, wherein sulfate groups are particularly preferred over sulfonate and carboxylate groups which are known to be used in dendritic polymers and dendrimers (Weinhart et al., Biomacromolecules. 2011, 12, 2502). As published, sulfonate and carboxylate groups can be introduced into dendrimer molecules by modifying hydroxyl or amino groups with e.g. succinyl anhydride, bromoacetic acid, 1,3-propanesultone, 1,4-butansultone. Surprisingly, sulfate dendrimers exhibit more efficient cellular uptake (detected with fluorescently labeled conjugates) also for smaller molecular weights (number of anionic group <24) compared to carboxylate and sulfonate groups.

In a more specific embodiment, the subject-matter of the present invention is a conjugate, wherein the linker unit L is covalently attached to dendrimer D.

In another very specific embodiment, the subject-matter of the present invention is a conjugate, wherein the linker unit L is covalently bound to the focal point of the dendrimer D at a position, whereby from this focal point, the dendrimer is grown to reach its dendritic structure.

Further subject-matter of the present invention is a conjugate of the formula $E\text{-}[G\text{-}L\text{-}D(OSO_3^-M^+)_n]_m$, wherein L is a $C_{4\text{-}100}$-alkyl group.

In one embodiment, subject-matter of the present invention is a conjugate of the formula $E\text{-}[G\text{-}L\text{-}D(OSO_3^-M^+)_n]_m$, wherein L is a $C_{4\text{-}100}$-alkyl group, wherein the $C_{4\text{-}100}$-alkyl group is selected from the group consisting of aliphatic cyclic, branched or linear units in which one or more methylene groups may independently be replaced by a unit selected from the group consisting of O, S, NH, NH—O, C(=O)NH, OC(=O)NH, OC(=O)O, NHC(=O)NH, NHC(=S)NH, C(=NH)NH, C(=O), S(=O)$_2$, S(=O), S(=O)$_2$O, S—S, CH=N, CH=N—NH, C=N—NHC(=O), OP(=O)(O$^-$M$^+$)O, P(=O)(O$^-$M$^+$)O, arylene, ethenylene or ethinylene, and triazolylene, in which any hydrogen atom may independently be replaced by methyl, ethyl or hydroxymethyl.

Further subject-matter of the present invention is a conjugate of the formula $E\text{-}[G\text{-}L\text{-}D(OSO_3^-M^+)_n]_m$, wherein the structure of L is

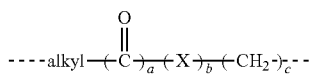

wherein alkyl is a $C_{4\text{-}100}$-alkyl group in which one or more methylene groups may be replaced by a group selected from the group consisting of aliphatic cyclic, branched or linear units in which one or more methylene groups may independently be replaced by a unit selected from the group consisting of O, S, NH, NH—O, C(=O)NH, OC(=O)NH, OC(=O)O, NHC(=O)NH, NHC(=O)NH, C(=O), S(=O)$_2$, S(=O), S(=O)$_2$O, S—S, CH=N, CH=N—NH, C=N—NHC(=), OP(=O)(O$^-$M$^+$)O, P(=O)(O$^-$M$^+$)O, arylene, ethenylene or ethinylene, and triazolylene, in which any hydrogen atom may independently be replaced by methyl, ethyl or hydroxymethyl, X is NH, S or O, and a, b and c can be independently 0 or 1 (a+b+c=0 excluded).

In a preferred embodiment, subject-matter of the present invention is a conjugate of the formula $E\text{-}[G\text{-}L\text{-}D(OSO_3^- M^+)_n]_m$, wherein L is a $C_{4-50}$-alkyl group in which one to ten, methylene groups are be replaced by a group selected from the group comprising O, C(=O)NH, OC(=O)NH, OC(=O)O, NHC(=O)NH, NHC(=S)NH, triazole, wherein X is NH or O, and a, b and c can be independently 0 or 1 (a+b+c=0 excluded).

In a more preferred embodiment, subject-matter of the present invention is a conjugate of the formula $E\text{-}[G\text{-}L\text{-}D(OSO_3^-M^+)_n]_m$, wherein L is alkyl including a $C_4$ to $C_{18}$ carbon chain, a unit C(=O)NH and a short PEG chain up to 10 repeating units of $CH_2CH_2O$, to which a connecting group G is placed at the end of this chain as a reactive group for covalent conjugation to E.

In a specific embodiment, subject-matter of the present invention is a conjugate of the formula $E\text{-}[G\text{-}L\text{-}D(OSO_3^- M^{30})_n]_m$, wherein L comprises structures which are cleavable under intracellular conditions, wherein the cleavable structures are selected from the group of disulfide (S—S), acid-cleavable structures CH=N, CH=N—NH, CH=N—NHC(=O), C=N—O, in which any nitrogen or carbon atom may be substituted with ethyl or methyl. Another structure which is cleavable under intracellular conditions comprises amino acid sequences of 2 to 10 amino acids.

In a more specific embodiment, subject-matter of the present invention is a conjugate of the formula $E\text{-}[G\text{-}L\text{-}D(OSO_3^-M^+)_n]_m$, wherein L comprises structures which exhibit an optical absorption peak in the UV to VIS spectral range within 280 and 650 nm, preferably between 300 and 550 nm.

In an even more specific embodiment, subject-matter of the present invention is a conjugate of the formula $E\text{-}[G\text{-}L\text{-}D(OSO_3^-M^+)_n]_m$, wherein L comprises structures employing at least two aromatic or bisaromatic moieties, such as biphenyl, naphthyl, dibenzoketone, dansyl, pyrene, perylene, coumarin, 4,4-difluoro-4-bora-3a,4a-diaza-s-indacene, or cyanine dye, preferably indocarbocyanine or monomethine chromophore moieties. The spectroscopic quantification allows the determination of dendrimer-to-protein/polypeptide ratios. Examples of UV to VIS detectable structures of L connected to D are described in Example 9 and 10.

Further subject-matter of the present invention is a conjugate of the formula $E\text{-}[G\text{-}L\text{-}D(OSO_3^-M^+)_n]_m$, wherein E is a therapeutic or diagnostic effector molecule.

The use of a sulfated dendrimer covalently conjugated with a fluorescent dye is described by Paulus et al. (Macromol. Biosci. 2014, 14, 643-654). The [G4.0]-dendrimer is derived from a polyol of 64 hydroxy groups, to which statistically a linker is conjugated, followed by sulfation and labelling with a dye. This design yields a non-perfect structure, as the linker moiety cannot be placed exactly in a 1:1 ratio at a desired position. The publication shows uptake of these and polymeric polysulfate of lesser branching degree into tumor cells and teaches optimal uptake with a moderate branching degree of 60% (a non-perfect dendrimer structure). There is no information on the mechanism of uptake and whether a transporter-mediated pathway can be utilized to transport therapeutically active molecules in order to make them available for an intracellular interaction with molecular mechanisms of disease.

In a specific embodiment, subject-matter of the present invention is a conjugate of the formula $E\text{-}[G\text{-}L\text{-}D(OSO_3^- M^+)_n]_m$, wherein E is a therapeutic effector molecule.

In another embodiment, subject-matter of the invention is a conjugate, wherein the effector molecule comprises substances which may interfere with intracellular mechanisms of proliferation, apoptosis, synthesis of connective tissue material (e.g. collagen, fibronectin), immune function, senescence, or immune defence.

More specifically, the interference with intracellular mechanisms of disease comprises a conjugate of sulfated dendrimers and therapeutic molecules for the use in treatment of cells by transporting the conjugate into the cell and thereby localizing the therapeutic effector molecule E within the cell, where this molecule E interacts directly with molecular mechanisms of disease. This interaction is based on a direct binding to molecules within the cell thereby inducing disturbance of or changes within biological signal pathways. The binding is defined the binding strength or binding affinity which depends on the molecular nature and structure of the therapeutic effector molecule (as further substantiated in sections below).

In a more preferred embodiment, subject-matter of the present invention is a conjugate of sulfated dendrimers and therapeutic molecules for the use in treatment of cells which have uptake mechanisms based on transport proteins from the group of transmembrane solute carriers, that enable transmembrane delivery of therapeutically active molecules via transmembrane solute carriers into cells. These transmembrane solute carriers comprise preferably organic anion transporter proteins (OATPs; Liu. T et al., J. Drug Target. 2014, 22, 14-22). A preferred embodiment are OATPs with tumor-specific expression, including OATP1B1, OATP1B3 or NTCP (Buxhofer-Ausch et al., J Drug Deliv. 2013, 863539).

In a more preferred embodiment, subject-matter of the present invention is a conjugate of sulfated dendrimers and therapeutic molecules for the use in treatment and diagnosis of cancer, wherein said conjugates of sulfated dendrimers and therapeutic molecules are directed against molecular targets in cancer cells. Cancer cell types comprise preferably high expression of OATP1B1, OATP1B3 or NTCP, for the treatment of cancer such as pancreatic cancer, lung cancer, CNS cancer, melanoma, colon cancer, skin cancer, breast cancer, renal cancer, hepatic cancer. Another preferred embodiment is treatment of cancer stem cells which often express high levels of OATP1B1, OATP1B3 or NTCP.

Thus, subject-matter of the present invention is a conjugate of sulfated dendrimers and therapeutic molecules for the use in treatment and diagnosis of disease, wherein said conjugates of sulfated dendrimers and therapeutic molecules are taken up into cells by transporter proteins and interact inside the cell with molecular mechanisms of disease.

Even more preferred is a conjugate of sulfated dendrimers and therapeutic molecules for the use in treatment of cells which have uptake mechanisms based on transport proteins from the group of transmembrane solute carriers and that are otherwise not capable of taking up said therapeutic molecules (see also example 18). Surprisingly, therapeutic effector molecules can be accumulated or enriched within the target cell based on the mechanism of uptake of the conjugates by transporter proteins what has not been possible before as these therapeutic molecules are not capable to reach the target molecule to which it exhibits a binding affinity.

Thus, subject-matter of the present invention is a conjugate of sulfated dendrimers and therapeutic molecules for the use in treatment and diagnosis of disease, wherein said conjugates of sulfated dendrimers and therapeutic molecules are taken up into cells by transporter proteins, interact inside the cell with molecular mechanisms of disease, and accumulate in the cell due to a binding affinity of the therapeutic effector molecule to an intracellular target molecule. Intracellular targets are further substantiated below.

In another specific embodiment, subject-matter of the present invention is a conjugate, wherein the effector molecules are selected from the group comprising small molecules, peptides, proteins, glycans, nucleic acids. Preferred are effector molecules of these classes which are not taken up into cells on its own.

In another very specific embodiment, subject-matter of the present invention is a conjugate, wherein the small molecule is selected from the group comprising peptide or peptidomimetic structures, including cyclic or open-chain peptides with natural or non-natural structural modifications. It was surprisingly shown that hydrophilic peptides with no uptake into cells can by localized within tumor cells after conjugation to dendrimers of the present invention.

In another very specific embodiment, subject-matter of the present invention is a conjugate, wherein the proteins are selected from the group comprising globular proteins, glycoproteins, toxins, enzymes, antibodies, antibody fragments, engineered antibody and protein constructs, including single domain antibodies (sdAb), single chain Fv antibodies (scFv), single chain-Fv-Fc antibodies (scFv-Fc).

In another very specific embodiment, subject-matter of the present invention is a conjugate, wherein the proteins are selected from the group comprising antibody mimetics that, like antibodies, can specifically bind antigens, but that are not structurally related to antibodies. Particularly preferred are antibody mimetics selected from the group of affibodies, affilins, avimers, antikallins, Darpins, kunitz domains, fynobodies, polypeptides generated from the type III domain of fibronectin.

In another very specific embodiment, subject-matter of the present invention is a conjugate, wherein the nucleic acids include RNA, DNA, siRNA, mRNA, antisense-RNA, microRNA or engineered formats, such as aptamers.

In another specific embodiment, subject-matter of the present invention is a conjugate, wherein E is directed against molecules involved in proliferation and apoptosis of tumor cells. More specifically, these molecules are localized within the tumor cell, preferably within the cytosol of tumor cells.

In another very specific embodiment, subject-matter of the present invention is a conjugate, wherein E is selected from the group comprising polypeptides or small molecular effector molecules that bind targets such as Fox01, HDAC, DP-1, E2F, ABL, AMPK, BRK, BRSK1, BRSK2, BTK, CAMKK1, CAMKK alpha, CAMKK beta, Rb, Suv39H1, SCF, p19INK4D, GSK-3, p18 INK4, myc, cyclin E, CDK2, CDK9, CDG4/6, Cycline D, p16 INK4A, cdc25A, BMI1, SCF, Akt, CHK1/2, CK1 delta, CK1 gamma, CK2, CLK2, CSK, DDR2, DYRK1A/2/3, EF2K, EPH-A2/A4/B1/B2/B3/B4, EIF2AK3, Smad2, Smad3, Smad4, Smad7, p53, p21 Cip1, PAX, Fyn, CAS, C3G, SOS, Tal, Raptor, RACK-1, CRK, Rap1, Rac, KRas, NRas, HRas, GRB2, FAK, PI3K, spred, Spry, mTOR, MPK, LKB1, PAK1/2/4/5/6, PDGFRA, PYK2, Src, SRPK1, PLC, PKC, c-Raf, PKA, PKB alpha/beta, PKC alpha/gamma/zeta, PKD, PLK1, PRAK, PRK2, RIPK2, B-Raf, WAVE-2, TSC2, DAPK1, BAD, IMP, C-TAK1, TAK1, TAO1, TBK1, TESK1, TGFBR1, TIE2, TLK1, TrkA, TSSK1, TTBK1/2, TTK, Tpl2/cot1, MEK1, MEK2, PLD1, Erk1 Erk2, Erk5, Erk8, p90RSK, PEA-15, SRF, p27 KIP1, TIF1a, HMGN1, ER81, MKP-3, c-Fos, FGF-R1, GCK, GSK3 beta, HER4, HIPK1/2/3/, IGF-1R, cdc25, UBF, LAMTOR2, Stat1, Stat3, CREB, JAK, Src, PTEN, NF-kappaB, HECTH9, Bax, HSP70, HSP90, Apaf-1, Cyto c, BCL-2, Bcl-xL, Smac, XIAP, Caspase-9, Caspase-3, Caspase-6, Caspase-7, CDC37, TAB, IKK, TRADD, TRAF2, R1P1, FLIP, TAK1, JNK1/2/3, Lck, A-Raf, B-Raf, C-Raf, MOS, MLK1/3, MNK1/2, MSK1, MST2/3/4, MPSK1, MEKK1, MEKK4, MELK, ASK1, MINK1, MKK1/2/3/4/6/7, NEK2a/6/7, NUAK1, OSR1, SAPK, STK33, Syk, Lyn, PDK1, PHK, PIM1/2/3, Ataxin-1, mTORC1, MDM2, p21Waf1, Cyclin D1, Lamin A, Tpl12, Myc, catenin, Wnt, IKK-beta, IKK-gamma, IKK-alpha, IKK-epsilon, ELK, p65Re1A, IRAK1, IRAK2, IRAK4, IRR, FADD, TRAF6, TRAF3, MKK3, MKK6, ROCK2, RSK1/2, SGK1, SmMLCK, SIK2/3, ULK1/2, VEGFR1, WNK1, YES1, ZAP70, MAP4K3, MAP4K5, MAPK1b, MAPKAP-K2/K3, p38 alpha/beta/delta/gamma MAPK, Aurora A, Aurora B, Aurora C, MCAK, Clip, MAPKAPK, FAK, MARK1/2/3/4, Muel, SHC, CXCR4, Gap-1.

More specifically, the target catenin exhibits transcriptional activity which is based on the interaction with several cofactors and adaptor proteins in order to form a transcription factor complex. The catenin transcription complex represents several protein-protein interactions that can be used as therapeutic targets. Peptide motifs derived from the amino acid sequence of interacting protein structures, such as alpha-helices or beta-sheets, can be used as therapeutic lead structures. Alpha-helical peptides derived from Bcl9, bcl9/2 or pygopus are preferably used as inhibitors of the catenin transcription complex.

More specifically, apoptosis (programmed cell death) of tumor cells is repressed by members of the bcl-2 family such as blc-2, bcl-x1 and mlp-1. Induction of apoptosis is regarded as a very attractive approach for tumor therapy. It is know in the literature that interaction of the negative regulators of apoptosis such as bcl-2, bcl-x1 and mcl-1 with apoptosis sensitizing proteins such as BIM, BID, NOXA, PUMA may induce apoptosis and tumor cell death. Peptide motifs derived from the amino acid sequence of interacting protein structures such as alpha-helices or beta-sheets can be used as therapeutic lead structures. Alpha-helical peptides derived from apoptosis sensitizing proteins such as BIM, BID, NOXA, PUMA are preferably used as inhibitors of the proteins which repress apoptosis such as bcl-2, bcl-x1 and mcl-1.

In another specific embodiment, subject-matter of the present invention is a conjugate of the formula E-[G-L-D (OSO$_3^-$M$^+$)$_n$]$_m$, wherein E is an enzyme, wherein the enzyme is a therapeutic enzyme including antitumor enzymes acting by destroying certain amino acids required for tumor growth; enzymes acting by destroying oligonucleotide chains, enzymes for replacement therapy (usually digestive enzymes) for the correction of various insufficiencies of the digestive tract; enzymes for the treatment of lysosomal storage diseases; enzymes for thrombolytic therapy; antibacterial and antiviral enzymes, and hydrolytic and anti-inflammatory enzymes.

In another embodiment, subject-matter of the present invention is a conjugate of the formula E-[G-L-D(OSO$_3^-$M$^{30}$)$_n$]$_m$, wherein E is a toxin polypeptide from the class of modified plant and bacterial toxins.

In another specific embodiment, subject-matter of the present invention is a conjugate of the formula E-[G-L-D (OSO$_3^-$M$^+$)$_n$]$_m$, wherein E is a toxin polypeptide from the class of modified plant and bacterial toxins, wherein the toxin polypeptides belong to the class of ribosomal inhibiting proteins and structurally derived sequences for inhibition of tumour growth.

In another very specific embodiment, subject-matter of the present invention is a conjugate of the formula $E\text{-}[G\text{-}L\text{-}D(OSO_3^-M^+)_n]_m$, wherein E is a toxin polypeptide from the class of modified plant and bacterial toxins, wherein the toxin polypeptides comprise diphtheria toxin, diphtheria toxin lacking receptor-binding activity, *pseudomonas* exotoxin A; truncated forms of *pseudomonas* exotoxin that lacks the receptor-binding domain Ia, ricin toxin, saporin, dianthin, gelonin, thricosanthin, pokeweed antiviral protein (PAP), bouganin, anthrax protective antigen, alpha toxin, abrin, apoptosis-inducing polypeptides.

In very specific embodiment, subject-matter of the present invention is a conjugate of the formula $E\text{-}[G\text{-}L\text{-}D(OSO_3^-M^{30})_n]_m$, wherein E comprises proteins selected from wild-type p53, wild-type p21, apoptosis-inducing factor 1 (AIF1), ASK1, apoptosis-inducing protein (AIP), caspase-2, caspase-3, caspase-6, caspases-7, caspase-8, caspase-9, caspase-10, Bax, serine protease, Snac, cytochrome c, Apaf-1, apoptin.

In another embodiment, subject-matter of the present invention is a conjugate of the formula $E\text{-}[G\text{-}L\text{-}D(OSO_3^-M^+)_n]_m$, wherein E is a polypeptide targeting mechanisms of mitosis for inhibition of tumor growth.

In another specific embodiment, subject-matter of the present invention is a conjugate of the formula $E\text{-}[G\text{-}L\text{-}D(OSO_3^-M^+)_n]_m$, wherein E is a toxic polypeptide selected from the group comprising desoxyribonuclease I (DNase I), desoxyribonuclease II (DNase II), polypeptides targeting alpha-tubulin, polypeptides targeting beta-tubulin, polypeptides targeting dynein, conjugates polypeptides targeting kinesin, polypeptides targeting NEDD1, polypeptides targeting transforming acidic coiled-coil protein TACC, polypeptides targeting colonic hepatic tumor overexpresses gene chTOG.

Increasing knowledge on toxin structures and mechanism of action leads to novel chemical entities which are now in preclinical and clinical research. Most natural protein toxins can be divided into three major groups, (1) toxins that damage the cell by disrupting membrane integrity, (2) toxins that disrupt the normal electrical activity of the nervous system of the intoxicated organism, (3) toxins that disrupt or interfere with cellular processes and may affect the target cells by enzymatic or non-enzymatic activities. Some members of the third group are extremely toxic polypeptides that have the capability of self translocation into the cell cytoplasm where they execute their activity that, in most cases, leads to death of the intoxicated cell. However, clinical application of engineered toxins still faces many challenges. Two major problems associated with systemic administration of immunotoxins are (1) lack of specificity resulting from the presence of the target antigen/receptor also being present on healthy tissue and (2) undesired intoxication of healthy tissue due to the immunotoxin binding to cell surface components rather than specifically to its target antigen/receptor ("target independent toxicity"). Thus, in one embodiment, subject-matter of the present application are conjugates of the formula $E\text{-}[G\text{-}L\text{-}D(OSO_3^-M^+)_n]_m$, with toxic polypeptides or toxins for the treatment of proliferative disease by intracellular delivery of these types of therapeutic effectors.

In another specific embodiment, subject-matter of the present invention is a conjugate, wherein the sulfated dendrimers are chemically conjugated to antibodies, antibody fragments or engineered proteins and enable intracellular delivery into proliferative cells such as tumor cells and inflammatory activated cells.

In a preferred embodiment, subject-matter of the present invention is a conjugate, wherein the therapeutic effector molecules E have a molecular weight equal to or below 100 kDa, more preferred below 80 kDa, even more preferred below 60 kDa, which can be achieved by conjugation of sulfated dendrimers with antibody fragments selected from scFv, scFv$_2$, Fab, single domain antibody, minibody, bite antibody, or diabody, and most preferred below 40 kDa, which can be achieved by conjugation of sulfated dendrimers with antibody fragments selected from scFv, single domain antibody, or synthetic small molecular weight peptides.

Within the group of synthetic peptides, these are open-chain peptides, cyclic peptides via N/C-terminal cyclization, cyclic peptides via cystein-cystein (disulfide) cyclization and peptides with aliphatic cycles connected via unnatural amino acids (such as stapled peptides) of up to 25 amino acids, preferably up to 20 amino acids, more preferably up to 15 amino acids, most preferably up to 10 amino acids.

Longer peptides up to 30 to 40 amino acids are also subject of the invention, particularly because additional amino acids can be employed for the purpose of spacing, introducing solubility, and imparting improved stability.

Another embodiment within the above described synthetic peptides are preferably structure motifs derived from natural binding peptides involved in protein-protein interaction and employing sequences forming specific alpha-helices. Particularly, these alpha-helical peptide sequences are characterized by a certain helicity in solution, thereby generating binding affinity to other proteins. The required degree of helicity depends on the peptide structure applied (Bernal F et al., Methods Mol. Biol. 2014, 1176, 107-14), and can be measured by the skilled artisan, e.g. by CD-spectroscopy or H-NMR (Bonache MÁ et al., ACS Comb Sci. 2014, 16, 250-258). Helicity is given in [%].

Thus, subject-matter of the present invention is a conjugate of the formula $E\text{-}[G\text{-}L\text{-}D(OSO_3^-M^+)_n]_m$, wherein E is an alpha-helical peptide directed against protein-protein interactions or molecules involved in proliferation and apoptosis of tumor cells, wherein the conjugate is localized within the tumor cell, preferably within the cytosol of tumor cells. Preferred are conjugates with m is 1. Preferred are synthetic peptides of up to 40 amino acids, preferably up to 30 amino acids, more preferably up to 20 amino acids forming alpha-helix in aqueous solution. The alpha-helix can be stabilized by employing non-natural amino acids in the sequence, and/or by forming cyclic peptides (for instance, but not limited to, head-to-tail cyclization, disulfide cyclization, hydrocarbon stapling). Preferred values of helicity of these peptides are above 40%, more preferred above 60%, even more preferred above 80%.

Comprised by the instant invention is also the surprising finding regarding the molecular weight of the therapeutic effector molecules, particularly from the group of polypeptides or proteins. It has been surprisingly found that sulfated dendrimers chemically conjugated to antibodies, antibody fragments or engineered proteins enable intracellular delivery into proliferative cells such as tumour cells. Antibodies of IgG type are proteins with an average molecular weight of 150 kDa and are usually not able to enter the cytoplasm. The degree of intracellular uptake of dendrimer antibody conjugates was investigated in a series of different tumour cell lines and was determined by FACS measurements as well as by fluorescence microscopy. It has been found that already 3 hours after starting incubation of tumour cells with dendrimer IgG conjugates, an intracellular uptake was present. The number of positive cells as well as the total degree of uptake increased by incubation of tumour cells with dendrimer IgG conjugates up to 24 hours. Furthermore, it has been surprisingly observed that the molecular weight of the protein therapeutics is critical in terms of uptake kinetics. In detail, dendrimer protein conjugates with a total molecular weight lower than 150 kDa demonstrate faster intracellular uptake and a higher degree of positive cells than complete IgG with a molecular weight of 150 kDa. Antibody fragments such as $(Fab)_2$, scFv-Fc or diabody represent proteins with an average molecular weight of 100-120 kDa. The strongest intracellular uptake is present with dendrimer protein conjugates with a molecular weight lower than 40 kDa, such as single domain antibodies (15 kDa). A skilled person can measure the degree of the intracellular uptake by tumour cells with FACS measurement at different time points after starting incubation (see also Example 15).

In one embodiment, subject-matter of the present invention are dendrimer conjugates, wherein these dendrimer conjugates are conjugates with bi-, tri- or multi-specific antibodies, antibody fragments or engineered proteins, wherein these proteins are directed to more than one molecular target and can induce therapeutic effects on different disease mechanisms at the same time.

In another specific embodiment, subject-matter of the present invention is a conjugate of the formula E-[G-L-D$(OSO_3^-M^+)_n]_m$, wherein E comprises polypeptides, which comprise one or more nuclear localization sequences (NLS) in their amino acid sequence, which are known to tag the polypeptide thereby enabling the transport into the cell nucleus by nuclear transport, e.g. involving the importin receptor. NLS is known to the skilled person (see Lange et al., J Biol Chem. 2007, 282, 5101-5) and involves usually one or more sequences of cationic amino acids (lysins, arginines).

Further subject-matter of the present invention is a conjugate of the formula E-[G-L-D$(OSO_3^-M^+)_n]_m$, wherein E is a small therapeutic effector molecule of the class of antineoplastic agents such as alkylating and alkylating-like antineoplastic agents, e.g. cisplatin, carboplatin, oxaliplatin, mechlorethamine, cyclophosphamide, ifosfamid, trofosfamid, melphalan, chlorambucil, akylsulfonate, busulfan, treosulfan, carmustin, lomustin, nimustin, estramustin, streptozotocin, procarbazin, dacarbazin, temozolomid, thiotepa, duocarmycin and analogues, centanamycin, adozelesin, bizelesin, carzelesinor, a therapeutic effector molecule of the class of anti-metabolites such as purine analogues (6-thioguanin, pentostatin, azathioprin, 6-mercaptopurin, fludarabin, cladribin) or pyrimidine analogues (gemcitabin, 5-fluouracil) or antifolates (methotrexate), plant alkaloids and terpenoids with antimitotic activity such as vinca alkaloids (vincristine, vinblastine, vinorelbine, vindesine), disorazoles and derivatives (disorazole A1, A2, E1, Z), podophyllotoxin such as etoposide and teniposide, taxanes (docetaxel, paclitaxel), colchicines and derivatives, maytansine and derivatives including analogues with linkers, geldanamycin and analogues such as aminoheyxlgeldanamycin or 17-aminogeldanamcyin; topoisomerase inhibitors such as camptothecin derivates irinotecan and topotecan, amsacrine, etoposide, etoposide phosphate, and teniposide, antitumour antibiotics such as dactinomycin, doxorubicin, daunorubicin, 2-pyrrolinodoxorubicin, epirubicin, bleomycin, mitomycin, pyrrolobenzodiazepines (PBDs) such anthramycin, mazethramycin, tomaymycin, and analogues such as PBD dimers, tyrosine kinase inhibitors and multi-kinase inhibitors such as staurosporine, afatinib, axitinib, cabozantinib, crizotinib, dabrafenib, foretinib, flumatinib, imatinib, ponatinib, regorafenib, rigosertib, sorafenib, sunitimib, tasocitinib, vandetanib, vemurafenib, ruxolitinib, tasozitinib, trametinib and analogues of these agents with functional groups for covalent conjugation; other synthetic or semisynthetic anti-mitotic agents, such as auristatin derivatives, including monomethylauristatin E, monomethylauristatin F and analogues, dolastatin derivatives including monomethyldolastatin N and analogues, tubulysin and analogues, calicheamicin and derivatives including calicheamicin 1 and N-acetyl γ calicheamicin DMH; RNA polymerase II inhibitors such as the cyclic peptide alpha-amanitin and analogues.

In another specific embodiment, subject-matter of the present invention is a conjugate of the formula E-[G-L-D$(OSO_3^-M^{30})_n]_m$, wherein E is a therapeutic effector molecule, wherein the polypeptide effector molecules are antibodies and antibody fragments, which are conjugated to small therapeutic effector molecule of the class of antineoplastic agents.

In one specific embodiment, subject-matter of the present invention is a conjugate, wherein the polypeptide effector molecules conjugated to small therapeutic effector molecule of the class of antineoplastic agents are selected from trastuzumab-DM1 (antibody conjugated to maytansine), antibodies or diabodies conjugated to monomethyl auristatin E or F, antibodies conjugated to calicheamicin.

In another embodiment, subject-matter of the present invention is a conjugate of the formula E-[G-L-D$(OSO_3^-M^+)_n]_m$, wherein E is a small therapeutic effector molecule of the class of photosensitizers such as tetrapyrroles, porphyrins, sapphyrins, chlorins, tetraphenylporphyrins, tetraphenylchlorins, bacteriochlorins, tetraphenyl-bacteriochlorins, pheophorbides, bacteriopheophorbides, pyropheophorbides, bacteriopyropheophorbides, purpurinimides, bacteriopurpurinimides, benzoporphyrins, phthalocyanines, naphthalocyanines and derivatives thereof. Preferably, the photosensitizer is selected from the group comprising pheophorbide a, pyropheophorbide a, 3-acetylpheophorbide a, 3-acetylpyropheophorbide a, purpurin-18-N-alkylimide, purpurin-18-N-hydroxylimide, 3-acetylpurpurin-18-N-alkylimide, 3-acetylpurpurin-18-N-hydroxylimide, chlorine e6, Sn-chlorine e6, m-tetrahydroxyphenylchlorin (m-THLC) and benzoporphyrin derivative, benzoporphyrin derivative monoacid (BPD-MA, verteporfin).

In another preferred embodiment, subject-matter of the present invention is a conjugate of the formula E-[G-L-D$(OSO_3^-M^+)_n]_m$, wherein G is a connecting functional group forming the covalent attachment between E and L.

In another specific embodiment, subject-matter of the present invention is a conjugate of the formula E-[G-L-D$(OSO_3^-M^+)_n]_m$, wherein G is selected from the group consisting of O, S, NH, NH—O, C(=O)NH, OC(=O)NH, OC(=O)O, NHC(=O)NH, NHC(=S)NH, C(=NH)NH, C(=O), S(=O)$_2$, S(=O), S(=O$_2$)O, S—S, CH=N, CH=N—NH, C=N—NHC(=O), OP(=O)(O$^-$M$^+$)O, P(=O)(O$^-$M$^+$)O, arylene, ethenylene ethinylene, and triazolylene.

In another very specific embodiment, subject-matter of the present invention is a conjugate of the formula E-[G-L-D$(OSO_3^-M^+)_n]_m$, wherein G is formed by the conjugation reaction between a reactive group at linker L and the therapeutic effector molecule E. Reactive groups comprise COOH, activated esters of COOH such as N-hydroxysuccinimidyl ester, N-hydroxysulfosuccinimidyl ester, p-nitrophenyl ester, pentafluorphenyl ester or sulfodichlorophenyl ester; amino, hydrazine, carboxyhydrazino, isothiocyanate, isocyanate, maleimido, tetrazine, vinylsulfonic ester, vinylsulfone amide, bromoacetyl, iodoacetyl, bromoacetyl amide, iodoacetyl amide, carbaldehyde, thiol, pyridyl disulfide, thioacetyl, azido, propargyl, ethinyl, allyl, vinyl, (difluoro)cyclooctynyl, triarylphosphine, bis(alkyloxy)arylphosphine, (glycyl)glycylglycine, guanidine. Preferred are connections of the following structures: C(O)NH derived from an activated ester at L (comprising N-hydroxysuccinimdyl ester, Sulfo-N-hydroxysuccinimdyl ester, p-nitrophenyl ester), NHC(S)NH derived from an isothiocyanate group at L, —S-succinylamide derived from a maleimido group at L, disulfide —S—S— derived from pyridyldisulfide or acetylsulfide at L, triazole derived from a terminal propargyl group or a cyclooctinyl group at L, —CH=N-(imine) derived from an aldehyde group at L, —CH$_2$—NH— (amine via imine by reductive amination) derived from an aldehyde group at L.

In another preferred embodiment, subject-matter of the present invention is a conjugate, wherein G for the connection comprises an amide bond C(O)NH, which is part of a peptide chain derived from an enzyme ligation reaction.

Further subject-matter of the present invention is a conjugate of the formula E-[G-L-D(OSO$_3^-$M$^+$)$_n$]$_m$, wherein the counter ion M$^+$ comprises organic and inorganic cations, selected from lysine, meglumine, TRIS, glycine or other amines derived from amino acids, or potassium, sodium, lithium, or mixtures thereof.

In another embodiment, subject-matter of the present invention is a conjugate according to Formula E-[G-L-D(OSO$_3^-$M$^+$)$_n$]$_m$, wherein m is a number between 1 to 20, describing that the embodiment comprises 1 or more sulfated dendrimer-linker systems G-L-D(OSO$_3^-$M$^+$)$_n$ being connected to the therapeutic effector molecule E.

Further subject-matter of the present invention is a conjugate of the formula E-[G-L-D(OSO$_3^-$M$^+$)$_n$]$_m$, wherein n is the number of sulfate groups selected from 6 to 96.

In a preferred embodiment, subject-matter of the present invention is a conjugate, wherein n is an even number selected from 6, 8, 12, 16, 18, 24, 30, 32, 36, 40, 48, 72 or 96.

For the dendrimer D(OSO$_3^-$M$^+$)$_n$ the number of sulfates is also related to its resulting molecular weight composed by the dendritic structure and the sulfate groups including counter ion. It was found that the density of sulfates shall be in a specific embodiment at a certain level. Thus, the molecular weight of D(OSO$_3^-$M$^+$)$_n$ is limited for each number n in a specific embodiment of the invention.

Preferred are dendrimers D(OSO$_3^-$M$^+$)$_n$ with the following relations between n and molecular weight, given for M$^+$ being an alkali ion, preferably sodium.

| number of sulfates (n) | Molecular weight of D(OSO$_3^-$M$^+$)$_n$ not exceeding |
|---|---|
| 6 | 2000 Da |
| 8 | 2400 Da |
| 12 | 4000 Da |
| 16 | 5500 Da |
| 18 | 6000 Da |
| 24 | 8000 Da |
| 30 | 10000 Da |
| 32 | 11000 Da |
| 36 | 12000 Da |
| 40 | 13000 Da |
| 48 | 16000 Da |
| 72 | 24000 Da |
| 96 | 32000 Da |

According synthetic pathways to yield hydroxylated dendritic structures (polyol structures), a certain number of sulfate groups is preferred, selected from the number n being 6 or greater. It was surprisingly found that a highly sulfated dendrimer coupled to an antibody fragment (50 kDa, fluorescence labeled in the Cy3 range with dye ICC, see example 8) allowed an 3-fold higher detection in tumor cells with a number of sulfates of 24 or 32, compared to an analog conjugate with a number of sulfates of 12 or 16. However, by using a small molecular effector E (1200 Da) a similar effect was observed with a dendrimer of 12 and 18 sulfate groups.

Therefore and due to convenience in the synthesis process, an even number of n of 12, 16, 18, 24, 30, 32, 36, 40, 48, 72 or 96 is subject-matter of the present invention in one preferred embodiment. Preferably, n is 12, 18, 24, 32, 36, 40 or 48. When E stands for a protein of molecular weight above 40 kDa, n is preferably 24, 32, 36, 40, 48 or greater. When E stands for a small molecule compound or peptide of approximately 600 to 2000 Da, or a protein of 1200 to 40000 Da, n is preferably 12, 16, 24 or 32. When m is 2 or greater, n is preferably 6, 12, 16 or 24.

Further subject-matter of the present invention is a conjugate of the general formula E-[G-L-D(OSO$_3^-$M$^+$)$_n$]$_m$ for use in treating a disease by intracellular uptake into activated cells or proliferative cells.

In a preferred embodiment, subject-matter of the present invention is a conjugate of formula E-[G-L-D(OSO$_3^-$M$^+$)$_n$]$_m$ for use in treating a disease selected from the group comprising cancer, inflammation, autoimmune disease, metabolic disease and fibrosis, as well as for anti-proliferative, pro-proliferative, anti-apoptotic, pro-apoptotic, anti-fibrotic, pro-fibrotic, anti-lipogenic, anti-diabetic, immune-stimulatory and anti-aging treatment.

In a more preferred embodiment, subject-matter of the present invention is a conjugate of sulfated dendrimers and therapeutic molecules for the use in treatment and diagnosis of metabolic diseases, wherein said conjugates of sulfated dendrimers and therapeutic molecules are directed against molecular targets in liver cells such as hepatocytes or hepatic stellar cells.

In a more specific embodiment, subject-matter of the present invention is a conjugate of sulfated dendrimers and therapeutic molecules for the use in diagnosis and treatment of metabolic diseases such as diabetes, alcoholic liver disease, drug-induced or "toxic" liver disease, fatty liver disease (hepatic steatosis), non-alcoholic fatty liver disease, steatohepatitis, secondary cirrhosis, primary biliary cirrhosis, primary sclerosing cholangitis, Budd-Chiari syndrome, hemochromatosis, hereditary amyloidosis, Gilbert's syndrome.

In an even more specific embodiment, subject-matter of the present invention is a conjugate of sulfated dendrimers and therapeutic molecules for the use in treatment and diagnosis of viral diseases of the liver, wherein said conjugates are directed against viral and non-viral molecular targets in liver cells such as hepatocytes or hepatic stellar cells.

In another more specific embodiment, subject-matter of the present invention is a conjugate of sulfated dendrimers and therapeutic molecules for the use in diagnosis and treatment of metabolic diseases such as hepatitis A, hepatitis B, hepatitis C, hepatitis C, hepatitis D, hepatitis E, Epstein-Barr-virus induced hepatitis, cytomegalie virus induced hepatitis, herpes simplex virus induced hepatitis, rubella virus, mumps virus induced hepatitis, rubella virus induced hepatitis, adeno virus induced hepatitis, yellow fever induced hepatitis.

In another preferred embodiment, subject-matter of the present invention is a conjugate of sulfated dendrimers and therapeutic molecules for the use in diagnosis and treatment, wherein the therapeutic molecules conjugated with sulfated dendrimers can be selected from the group of deleburir, ledipasvir, lamivudine, adefovir, dipivoxil, televudine, tenafavir, ribavarin, telaprevir, boceprevir, simeprevir, asunaprevir, faldaprevir, sofosbuvir, daclatasvir, vaniprevil, entecavir, ABT-333, ABT-072, BMS-791325, interferon-alpha, pegylated interferon-alpha, VX-950, VX-222, VX-985, ALS-2200, ALS-2158, SIRNA-034, MK-0608, R7227, R7128 (R05024048), RG7348, TMC435, TMC649128, PF-868554, PF-4878691, BI 201335, BI207127, IC41, BMS-790052, BMS-791325, BMS-650032, BMS-824393, ANA598, VCH-759, GI 5005, ITX5061, ITX4520, IDX184, IDX320, IDX375, A-837093, GS 9190, GS9256, ACH-1095, ACH-1625, ACH-2684, ACH-2928, PPI-461, PPI-1301, TG4040, AZD7295, MBL-HCV1, Clemizole, SPC3649, Locked Nucleic Acid mRNA122 inhibitor, GNI-103, GNI-104, GSK625433, ABT-450, ABT-072, INX-189, PSI-938, EDP-239, SP-30, AVL-181, AVL-192, ATI-0810, PRO 206, ITX2155, VX-500, VX-813, Albuferon albinterferon alfa-2b, SCV-07, MX3235 Celgosivir, KPE02001003, KPE00001113, CTS-1027, CB5300, Debio 025, MDX-1106 (ONO-4538), CYT107, CB-183872, REP 9C broad-spectrum entry inhibitor, AN 025-1, GEA007.1, IMMU 105.

Further subject-matter of the present invention is a pharmaceutical composition comprising the conjugate according to Formula E-[G-L-D(OSO$_3^-$M$^+$)$_n$]$_m$.

In one specific embodiment, subject-matter of the present invention is a pharmaceutical composition, wherein said composition has a unit dosage form, such as tablets, pills, capsules, powder, granulate, sterile parenteral solutions or suspensions.

In another specific embodiment, subject-matter of the present invention is a pharmaceutical composition, wherein the composition is a solid formulation of the conjugate according to Formula E-[G-L-D(OSO$_3^-$M$^+$)$_n$]$_m$ together with known pharmaceutically acceptable carriers and/or excipients.

In a preferred embodiment, subject-matter of the present invention is a pharmaceutical composition, wherein the pharmaceutical dosage form is a lyophilisate.

In a more preferred embodiment, subject-matter of the present invention is a pharmaceutical composition, wherein the route of administration is parenteral, including subcutaneous, intravenous, intraperitoneal, intraocular, intramuscular, intratumoral.

In an even more preferred embodiment, subject-matter of the present invention is a pharmaceutical composition, wherein the route of administration is selected from an intravenous, subcutaneous or intraperitoneal route of administration, including the multiple dosages of compounds, including daily treatment, treatment every 2 up to 7 days, treatment more than once daily, or time intervals such as treatment in intervals of five days.

In an another preferred embodiment, subject-matter of the present invention is a pharmaceutical composition for use in multiple treatment, wherein the multiple treatment of patients comprises a subcutaneous dose of 0.1 mg/kg up to 1000 mg/kg, preferably 0.1 mg/kg to 100 mg/kg, most preferably 1 mg/kg to 10 mg/kg body weight.

In another specific embodiment, subject-matter of the present invention is a conjugate according to Formula E-[G-L-D(OSO$_3^-$M$^+$)$_n$]$_m$, wherein the number m can differ depending on the nature of molecule E used according to said formula. Exemplary embodiments are in detail described below in the context of their synthesis. Further subject-matter of the present invention is the use of proteins according to general formula E-[G-L-D(OSO$_3^-$M$^+$)$_n$]$_m$, wherein the conjugation of D via linker L with connecting group G occurs to amino groups of lysins, which is a procedure of statistical conjugation known to the skilled artisan. Examples 11-13 demonstrate several possibilities. The conjugation occurs statistically depending on the number of accessible amino functions. Thus, the molar ratio of dendrimer system G-L-D(OSO$_3^-$M$^+$)$_n$ to the polypeptide is described by the number m, being in average 1 or above. Preferred are an average ratio between 1 and 5, more preferred between 1 and 3 for statistical conjugation, wherein each of the dendrimers D has the same molecular weight. This means that each sulfated dendrimer conjugated to E has the same molecular weight, but the conjugate can be composed of a mixture of conjugates each having a molar ratio described by one specific value of m, preferably between 1 to 10. This leads to inhomogeneous mixtures based on an average number for m. This average number can be determined analytically by the skilled artisan, e.g. by HPLC or photometric analysis.

In another preferred embodiment, subject-matter of the present invention is a conjugate according to Formula E-[G-L-D(OSO$_3^-$M$^+$)$_n$]$_m$, wherein E comprises thiol, whereby these are thiol groups of internal cysteins which are usually accessible by reduction of disulfide bonds. Thiols are preferably labeled with maleimide (e.g. dendrimers d02, d03, d13, d14, d19, d20) forming a thioether, or pyridyldisulfide (e.g. dendrimers d04, d05, d15, d21) forming a disulfide for G.

In a preferred embodiment, subject-matter of the present invention is a conjugate according to Formula E-[G-L-D(OSO$_3^-$M$^+$)$_n$]$_m$, wherein the effector molecule E based on polypeptides or small molecules effector molecules can be synthetically modified in order to introduce reactive functional groups which are not present in the parent polypeptide, are not accessible or cause loss of functionality of E, when the respective functional group is covalently conjugated to the sulfated dendrimers, e.g. thiol groups of internal cysteins which were generated by reduction of disulfide bonds. Examples of reactions of polypeptides to introduce functional groups, like thiol or azide, are reactions with 2-iminothiolane, acetylthiopropionic acid, azidoalkylcarboxylic acids, azido-PEG-alkylcarboxylic acids and others, as known to the skilled artisan (Bioconjugate Techniques; Greg T. Hermanson; Academic Press, 2008).

In a preferred embodiment, subject-matter of the present invention is the use of polypeptides that are biotechnologically engineered to carry structures at defined positions in the polypeptide sequence which have the function of covalent, site-specific conjugation with payloads (Wang et al., Front Biosci. 2008, 13, 1716). Well known are cystein motifs (Cys-tag, such as the amino acid sequence GGGCA or GGGCGGG), azide functions for click labeling encoded via methionine replacement by azidohomoalanine (Kiick et al., PNAS 2002, 99, 19-24), or motifs for enzymatic ligation, such as the sortase-mediated ligation of the C-terminal sequence LPXTG with a N-terminal glycine motif (Popp et al., Nature Chem Biol., 2007, 11, 707). The polypeptides are accessible via known technology of recombinant production or by solid-phase peptide synthesis. Thus, the embodiment comprises also a molar ratio m of dendrimer system G-L-D(OSO$_3^-$M$^+$)$_n$ to the polypeptide being exactly 1 due to site-directed conjugation, in contrary to the statistical conjugation giving average numbers for m, as described above. Preferred is the conjugation to thiol group of a cys-tag with maleimide forming a thioether, or pyridyldisulfide forming a disulfide for G, as well as the sortase-mediated enzymatic ligation for the sequence LPXTGG (e.g. with dendrimer d25), and the click-labeling of azides derived from azidohomoalanine.

In a specific embodiment, subject-matter of the present invention is a conjugate according to Formula E-[G-L-D$(OSO_3^-M^+)_n]_m$, wherein the effector molecule E has a higher molecular weight than the conjugated sulfated dendrimer. A preferred embodiment comprises conjugates wherein E is based on a polypeptide which has an up to 20-fold higher molecular weight (in Dalton) related to the sum of molecular weight given by the number n of identical dendrimer units [G-L-D$(OSO_3^-M^+)_n]_m$ conjugated to the polypeptide, more preferred an up to 10-fold molecular weight, even more preferred an up to 5-fold molecular weight.

In another embodiment, subject-matter of the present invention is a conjugate according to Formula E-[G-L-D$(OSO_3^-M^+)_n]_m$, wherein E is a therapeutic polypeptide from the class of enzymes that abolish indispensible nutrients or factors from the tumour cells cytosol. For example, dendrimer L-asparaginase conjugates were surprisingly found to act as strong antiproliferative agent in many tumour cell lines. So far, a skilled person was not able to deliver the therapeutic macromolecule L-asparaginase into the tumour cell cytosol. However, this feature is of utmost importance as the majority of tumour cells can compensate lack of asparagines uptake by intracellular de novo synthesis. This includes also dendrimer protein conjugates targeting tumour metabolism. Preferred are enzyme proteins as therapeutic effector molecules such as glycosylases, hydrolases, pyruvate kinases, fumarate hydratases, hexokinases, aldolases, enolases, glucose phosphate isomerases.

In a particularly preferred embodiment, subject-matter of the present invention according to Formula E-[G-L-D$(OSO_3^-M^+)_n]_m$ is a conjugate of dendrimer systems with L-asparaginase, which is a homotetramer, each of the four units providing one disulfide bridge for reduction and conjugation without loss of enzymatic function (Balan et al., Bioconjugate Chem. 2007, 18, 61), see Example 12a for synthesis and Example 15 and 16 for biological data.

In another embodiment, subject-matter of the present invention is the use of protein A or protein G, which is available in different formats, including those employing a cystag. For example, dendrimers are conjugated to rCys-proteinG (example 12c), maintaining the binding affinity of protein G to the Fc-structure in murine or human IgG. Subject-matter of the invention are therefore dendrimer conjugates according to Formula E-[G-L-D$(OSO_3^-M^+)_n]_m$, in which the therapeutic effector is an IgG antibody—protein A or protein G complex, with covalent conjugation of the sulfated dendrimer to protein A or G, using conjugation techniques as described above. The number m is preferably 1, 2 or 3, using one sulfated dendrimer at the protein A or G, and adjusting the ratio between IgG and dendrimer protein A/G by non-covalent assembly in solution.

In a preferred embodiment, subject-matter of the present invention is a method for treating a disease as described above comprising the use of conjugates of sulfated dendrimers with therapeutic effector molecules according to Formula E-[G-L-D$(OSO_3^-M^+)_n]_m$, therapeutic effector E is delivered to the cytosol. Even more preferred is this method, wherein the delivery to the cytosol occurs with linkers L being stable thereby not allowing release/cleavage of the therapeutic effector E from the sulfated dendrimer. The measurement of drug release from a carrier molecule can be done by methods known to the skilled person, e.g. described by Wakankar et al., MAbs 2011, 3, 161-172, including methods of HPLC or mass spectroscopy used to analyse drug conjugates incubated in human serum. Within the embodiment, a preferred method is the herein described application with a stability of disclosed dendrimer conjugates, leading to free drug not more than preferably 10%, more preferably 5% of the conjugated amount (100%), measured after 24 h incubation in hum aserum at 37° C. by HPLC.

In a preferred embodiment, subject-matter of the present invention is a method for treating a disease as described above comprising the use of conjugates of sulfated dendrimers with therapeutic effector molecules according to E-[G-L-D$(OSO_3^-M^+)_n]_m$, wherein the therapeutic effector E is not applicable as drug alone without conjugation due to plasma and tissue concentrations at levels too toxic to the organism. These are preferably maytansine and analogues, auristatin and analogues, and staurosporine and analogues. Conjugates of sulfated dendrimers with these therapeutic molecules exhibit much lower toxicity to non-proliferating cells compared to the drug molecules alone. In the organism, low plasma levels of free drug are detected, when using a non-cleavable linker structure for L that stable under physiological conditions in the organism.

Another aspect of the embodiment regards the therapeutic compounds E with respect to their property to exhibit only limited penetration into the cell without conjugation to sulfated dendrimer. These are usually the protein and polypeptide structures as described above, but also hydrophilic synthetic cytotoxic compounds. The example 15 shows, that the protein L-asparaginase do not show uptake into tumor cells, whereas L-asparaginase conjugated to sulfated dendrimer shows a substantially enhanced concentration inside tumor cells (table 5). Hence, upon dendrimer conjugation, cellular uptake is enhanced. Further subject-matter of the present invention is therefore a method, wherein 3-fold, preferably 5-fold, most preferably above 10-fold enhanced uptake occurs, with respect to the number of conjugate molecules of sulfated dendrimers with therapeutic effector molecules according to Formula E-[G-L-D$(OSO_3^-M^+)_n]_m$ localizing within the cell (e.g. measured in FACS using dye-labeled conjugates, see example 15) relative to non-conjugated therapeutic molecules E Within the scope of the present invention, the compounds according to Formula E-[G-L-D$(OSO_3^-M^+)_n]_m$ exhibit a cytotoxic effect on tumour cells, as also described within supporting examples. This effect can be quantified by an $IC_{50}$ value in M [mol/L], as given for several examples. It is therefore also subject-matter of the present invention to provide a method for treating a disease as described above comprising the use of conjugates of sulfated dendrimers with therapeutic effector molecules according to said Formula by exhibiting an $IC_{50}$ value in culture of tumour cells less than $10^{-7}$ M, preferably less than $10^{-8}$ M, more preferably less than $10^{-9}$ M. It is understood that this value can differ depending on the cell line used and the method of analysis (which can be cell proliferation analysed by MMT test, or cell counting of alive vs. dead cells).

Among the group of proteins that act as binding reagents and usually applied to block protein-protein interaction, engineered polypeptide scaffolds are of strong significance. Polypeptide scaffolds represent polypeptides carrying a rigid natural polypeptide structure that can be used to modify an existing or to implement a new binding site for a molecular target. Usually, such a scaffold is derived from a robust and small soluble monomeric polypeptide (such as the Kunitz inhibitors or the lipocalins) or from a stably folded extramembrane domain of a cell surface receptor (e.g. protein A, fibronectin or the ankyrin repeat). Compared with antibodies or their recombinant fragments, these polypeptide scaffolds often provide practical advantages including elevated stability and high production yield in microbial expression systems, together with an independent intellectual property situation. As these binding polypeptide are obtained by means of a biomolecular engineering process in order to achieve tight target-binding activity, they may also be subjected to further selection schemes focused at other desired properties (such as solubility, thermal stability, protease resistance etc.). More than 50 different polypeptide scaffolds have been proposed over the past 10-15 years. The most advanced approaches in this field comprise the following polypeptide classes (1) affibodies based on the Z-domain of staphylococcal protein A, a three-helix bundle of 58 residues providing an interface on two of its a-helices, (2) engineered Kunitz domains based on a small (ca. 58 residues) and robust, disulfide-crosslinked serine protease inhibitor, typically of human origin (e.g. LACI-D1), which can be engineered for different protease specificities, (3) monobodies or adnectins based on the 10th extracellular domain of human fibronectin III (10Fn3), which adopts an Ig-like b-sandwich fold (94 residues) with 2-3 exposed loops, but lacks the central disulfide bridge, (4) anticalins derived from the lipocalins, a diverse family of eight-stranded b-barrel proteins (ca. 180 residues) that naturally form binding sites for small ligands by means of four structurally variable loops at the open end, which are abundant in humans, insects, and many other organisms, (5) DARPins, designed ankyrin repeat domains (166 residues), which provide a rigid interface arising from typically three repeated b-turns and, finally, a few other binding proteins based on more peculiar folds such as a multimerized LDLR-A module (Avimers or cysteine-rich knottin peptides).

Besides many attractive properties of engineered scaffolds, they are hampered by their low molecular weight which leads to a fast elimination after intravenous injection. Further subject-matter of the present invention are conjugates of dendrimers and engineered polypeptides for intracellular delivery of the engineered polypeptides in order to interfere with mechanisms of tumour growth. In a preferred embodiment, subject-matter of the present invention are conjugates of sulfated dendrimers and engineered polypeptides, wherein the polypeptides are dendrimer affibody conjugates, dendrimer kunitz conjugates, dendrimer anticalin conjugates, dendrimer affilin conjugates, dendrimer monobody (adnectin) conjugates, dendrimer DARPIN conjugates and dendrimer peptide conjugates. In a particularly preferred embodiment, subject-matter of the present invention are conjugates of dendrimer and engineered proteins which exert high binding affinity to the therapeutic target in the picomolar range and high stability such as DARPins.

It is known to a skilled person that engineered scaffold polypeptides can be synthesized and expressed as dimers or multimers of more than 3 polypeptide chains with target binding to the identical antigen, as well as similar or different antigens. Hereby, an increase of circulatory half-life in the blood and an increase of the strength of the target binding can be achieved. Conjugates of dendrimers and dimeric or multiple engineered polypeptides are inventive and not known in the literature. It has been surprisingly observed that conjugates of dendrimers and an engineered scaffold consisting of 2 to 100 repeated polypeptide chains have a much stronger growth inhibitory activity than conjugates of dendrimer and a single engineered polypeptide. Therefore in a preferred embodiment, subject-matter of the present invention are conjugates of dendrimers and 2 to 20 repeated polypeptide chains. In a particularly preferred embodiment, subject-matter of the present invention are conjugates of dendrimers and 2 to 10 repeated polypeptides. In another embodiment, subject-matter of the present invention are conjugates of dendrimers and multiple repeated polypeptides, wherein the polypeptides are connected by cleavable linker molecules, such as enzymatically cleavable amino acid sequences.

Another aspect of the invention is related to the molecular binding inhibition of L-selectin, which can be determined as described by Dernedde et al. in PNAS, 2010, 107, 19679-84. Herein, polymeric, non-defined polyglycerolsulfate ($M_n$~10 kDa) exhibits high capability of L-selectin binding inhibition with an $IC_{50}$ of 8 nM, for example, using a polymer with 61 sulfate groups in average. With a defined sulfated dendrimer according to the invention, comparably bearing 48 sulfate groups, the values (~300 nM) are surprisingly higher indicating much weaker L-selectin binding inhibition. Therefore, subject-matter of the present invention is the provision of compounds according to formula E-[G-L-D$(OSO_3^-M^+)_n]_m$, which exhibit values for $IC_{50}$ of L-selectin binding inhibition of >30 nM, preferably >100 nM, more preferably >300 nM, most preferably >500 nM, measured according to PNAS, 2010, 107, 19679-84.

Further preferred embodiments of the invention are reflected by the below consecutively numbered sentences:

1. Conjugate of the formula

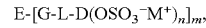

E-[G-L-D$(OSO_3^-M^+)_n]_m$, wherein E is a therapeutic or diagnostic effector molecule,
   wherein D$(OSO_3^-M^+)_n$ is a dendrimer D carrying a number n of sulfate groups
   $OSO_3^-M^+$, wherein the number n of sulfate groups is selected from 6 to 96,
   wherein M is a cationic inorganic or organic counter ion to the anionic sulfate group,
   wherein L is a linker or spacer between D and E,
   wherein G is a connecting functional group forming the attachment between L and E,
   and wherein m is an integer from 1 to 20.

2. Conjugate according to embodiment 1, wherein each of the dendrimers D of said conjugate has the same molecular weight.

3. Conjugate according to embodiment 1 or 2, wherein the number n of sulfate groups is the same for each dendrimer D.

4. Conjugate according to any one of embodiments 1 to 3, wherein the repeating units of monomers to build the dendrimer D are selected from the group consisting of 1,2-substituted glycerol, 1,3-substituted glycerol, pentaerythritol, glucose, mannose, galactose, lysine, tris(hydroxymethyl)aminomethane, tris(propionic acid) aminomethane, 1,1'-bis(hydroxymethyl)-propionic acid, succinic acid, glutaric acid, maleic acid, glycolic acid, diglycolic acid, adipic acid, lactic acid, citric acid, propionic acid (2-aminoethyl)amide, propyleneimine, ethyleneimine, propyleneoxide, and ethyleneoxide.

5. Conjugate according to any one of embodiment 1 to 4, wherein the connection of said monomers in the dendrimer D is based on functional groups selected from ether, thioether, carboxylic ester, sulfonylester, sulfonamide, carboxylamide, amine, carbamate, thiocarbamate, urea, thiourea, hydrazone, imine, disulfide, phosphate, phosphonate, triazole, acetal, and ketal.

6. Conjugate according to embodiment 1 to 5, wherein D contains terminal groups selected from 1,2-disulfatoalkyl, 1,3-disulfatoalkyl, 1,2,4-trisulfato-3-alkyl, N,N'-di (1-sulfatoalkyl)amine, tris(sulfatomethyl)methyl, and 1,2,3,4,5-pentasulfatoalkyl.

7. Conjugate according to embodiment 1, wherein L is a $C_{4-100}$-alkyl group, selected from the group consisting of aliphatic cyclic, branched or linear units in which one or more methylene groups may independently be replaced by a unit selected from the group consisting of O, S, NH, NH—O, C(=O)NH, OC(=O)NH, OC(=O)O, NHC(=O)NH, NHC(=S)NH, C(=NH) NH, C(=O), S(=O)$_2$, S(=O), S(=$_2$)O, S—S, CH=N, CH=N—NH, C=N—NHC(=O), OP(=O) (O$^-$M$^+$)O, P(=O)(O$^-$M$^+$)O, arylene, ethenylene or ethinylene, and triazolylene, in which any hydrogen atom may independently be replaced by methyl, ethyl or hydroxymethyl.

8. Conjugate according to embodiment 1, wherein E is a therapeutic or diagnostic effector molecule.

9. Conjugate according to embodiment 8, wherein the effector molecules are selected from the group consisting of small molecules, peptides, proteins, glycans, and nucleic acids.

10. Conjugate according to embodiment 8 or 9, wherein the effector molecule is a therapeutic effector molecule comprising substances which may interfere with intracellular mechanisms of proliferation, apoptosis, synthesis of connective tissue material (e.g. collagen, fibronectin), immune function, senescence, or immune defence.

11. Conjugate according to embodiment 9, wherein the small molecule is selected from the group consisting of cytostatic agents, and peptide or peptidomimetic structures, including cyclic or open-chain peptides with natural or non-natural structural modifications.

12. Conjugate according to embodiment 9, wherein the proteins are selected from the group consisting of globular proteins, glycoproteins, toxins, enzymes, antibodies, antibody fragments, engineered antibody and protein constructs, including single domain antibodies (sdAb), single chain Fv antibodies (scFv), single chain-Fv-Fc antibodies (scFv-Fc).

13. Conjugate according to any one of embodiment 8 to 12, wherein E is directed against molecules involved in proliferation and apoptosis of tumor cells.

14. Conjugate according to embodiment 1, wherein G is a connecting functional group forming the covalent attachment between E and L, selected from the group consisting of O, S, NH, NH—O, C(=O)NH, OC(=) NH, OC(=O)O, NHC(=O)NH, NHC(=S)NH, C(=NH)NH, C(=O), S(=O)$_2$, S(=O), S(=O$_2$)O, S—S, CH=N, CH=N—NH, C=N—NHC(=O), OP(=O)(O$^-$M$^+$)O, P(=O)(O$^-$M$^+$)O, arylene, ethenylene ethinylene, and triazolylene.

15. Conjugate according to any one of embodiment 1 to 14 for use (i) in treating a disease selected from the group comprising cancer, inflammation, autoimmune disease, metabolic disease and fibrosis, or (ii) in anti-proliferative, pro-proliferative, anti-apoptotic, pro-apoptotic, anti-fibrotic, pro-fibrotic, anti-lipogenic, anti-diabetic, immune-stimulatory and anti-aging treatment.

16. Pharmaceutical composition comprising the conjugate according to any one of embodiments 1 to 15.

17. Conjugate according to embodiment 1, wherein m is 1.

18. Conjugate according to any one of embodiments 1 to 15, wherein said dendrimer D comprises a central dendrimer core unit (CDCU) selected from the group of

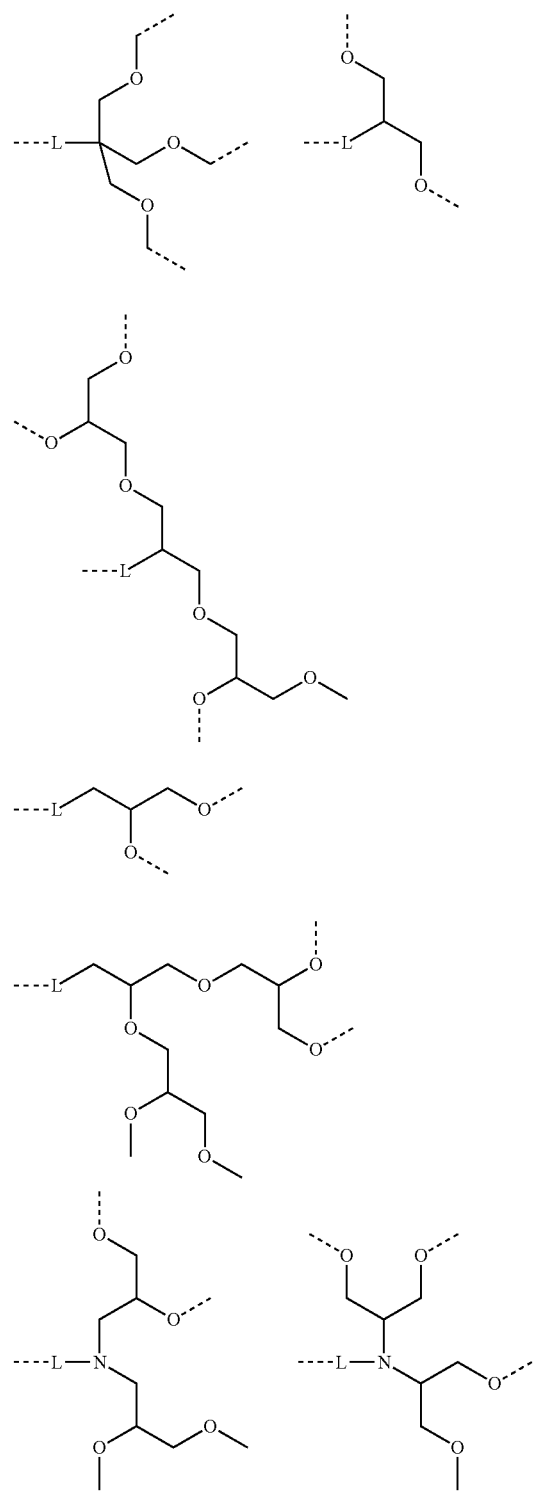

-continued
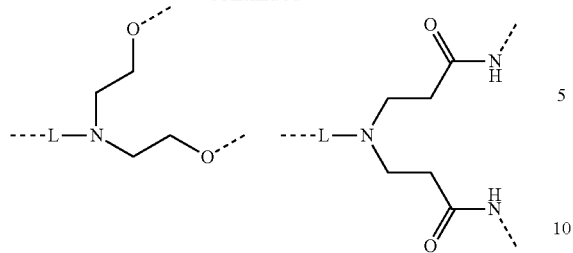
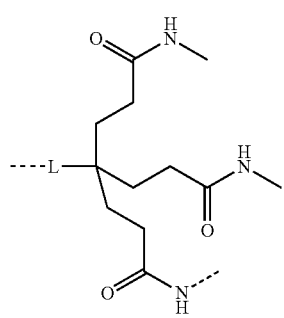
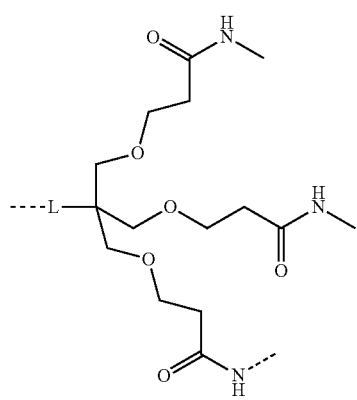
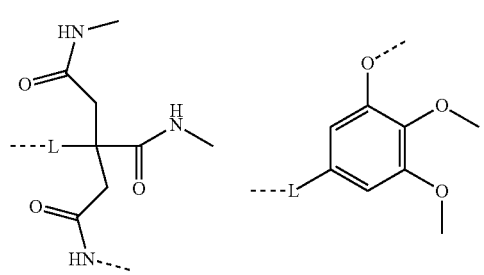
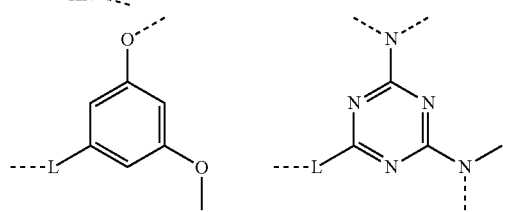
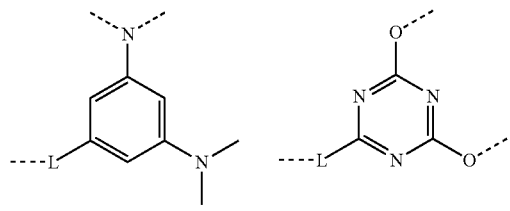
-continued
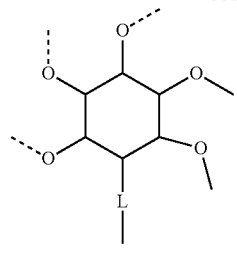
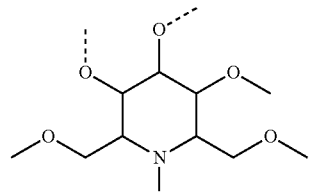
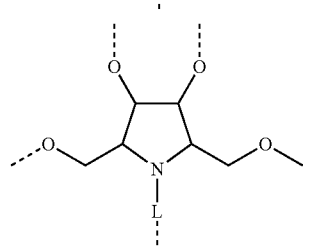
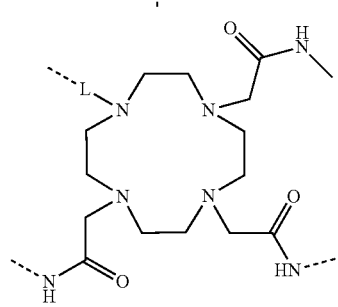
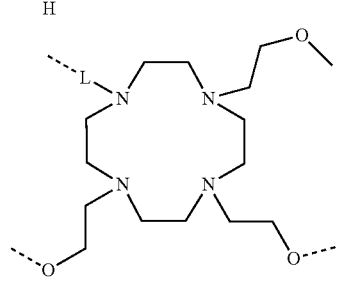
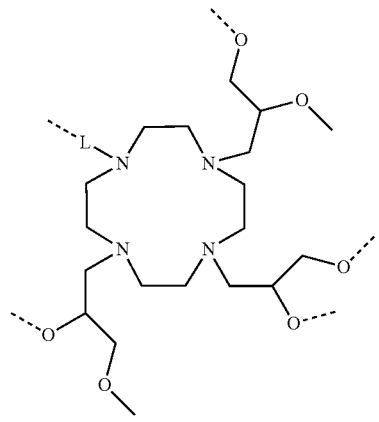

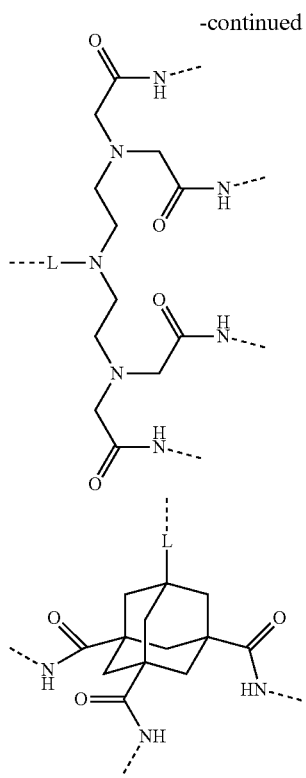

19. Conjugate according to embodiment 4, wherein said dendrimer D has a structure consisting of said central dendrimer core unit (CDCU) and m shells of repeating units of monomers RUx, with x running from 1 to p, wherein in each shell the repeating units are identical, and wherein the repeating units for shells RU1 to RUp are independently selected from 1,2-substituted glycerol, 1,3-substituted glycerol, pentaerythritol, glucose, mannose, galactose, lysine, tris(hydroxymethyl)aminomethane, tris(propionic acid)aminomethane, 1,1'-bis(hydroxymethyl)-propionic acid, succinic acid, glutaric acid, maleic acid, glycolic acid, diglycolic acid, adipic acid, lactic acid, citric acid, propionic acid (2-aminoethyl)amide, propyleneimine, ethyleneimine, propyleneoxide, ethyleneoxide, particularly 1,2-substituted glycerol, 1,3-substituted glycerol propyleneoxide, and ethyleneoxide, and wherein the number of repeating units per shell x is identical to the number of free functional groups in the shell (x-1), and wherein all free functional groups of the shell RUp are sulfated.

20. The conjugate of embodiment 19, wherein the repeating units RUp are identical in all shells.

21. The conjugate of any one of embodiment 1 to 15, wherein E is directed against a target molecule localized within a target cell, preferably within the cytosol of a target cells, particularly wherein said target cell is a tumor cell.

22. The conjugate of embodiment 21 wherein said target molecule is selected from Fox01, HDAC, DP-1, E2F, ABL, AMPK, BRK, BRSK1, BRSK2, BTK, CAMKK1, CAMKK alpha, CAMKK beta, Rb, Suv39H1, SCF, p19INK4D, GSK-3, p18 INK4, myc, cyclin E, CDK2, CDK9, CDG4/6, Cycline D, p16 INK4A, cdc25A, BMI1, SCF, Akt, CHK1/2, CK1 delta, CK1 gamma, CK2, CLK2, CSK, DDR2, DYRK1A/2/3, EF2K, EPH-A2/A4/B1/B2/B3/B4, EIF2AK3, Smad2, Smad3, Smad4, Smad7, p53, p21 Cip1, PAX, Fyn, CAS, C3G, SOS, Tal, Raptor, RACK-1, CRK, Rap1, Rac, KRas, NRas, HRas, GRB2, FAK, PI3K, spred, Spry, mTOR, MPK, LKB1, PAK1/2/4/5/6, PDGFRA, PYK2, Src, SRPK1, PLC, PKC, c-Raf, PKA, PKB alpha/beta, PKC alpha/gamma/zeta, PKD, PLK1, PRAK, PRK2, RIPK2, B-Raf, WAVE-2, TSC2, DAPK1, BAD, IMP, C-TAK1, TAK1, TAO1, TBK1, TESK1, TGFBR1, TIE2, TLK1, TrkA, TSSK1, TTBK1/2, TTK, Tpl2/cot1, MEK1, MEK2, PLD1, Erk1, Erk2, Erk5, Erk8, p90RSK, PEA-15, SRF, p27 KIP1, TIF1a, HMGN1, ER81, MKP-3, c-Fos, FGF-R1, GCK, GSK3 beta, HER4, HIPK1/2/3/, IGF-1R, cdc25, UBF, LAMTOR2, Stat1, Stat3, CREB, JAK, Src, PTEN, NF-kappaB, HECTH9, Bax, HSP70, HSP90, Apaf-1, Cyto c, BCL-2, Bcl-xL, Smac, XIAP, Caspase-9, Caspase-3, Caspase-6, Caspase-7, CDC37, TAB, IKK, TRADD, TRAF2, RIP1, FLIP, TAK1, JNK1/2/3, Lck, A-Raf, B-Raf, C-Raf, MOS, MLK1/3, MNK1/2, MSK1, MST2/3/4, MPSK1, MEKK1, MEKK4, MELK, ASK1, MINK1, MKK1/2/3/4/6/7, NEK2a/6/7, NUAK1, OSR1, SAPK, STK33, Syk, Lyn, PDK1, PHK, PIM1/2/3, Ataxin-1, mTORC1, MDM2, p21Waf1, Cyclin D1, Lamin A, Tpl2, Myc, catenin, Wnt, IKK-beta, IKK-gamma, IKK-alpha, IKK-epsilon, ELK, p65RelA, IRAK1, IRAK2, IRAK4, IRR, FADD, TRAF6, TRAF3, MKK3, MKK6, ROCK2, RSK1/2, SGK1, SmMLCK, SIK2/3, ULK1/2, VEGFR1, WNK1, YES1, ZAP70, MAP4K3, MAP4K5, MAPK1b, MAPKAP-K2/K3, p38 alpha/beta/delta/gamma MAPK, Aurora A, Aurora B, Aurora C, MCAK, Clip, MAPKAPK, FAK, MARK1/2/3/4, Muc1, SHC, CXCR4, Gap Definitions In chemistry, a conjugate refers to a compound formed by the joining of two or more chemical compounds. As used in the description of the invention and in the claims, the term "conjugate" particularly has the meaning of a linked group of compounds having the elements of the formula E-[G-L-D(OSO$_3^-$M$^+$)$_n$]$_m$, in particular the effector molecule E, the connecting functional group G, linker L, dendrimer D, and the n sulfate groups (OSO$_3^-$M$^+$), wherein M is a cationic inorganic or organic counter ion, wherein m is an integer from 1 to 20.

The term "dendrimer" D as used herein generally denotes repetitively branched molecules, wherein a dendrimer is typically symmetric around the core, and often adopts a spherical three-dimensional morphology. Dendritic molecules are characterized by structural perfection. Dendrimers are monodisperse and usually highly symmetric, spherical compounds. The field of dendritic molecules can be roughly divided into low-molecular weight and high-molecular weight species. The first category includes dendrimers and dendrons, and the latter includes dendronized polymers, hyperbranched polymers, and the polymer brush.

The properties of dendrimers are dominated by the functional groups on the molecular surface, however, there are examples of dendrimers with internal functionality. Dendritic encapsulation of functional molecules allows for the isolation of the active site, a structure that mimics that of active sites in biomaterials. Also, it is possible to make dendrimers water soluble, unlike most polymers, by functionalizing their outer shell with charged species or other groups. Other controllable properties of dendrimers include toxicity, crystallinity, tecto-dendrimer formation, and chirality.

D is a dendrimer or dendritic structure which is structurally defined with respect to its molecular weight, being a chemical structure with a single molecular weight.

D(OSO$_3^-$M$^+$)$_n$ means that the dendrimer D is highly sulfated carrying a number n of sulfate groups (OSO$_3^-$M$^+$). The sulfate groups are preferably derived from hydroxyl groups which are converted into sulfate groups (monoesters of sulfonic acid) by a sulfation process (see also examples). Accordingly, the dendrimers comprise a certain number of sulfate groups derived from OH groups. These OH groups are preferably located on the surface or outer shell of the dendrimer and are part of the building blocks used to constitute the dendritic polyol structure.

Dendrimer D consists of repeating units of monomers to built the dendritic structure comprising structures such as 1,2-substituted glycerol, 1,3-substituted glycerol, pentaerythritol, lysine, tris(hydroxymethyl)aminomethane. Also, alkyl-carboxylic acid-containing or alkyl-biscarboxylic acid structures, such as tris(propionic acid)aminomethane, 1,1'-bis(hydroxymethyl)-propionic acid, succinic acid, glutaric acid, maleic acid, glycolic acid, diglycolic acid, adipic acid, lactic acid, citric acid, propionic acid (2-aminoethyl)amide, as well as alkylamino structures, such as propyleneimine, ethyleneimine, and amino acid building blocks are part of the embodiment. Furthermore, monosaccharide structures, such as glucose, mannose, galactose are possible repeating units in dendrimers. Representative but not-limiting examples are depicted in FIGS. 1 to 7. Preferred dendrimers contain 1,2-substituted glycerol and/or 1,3-substituted glycerol. More preferred dendrimers contain 1,2-substituted glycerol and/or 1,3-substituted glycerol, optionally in combination with alkylcarboxlic acid units, allowing preferably connections selected from the functional groups ester, ether and amide.

The synthesis of dendrimers is known to persons skilled in the art. The general structure of the dendrimer can be built up by a convergent synthetic pathway or a divergent synthetic pathway (Tomalia, WO2006/115547; Medina et al., Chem. Rev. 2009, 109, 3141; Crespo et al., Chem. Rev. 2005, 105, 1663). A preferred embodiment of the synthesis is a synthetic pathway, wherein a core unit (as described above) is modified such that a linker unit or functional group for further prolongation with a further linker unit is established. The dendrimer is then built up divergent by adding further shells starting from the core unit. Thus, the linker attached to the core unit is at the central position as a focal point. A combination with convergent synthetic pathways can be followed by adding a further dendrimer unit which has been previously built up by either divergent or convergent pathways to the core unit or shells, thereby creating a further shell. Also, a convergently synthesized dendrimer with focal linker attachment can then be further modified by a divergent addition of further shells. The embodiment is supported by examples (1-11) of synthesis.

The connection of monomers in the dendrimer is based on functional groups selected from ether, thioether, carboxylic ester, sulfonylester, sulfonamide, carboxylamide, amine, carbamate, thiocarbamate, urea, thiourea, hydrazone, imine, disulfide, phosphate, phosphonate, triazole. Hence, the dendrimer consists of repetitive subunits or shells based on different monomeric units, including but not limited to the examples described herein (FIGS. 1-7). Preferred dendrimers contain 1,2-substituted glycerol and/or 1,3-substituted glycerol, optionally in combination with alkylcarboxlic acid units, allowing preferably connections selected from the functional groups ester, ether and amide.

The term dendrimer is used through the embodiments, which is commonly understood as tree-like, branched structure. The term dendron usually describes a dendrimer with a single chemically addressable group called the focal point, but the terms are typically used interchangeably.

The dendrimer D is composed in a fashion that a linker unit L is covalently attached to it. Preferred are structures in which the linker unit L is covalently hound to a central position of the dendrimer, which is also called focal point. From this focal point, the dendrimer is grown to reach its dendritic structure. Representative but not-limiting examples are depicted in FIGS. 1 to 7, wherein the "star" illustrates the connection of the linker L to the focal point of the dendrimer.

A "linker" or "spacer" in accordance with the invention denotes a chemical structure which crosslinks two chemical molecules by forming one covalent bond to the first molecule and another covalent bond to the second molecule. A linker usually comprises two reactive groups, which can be identical (homobifunctional linker) or different (heterobifunctional linker). In the context of the present invention, the sulfated dendrimer D is the first molecule and the linker forms a covalent bond with the focal point in the dendrimer. The therapeutic effector molecule E is the second molecule with a covalent bond formed by the structure G. The term "spacer" is often used similarly, more with the intention to describe that with this structure a certain distance ("space") between the two linked molecules is generated.

In accordance with the invention, a "conjugate" is a molecule which consists two or more different types of molecules which are covalently linked to each other by a linker or spacer, thereby forming a conjugate.

The term "terminal group" in the context of a chemical structure of dendrimer D describes the monomer units of the outer shell, which is the monomer to which no further monomer unit is attached. Most of the chemical properties of the molecule depend on types of terminal groups. The physical properties of the molecules, such as solubility and viscosity are also affected by the terminal groups. Accordingly, the terminal groups within the scope of the present invention provide sulfate groups derived from hydroxyl groups. These sulfate groups determine the biological properties of the inventive dendrimer conjugates with effector molecules, as outlined above.

Counter ion $M^+$ comprise organic and inorganic cations. Organic cations comprise lysine, meglumine, TRIS, glycine or other amines derived from amino acids. Inorganic cations comprise potassium, sodium, lithium, or mixtures thereof. Preferred is sodium leading to $—SO_3^-Na^+$ groups.

The term "antibody" is well known in the art. As used herein, it denotes an immunoglobulin or any functional fragment thereof. It encompasses any polypeptide that has an antigen-binding site. It includes, but is not limited to, monoclonal, polyclonal, monospecific, polyspecific, non-specific, humanized, human, single-chain, chimeric, synthetic, recombinant, hybrid, mutated, grafted, and in vitro generated antibodies. The term "antibody" encompasses antibody fragments as well such as Fab, F(ab')2, Fv, scFv, Fd, dAb, and any other antibody fragments that retain antigen-binding function. Typically, such fragments would comprise an antigen-binding domain. The term "antibody" as defined above is preferably characterized by an binding constant of at least $10^{-7}$-$10^{-10}$ M in accordance with the invention. Further, an "antibody" is a protein that is produced as a reaction to an antigen stimulus and specifically recognizes and binds the antigen producing the stimulus.

As used herein, the term "antibody mimetics" are organic compounds that, like antibodies, can specifically bind antigens, but that are not structurally related to antibodies. They are usually artificial peptides or proteins with a molar mass of about 3 to 20 kDa. Nucleic acids and small molecules are sometimes considered antibody mimetics as well, but not artificial antibodies, antibody fragments and fusion proteins composed from these. Some types have an antibody-like beta-sheet structure. Common advantages over antibodies are better solubility, tissue penetration, stability towards heat and enzymes, and comparatively low production costs. Antibody mimetics are being developed as therapeutic and diagnostic agents. The term "scaffolds" as used above falls under the term "antibody mimetics". As used herein, the term "effector" refers to an effector molecule that can act as a therapeutic or diagnostic effector molecule. A therapeutic effector molecule is usually a molecule that selectively binds to a protein and regulates its biological activity. In this manner, therapeutic effector molecules act as ligands that can increase or decrease enzyme activity, gene expression, or cell signalling. Effector molecules can also directly regulate the activity of some mRNA molecules (riboswitches). In the context of the present invention, polypeptides, including proteins and antibodies as described above, are considered to function as therapeutic effector molecules, especially in cellular signal transduction cascades.

The term diagnostic effector molecule refers to molecules which upon the above mentioned biological interactions provide a detectable or recordable signal permitting quantification or monitoring the presence of this molecule in the target cell. This signal can be measured by analytical, chemical or physical techniques, such as ELISA, immunoassays, diagnostic imaging, including the detection of fluorescence, radioactive emission, or magnetic relaxation. In particular, effector molecules can be labeled with detectable molecules selected from fluorescent dyes, radioactive isotopes, paramagnetic metals.

The term "transport protein" encompasses different tell is including transmembrane pump, transporter protein, escort protein, acid transport protein, cation transport protein, or anion transport protein. Accordingly, it is a protein that moves other materials within an organism. Different kinds of transport proteins are known according to their function. These include carrier proteins involved in the movement of ions, small molecules, or macromolecules, such as another protein or a virus, across a biological membrane. Carrier proteins are membrane proteins which means they exist within a membrane across which they transport substances. They also called transmembrane solute carrier proteins assisting in the passive or active transport, also called carrier-mediated transport.

FIGURE DESCRIPTION

FIG. 1 depicts exemplary chemical structures of sulfated dendrimers in accordance with the invention.

FIG. 1A: core derivable e.g. from pentaerythritol or TRIS, dendrimer units: glycerol, 1,2-substituted, connected as ether (—O—), 24 sulfate groups, FIG. 1B: core derivable e.g. from glycerol or 2-aminopropane-1,3-diol, dendrimer units: glycerol, 1,3-substituted, connected as ether (—O—), 32 sulfate groups (sulfate group illustrated as S in bulb, star indicates connection to linker L).

FIG. 2 depicts exemplary chemical structures of sulfated dendrimers in accordance with the invention.

FIG. 2A: core derivable e.g. from pentaerythritol or TRIS, dendrimer units: pentaerythritol and glycerol, 1,2-substituted, connected as ether (—O—), 36 sulfate groups, FIG. 2B: core 2,2-bis(hydroxymethyl)propionic acid, dendrimer units: 2,2-bis(hydroxymethyl)propionic acid, connected as ester, and glycerol, 1,2-substituted, connected as ether (—O—), 32 sulfate groups.

FIG. 3 depicts exemplary chemical structures of sulfated dendrimers in accordance with the invention.

FIG. 3A: core derivable e.g. from aminomethyl-tris(propionic acid) or hydroxymethyl-tris(propionic acid connected as amide, dendrimer units: glycerol, 1,2-substituted and glycerol 1,3-substituted, connected as ether (—O—), 24 sulfate groups, FIG. 3B: core derivable e.g. pentaerythritol or TRIS, dendrimer units: propionic acid connected as amide, glycerol 1,3-substituted and glycerol 1,3-substituted, connected as ether (—O—), 24 sulfate groups.

FIG. 4 depicts exemplary chemical structures of sulfated dendrimers in accordance with the invention.

FIG. 4A: core derivable e.g. from tris(propionic acid) methylamine, dendrimer units: pentaerythritol, connection as ester, glycerol, 1,2-substituted connected as ether, 36 sulfate groups, FIG. 4B: core derivable e.g. from tris(propionic acid) methylamine, dendrimer units: bis(propionic acid)ethylene diamine, connection as amide, triglycerolamine connected as amide, 32 sulfate groups.

FIG. 5 depicts exemplary chemical structures of sulfated dendrimers in accordance with the invention.

FIG. 5A: core derivable e.g. from glycerol or 2-aminopropane-1,3-diol, dendrimer units: glycerol, 1,3-substituted, connected as ether (—O—), succinic acid, connected as ester, 32 sulfate groups, FIG. 5B: core derivable e.g. from tris(propionic acid) methylamine, dendrimer units: glycerol, 1,3-substituted, succinic acid; 24 sulfate groups.

FIG. 6 depicts exemplary chemical structures of sulfated dendrimers based on sugar moieties in accordance with the invention.

FIG. 6A: core based on monofunctionalized cyclodextrin (here β-cyclodextrin): dendrimers units: glycerol, 1,2-substituted, connected as ether (—O—), 40 sulfate groups, FIG. 6B: core derivable from e.g. pentaerythritol or TRIS, dendrimer units: propionic acid connected as amide, bis (glucamine) connected as amide, 30 sulfate groups.

FIG. 7 depicts exemplary chemical structure of sulfated dendrimer: core derivable e.g. from pentaerythritol or TRIS; ethylene oxide units, connected via ether bond to pentaerythritol; dendrimer units at pentaerythritol: glycerol, 1,2-substituted, connected via ether; 36 sulfate groups in accordance with the invention FIG. 8 illustrates cellular uptake of dendrimer conjugates (Example 15) in accordance with the invention.

EXAMPLES

Figure 1:
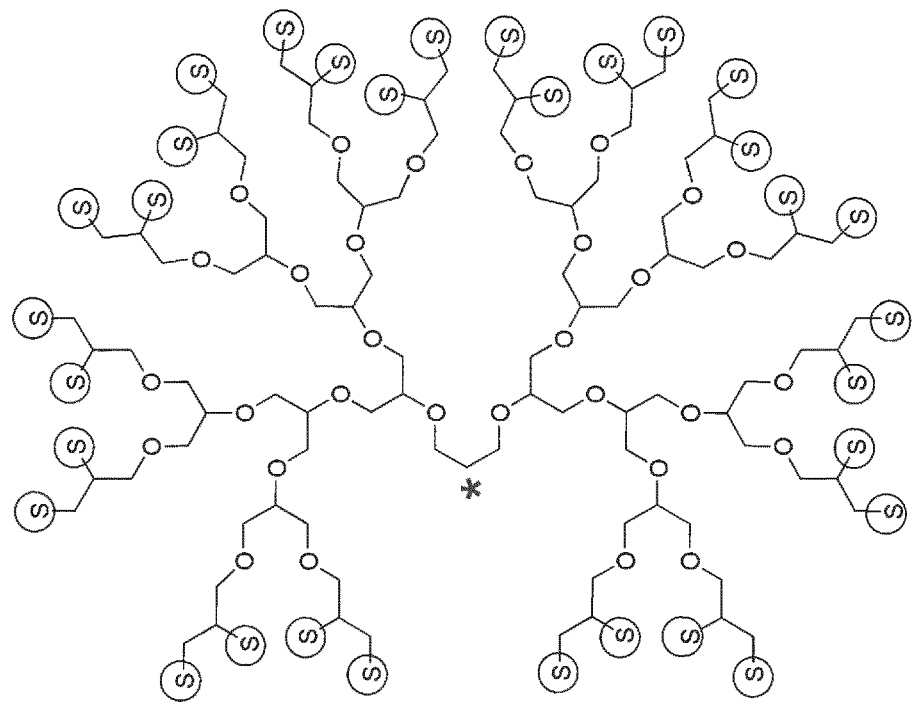
Figure 1:
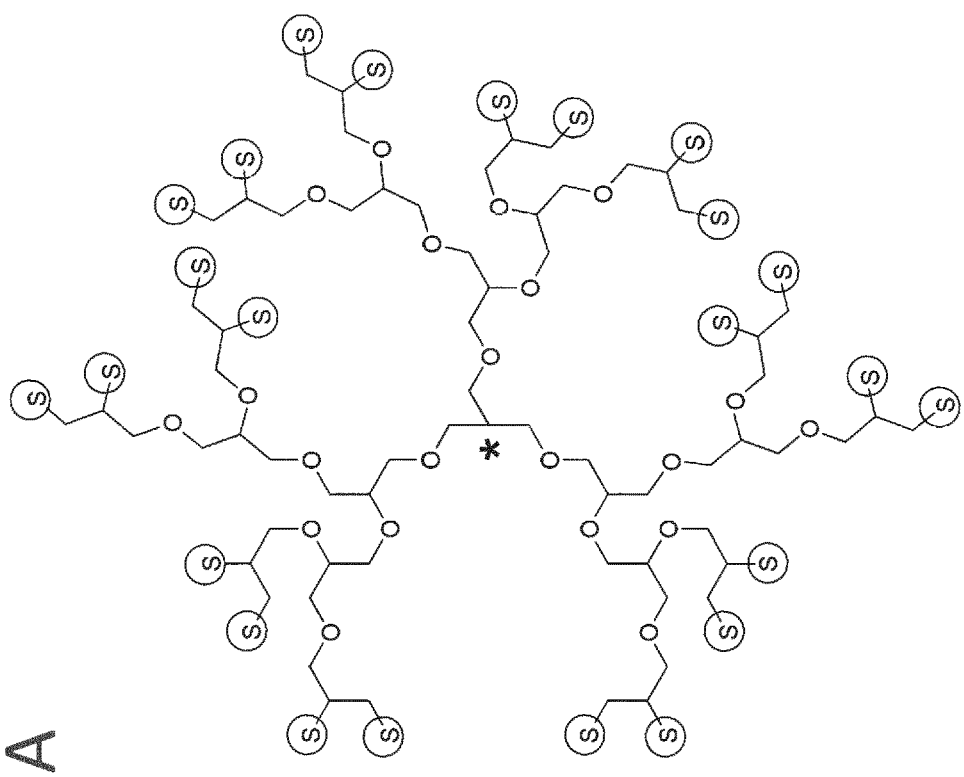
Figure 2:
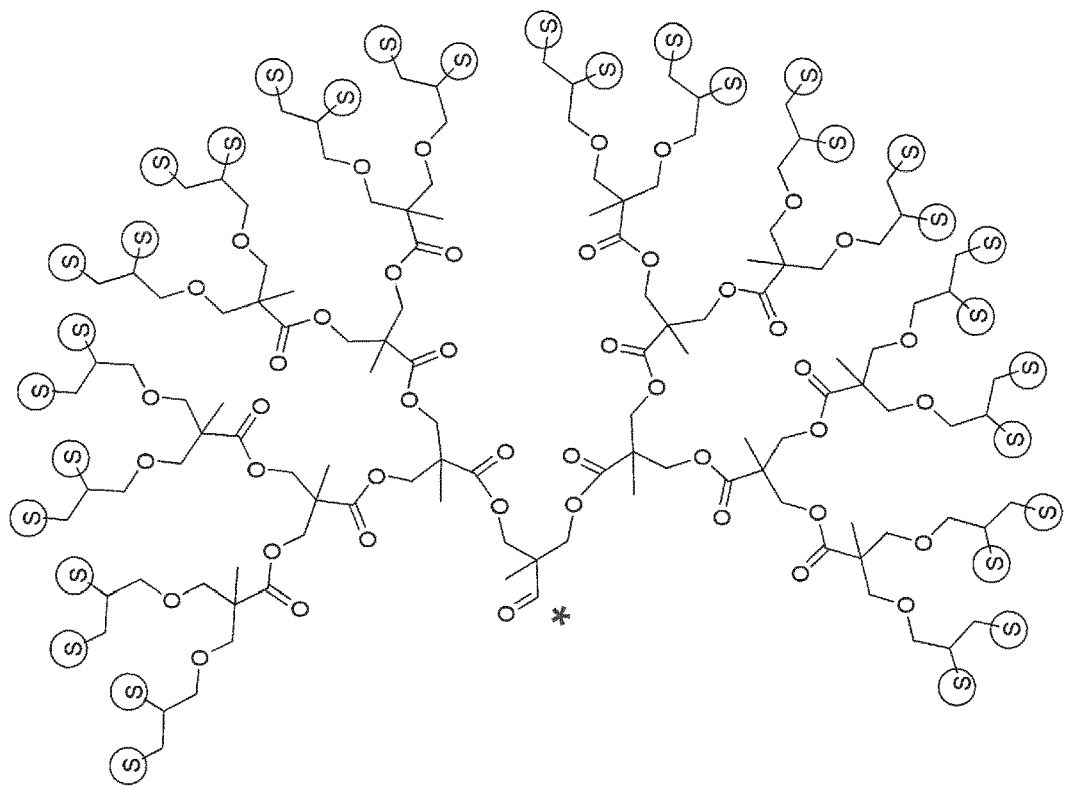
Figure 2:
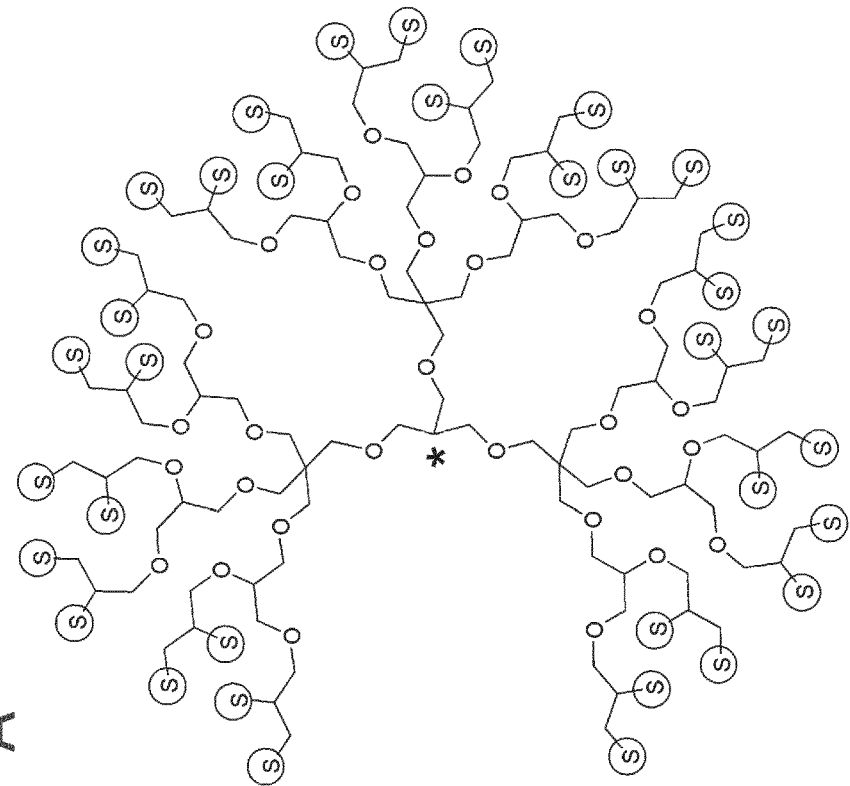
Figure 3:
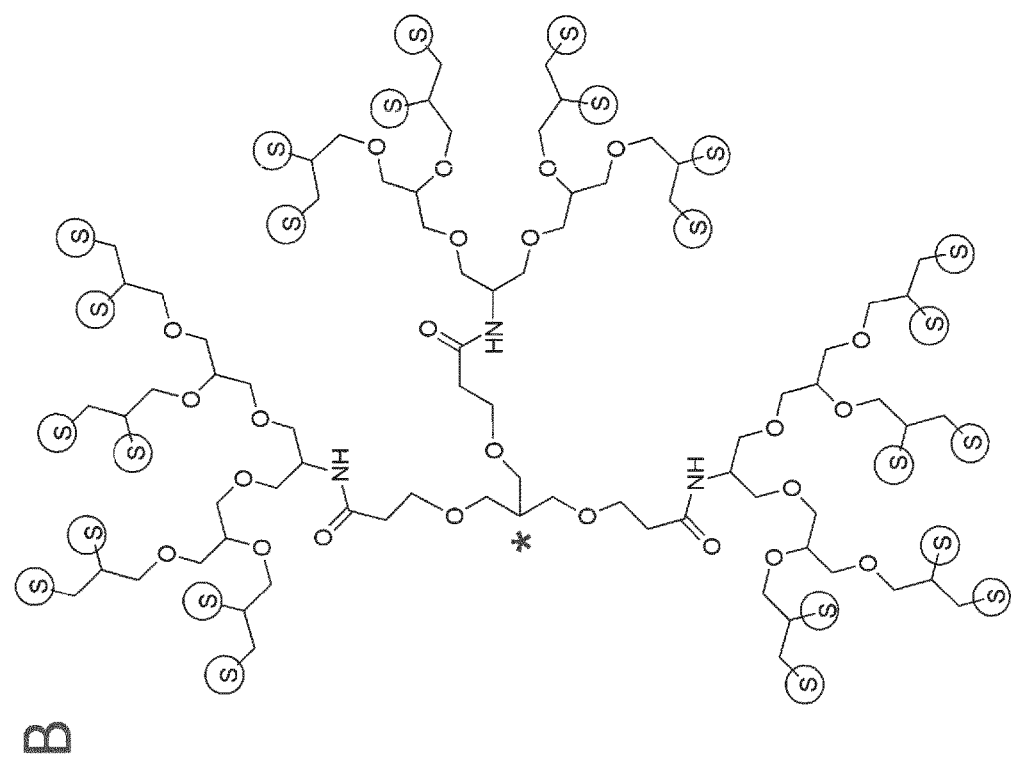
Figure 3:
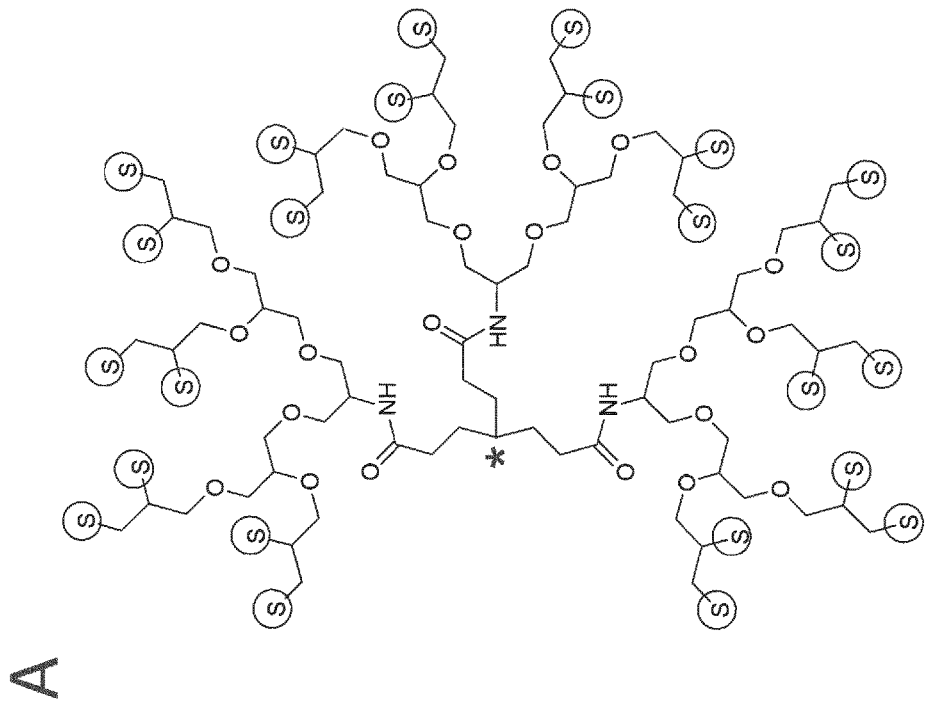
Figure 4:
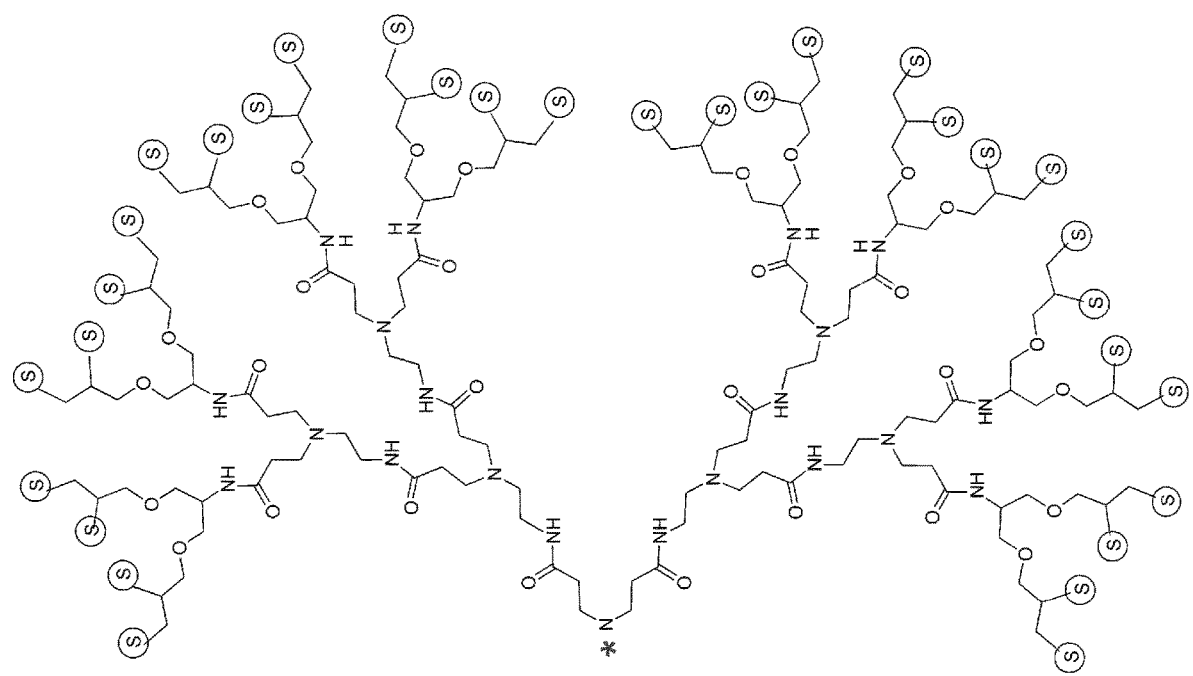
Figure 4:
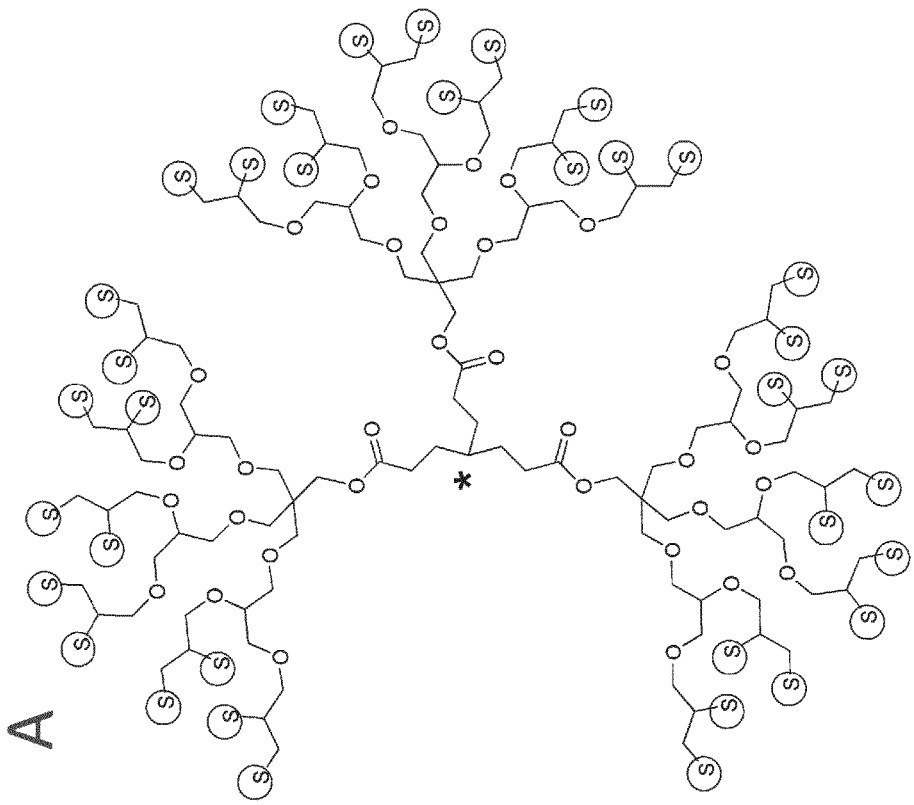
Figure 5:
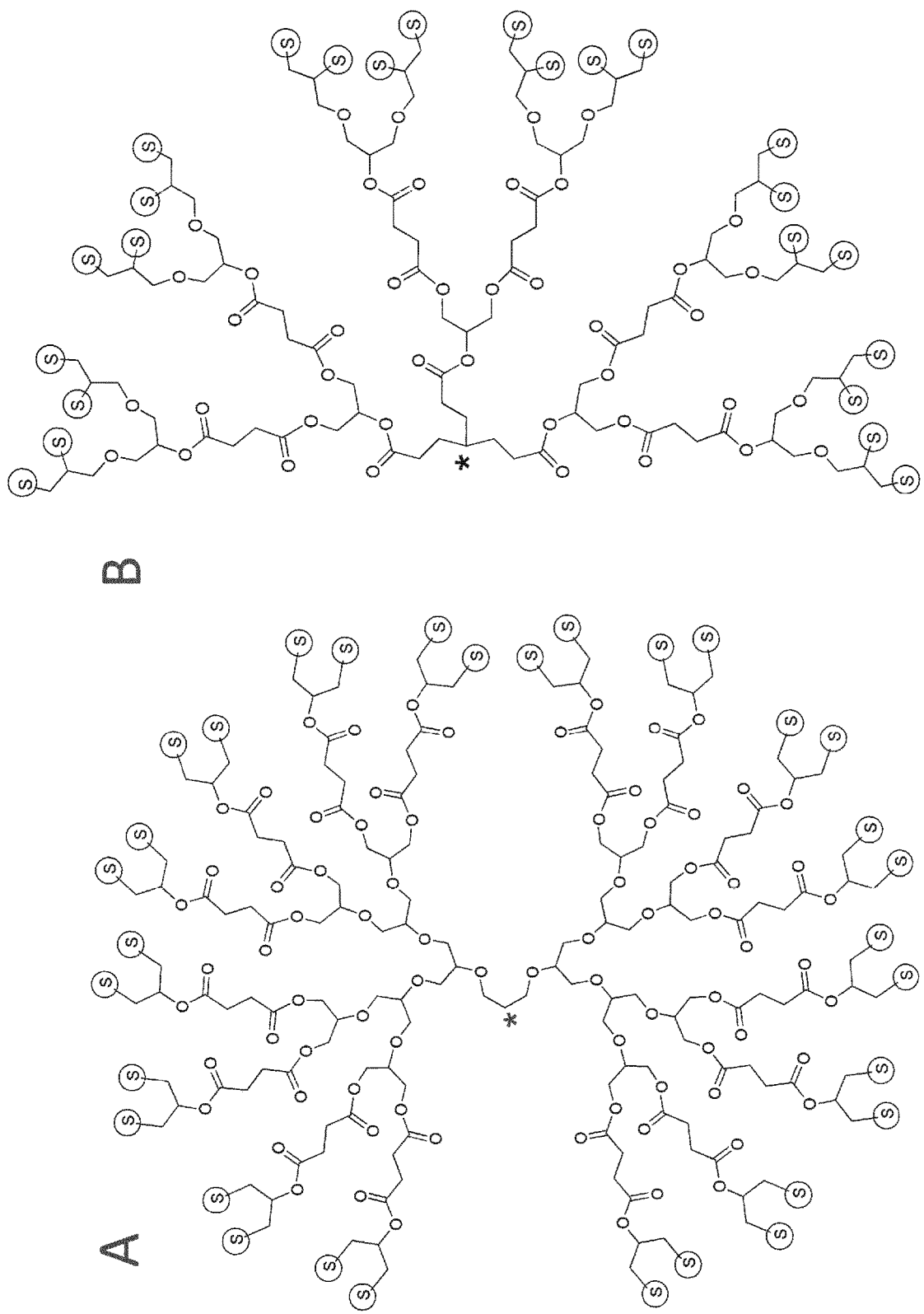
Figure 6:
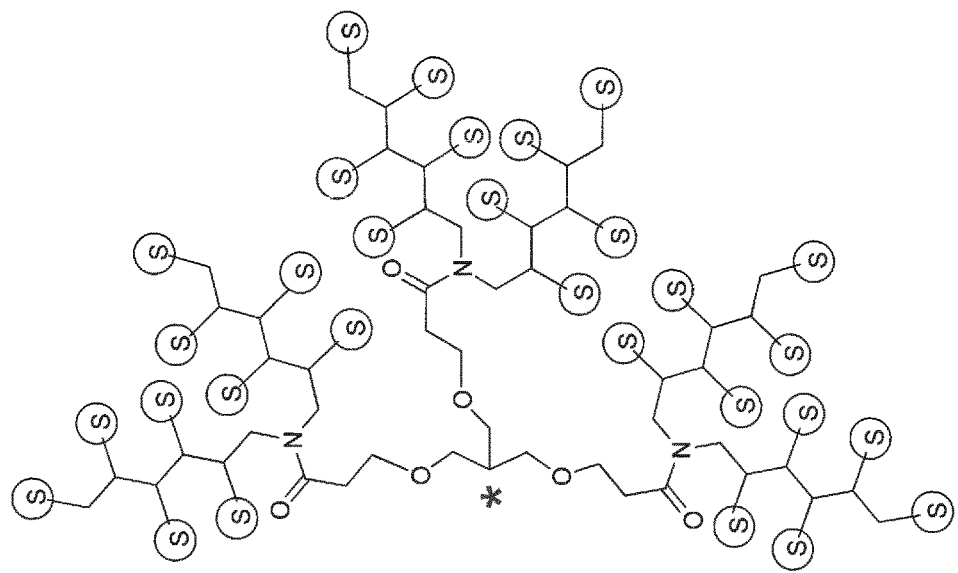
Figure 6:
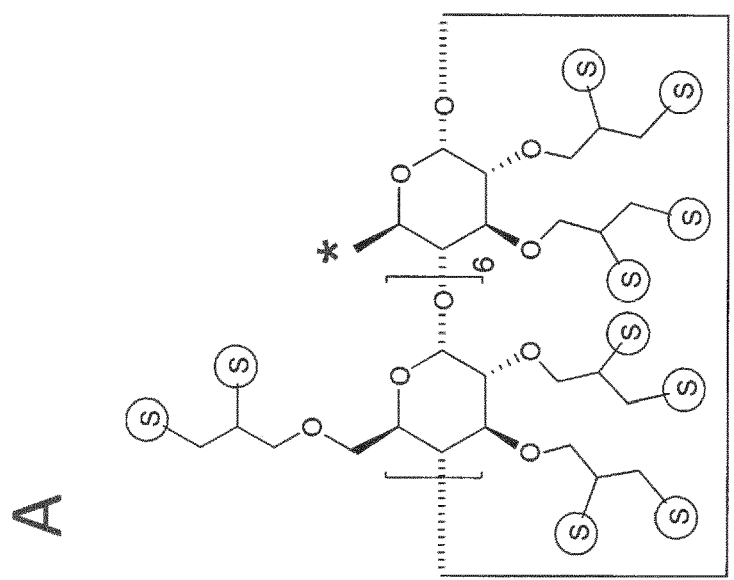
Figure 7:
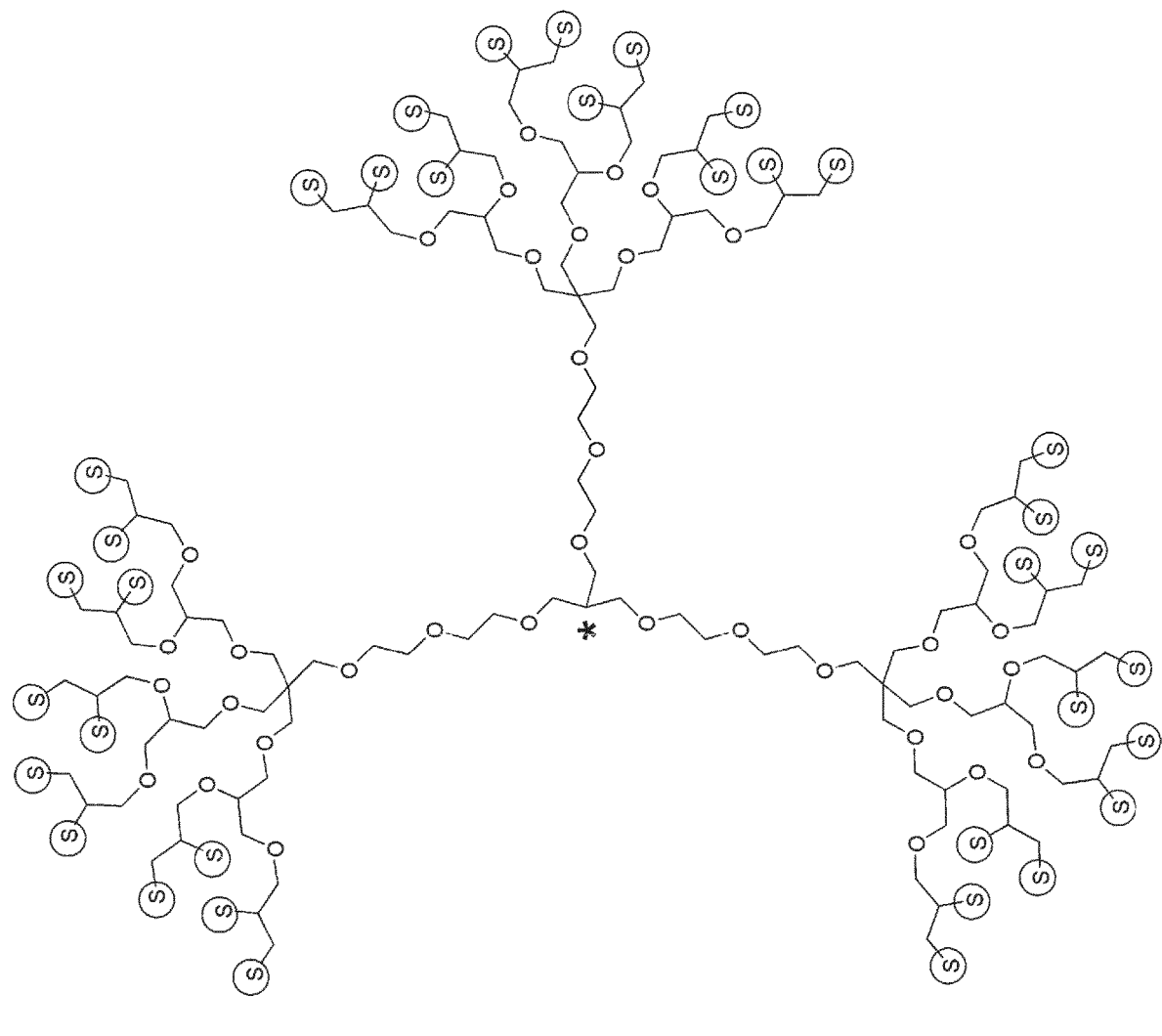

The following examples can be repeated with similar success by substituting the generically or specifically described reactants and/or operating conditions of this invention. It is believed than one skilled in the art can easily ascertain the essential characteristics of this invention and understands the Examples of the invention as exemplary. Thus the below examples are not limiting the subject-matter of the invention.

Example 1

Synthesis of Polyglycerol Dendrimer System with 24 Sulfate Groups and aminodecyl Linker (Compound d01)

Example 1a

Synthesis of 10-azidodecyl-triallylpentaerythritol

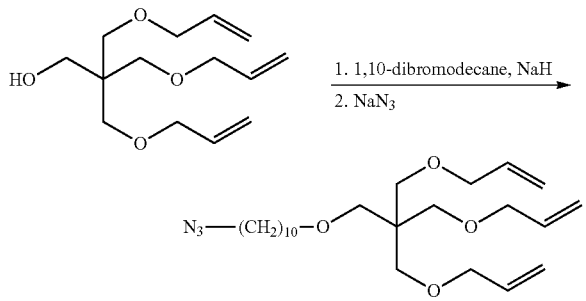

To a solution of triallylpentaerythritol (5 g, 19.5 mmol) in 50 mL of dry THF, solid NaH (3.9 g, 98 mmol, 60% dispersion in mineral oil). is added portionwise. The mixture is stirred at 40° C. for 3 h, followed by the addition of 0.3 g potassium iodide and a solution of 1,10-dibromodecane (29.3 g, 98 mmol) in 20 mL THF. After 24 h at reflux, the mixture is treated with water, evaporated to dryness, and the residue dissolved in water/dichloromethane. The product is extracted into dichloromethane, dried over $Na_2SO_4$, and purified by silica chromatography (cyclohexane/ethylacetate) yielding 8.1 g intermediate 10-bromodecyl-triallyl-pentaerythritol. 8 g (16.8 mmol) of the intermediate is dissolved in DMF (50 mL) and sodium azide (5.6 g, 84 mmol) is added. The mixture is stirred at 80° C. for 24 h, followed by filtration and evaporation of the solvent. Chromatographic purification (cyclohexane, then dichloromethane: methanol 95:5 to 1:1) yielded 4.0 g (55%) product as slightly yellow oil.

Example 1b

Synthesis of 10-azidodecyl-tris(2,3-dihydroxypropyl)pentaerythritol

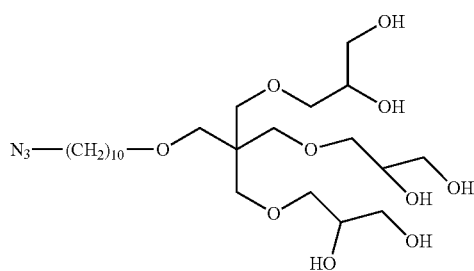

The reaction is conducted according Zieringer et al., ChemPhysChem. 2010, 11, 2617. 10-azidodecyl-triallylpentaerythritol (4.0 g, 9.1 mmol) is dissolved in 300 mL of a mixture of t-butanol/water (1:1). To this mixture trimethylamine-N-oxide dihydrate (9.1 g, 82.4 mmol), citric acid (10.0 g, 47.7 mmol) and potassium osmate dihydrate (0.4 g, 1.1 mmol) is added, followed by stirring at room temp. for 24 h. Ion exchange resin Lewatit K6267 (70 g) is added and the mixture allowed to stir another 1 h. After filtration and washing with t-butanol/water 1:1, the solution is evaporated to dryness and the residue purified by chromatography (RP C-18 Licroprep) using water/methanol in an MPLC system. Yield 3.5 g (71%) of a colorless viscous oil.

Example 1c

Dendrimer Generation from 10-azidodecyl-tris(2,3-dihydroxypropyl)pentaerythritol The dendrimer is built of a dendron consisting of glycerol monomers (1,2-subst. pattern) employing 24 hydroxy groups by published methods (Zieringer et al., Chem. Phys. Chem. 2010, 11, 2617 and Wyszogrodska et al., Eur. J. Org. Chem. 2008, 53) in 4 reaction steps of alternating allylation with NaH/allybromide and dihydroxylation. The product is 10-azidodecyl-glycerol $(OH_{24})$, molecular weight 1873 g/mol, which is sulfated in the next step.

Example 1d

Sulfation of 10-azidodecyl dendron$(OH)_{24}$ 100 mg (0.053 mmol) 10-azidodecyl dendron$(OH_{24})$ is dissolved in 0.5 mL dry DMF and heated to 60° C. Under stirring, $SO_3$-pyridine complex (245 mg, 1.54 mmol) is added, followed by 5 h stirring at 60° C. and 18 h at room temp. The reaction mixture is quenched with water, adjusted to pH 9-10 using 1 mM NaOH, filtrated and subjected to ultrafiltration (MWCO 1000) with water. The product 10-azidodecyl dendron$(OSO_3^-Na^+)_{24}$ (150 mg, 65%) is obtained after lyophilisation. Elementary analysis revealed complete sulfation. N, 0.863, C, 21.70, S, 17.83, H, 3.042, molecular weight 4322 g/mol.

Example 1e

Synthesis of 10-aminodecyl dendron$(OSO_3^-Na^+)_{24}$ (Compound d01)

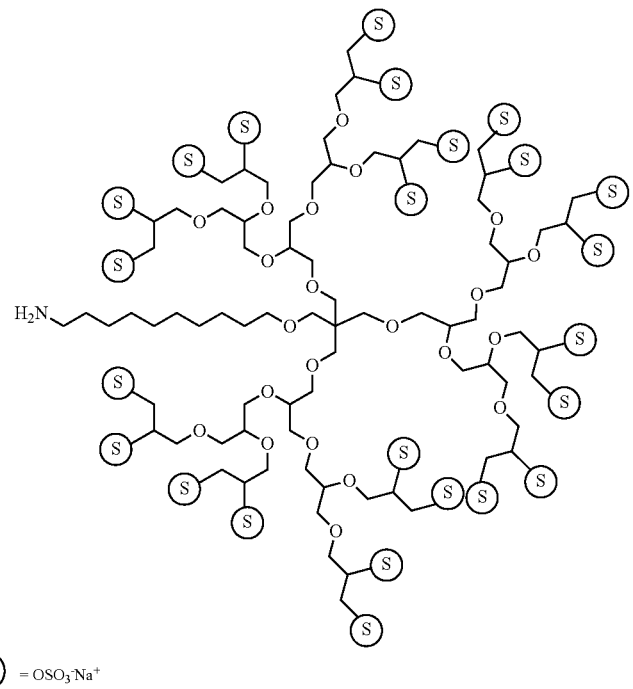

$\text{S}$ = $OSO_3^-Na^+$

To a solution of 10-azidodecyldendron(OSO$_3^-$Na$^+$)$_{24}$ (150 mg, 0.035 mmol) in water/methanol 1:1 (2 mL) TCEP (60 mg, 0.2 mmol) is added and the mixture is stirred at room temp. for 18 h. After evaporation, the residue is dialysed against 20% NaCl and dest. water (reg. cellulose, MWCO 1000), yield 107 mg (72%) of compound d01 after lyophilisation (molecular weight 4296 g/mol).

The example can also be extended to alkane substituents beyond decane, including e.g. the use of 1,6-dibromohexane, 1,8-dibromooctane, 1,11-dibromoundecane, or further dibromo-alkanes employing unsaturated, cyclic or substituted moieties according to the description of the linker L in the general formula E-[G-L-D(OSO$_3^-$M$^+$)$_n$]$_m$. Furthermore, the linker can be introduced by a PEG-alkane moiety, such as azido-PEG-alkylbromide/iodide (or mesylate, tosylate), such as azido-PEG$_{3-10}$-(CH$_2$)$_{2-18}$—Br.

Example 2

Synthesis of Polyglycerol Dendrimer System with 24 Sulfate Groups and Reactive Groups for Bioconjugation from d01 by Reaction with Bifunctional PEG-COOH NHS Esters Example 2a Synthesis of Polyglycerol Dendrimer System with 24 Sulfate Groups and Maleimido Reactive Group (Compound d02) from d01 by Reaction with Maleimido-PEG(4)-COOH NHS ester 10 mg (2.33 μmol) of compound d01 is dissolved in 1 mL DMF/water 9:1 and maleimido-PEG(4)-COOH NHS ester (3.0 mg, 5.83 μmol) is added, followed by shaking at 40° C. for 48 h. The product (compound d02) is precipitated by addition of dichloromethane, centrifugation and repeated washing with dichloromethane, followed by lyophilisation from dest. water. The degree of coupling is determined by H-NMR (700 MHz) based on the ration of maleimido signals (2H, s) and aliphatic spacer (multiplets <1.5, 16 H) giving 88% degree of coupling for d02 (MW 4694 g/mol).

Examples 2b-h

The synthesis of polyglycerol dendrimer systems with 24 sulfate groups and further reactive linkers is accomplished by using different bifunctional PEG-COOH NHS esters comprising an azido, propargyl, cyclooctinyl, pyridinyldisulfide, thioacetyl, or maleimido group. The reaction with compound d01 is conducted according to example 2a (yields 70-85%). Table 1 summarizes products d03 to d09.

Example 2i

Synthesis of Polyglycerol Dendrimer System with 24 Sulfate Groups and Isothiocyanate Group for Bioconjugation (Compound d10)

The amino group can alternatively be directly converted into an isothiocyanate group. 10 mg (2.33 μmol) of compound d01 is dissolved in 0.5 mL DMF and di(2-pyridyl)-thionocarbonate (1.1 mg, 4.66 μmol) is added, followed by shaking at 40° C. for 6 h. The product d10 is isolated as described in example 2a. Conversion is monitored by FTIR (2100 cm$^{-1}$) (MW 4338 g/mol).

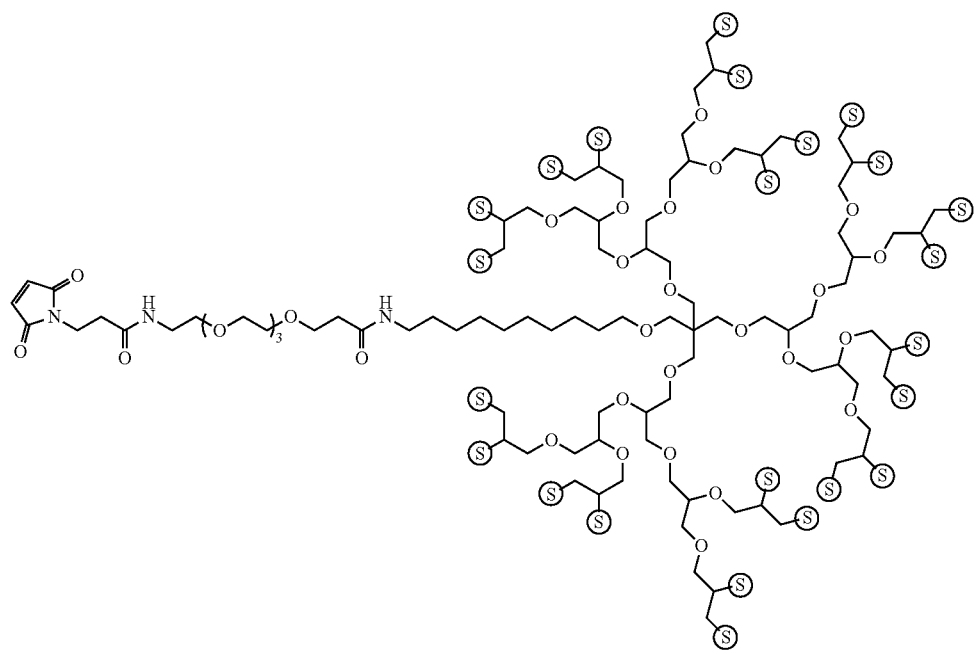

Ⓢ = OSO$_3^-$Na$^+$

TABLE 1

Reactive linkers or groups coupled to d01 and characterization of resulting product.
(dotted line indicates bond to amino group in d01 forming an amide)

| compound | Linker structure | Product MW (g/mol) | Ratio linker:dendrimer |
|---|---|---|---|
| d03 | 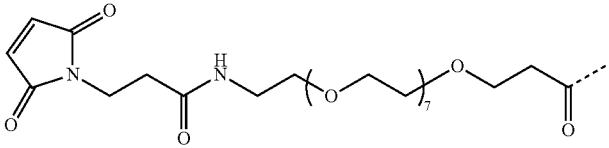 | 4870 | 78 |
| d04 | 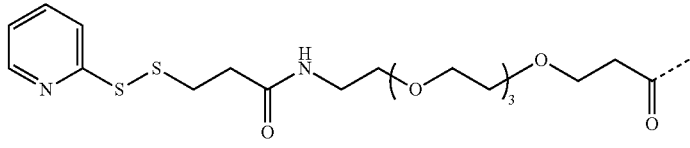 | 4741 | 89 |
| d05 | 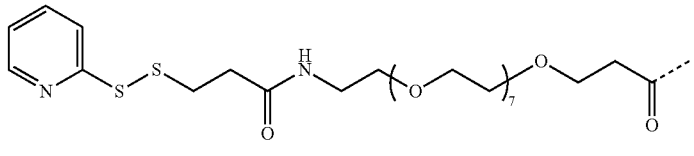 | 4917 | 68 |
| d06 | 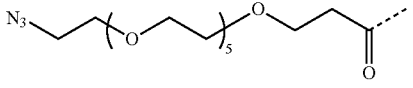 | 4657 | 95 |
| d07 | 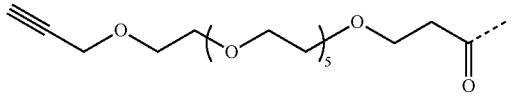 | 4670 | 95 |
| d08 | 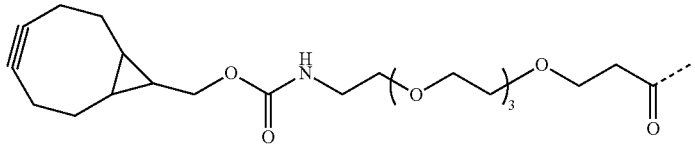 | 4719 | 90 |
| d09 | 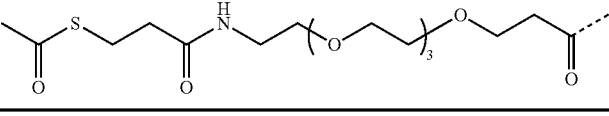 | 4673 | 87 |

The aforementioned dendrimer systems of type d01 should be understood as exemplary and are extendable to the application of other n-numbers as the specific ones here shown, e.g. by doubling the hydroxyl groups via allylation/ dihydroxylation giving 48 sulfate groups after sulfation, which give compounds in analogy to d03-d10.

Example 3

Synthesis of Polyglycerol Dendrimer System with 24 Sulfate Groups and NHS Ester Group for Bioconjugation from Example 1d (azido Linker) by Reaction with Bifunctional propargyl-PEG-COOH Linkers

Example 3a

Click Coupling of azido Dendrimer (example 1d) with propargyl-PEG(4)-carboxylic acid-t-butyl ester To a solution of 100 mg (0.023 mmol) of azido dendrimer (example 1d) in 1 mL of a mixture of water/DMF (1:1), $CuSO_4 \cdot 5H_2O$ (5.7 mg, 0.023 mmol), ascorbic acid (0.035 mmol), and (0.058 mmol) propargyl-PEG4-COO$^t$butylester (Broadphann Ltd., US) is added and the mixture is stirred at 80° C. for 18 h. The residue obtained after lyophilisation is suspended in a mixture of dichloromethane (5 mL), trifluoroacetic acid (3 mL) and water (0.1 mL), stirred for 5 h at 40° C. to obtain the free carboxylic acid group. After evaporation, the residue is suspended in MeOH and precipitated in diethylether, washed with dichloromethane, and isolated by centrifugation. The residue is dialysed against NaCl and dest. water (reg. cellulose, MWCO 1 kDa), yield 80 mg of carboxy dendrimer (MW 4582 g/mol) after lyophilisation.

Example 3b

Synthesis of polyglycerol dendrimer System with 24 Sulfate Groups and NHS ester Group for Bioconjugation (Compound d11)

To a solution of 80 mg (17.5 µmol) carboxy dendrimer (example 3a) in 2 mL DMF 6 µL (35 µmol) DIPEA is added, followed by the addition of 13 mg O—(N-succinimidyl)-N,N',N'-tetramethyl-uronium hexafluorophosphate (HSTU; 35 µmol). After 18 h stirring at room temp., the product is isolated by precipitation with dichloromethane (repeated circles of DMF/$CH_2Cl_2$), and drying in vacuum, yield 82 mg NHS ester (compound d11; MW 4679 g/mol) as amorphous solid, used without further purification.

The scope of the invention regarding polyglycerol dendrimer systems of type d11 shows that an NHS ester function can be synthesized at polysulfated dendrimers and is not limited to the example and may include other numbers n of sulfate groups, e.g. by doubling the hydroxyl groups via allylation/dihydroxylation giving 48 sulfate groups after sulfation, or other azido-alkylcarboxylic acid derivatives to synthesize NHS esters of sulfated dendrimer systems.

Example 4

Synthesis of Polyglycerol Dendrimer System with 32 Sulfate Groups and Reactive Groups for Bioconjugation (Compound d12-d17)

Example 4a

Modification of Polyglycerol Dendrimer Based on Polyglycerol Dendron [G3.0]-OH (Wyszogrodzka M. et al., Chemistry 2008, 14, 9202) with azidoundecyl Linker A solution of 0.3 g (0.21 mmol) [G3.0]-OH (16 OH groups, acetal protected) in 2 mL dry THF was reacted with 1,10-dibromodecane and subsequently with $NaN_3$ as described in example 1a followed by cleavage of acetal

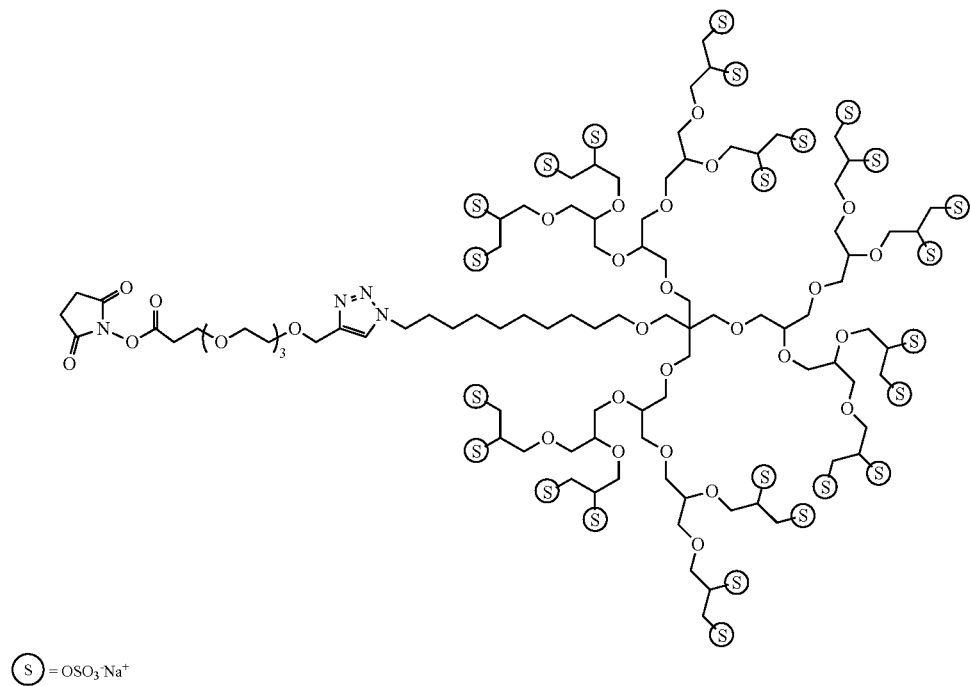

$(S) = OSO_3^-Na^+$ groups in MeOH/HCl and purification by RP C-18 chromatography (Licroprep) using water/methanol giving 0.15 g (52%) [G3.0]-O—$(CH_2)_{11}$—$N_3$ (MW 1355 g/mol).

Example 4b

Formation of Polyglycerol Dendrimer with Azidodecyl Linker (Example 4a) Through Allylation/Dihydroxylation, Sulfation and Reduction to Give Aminoundecyl-Dendrimer System with 32 Sulfate Groups (Compound d12)

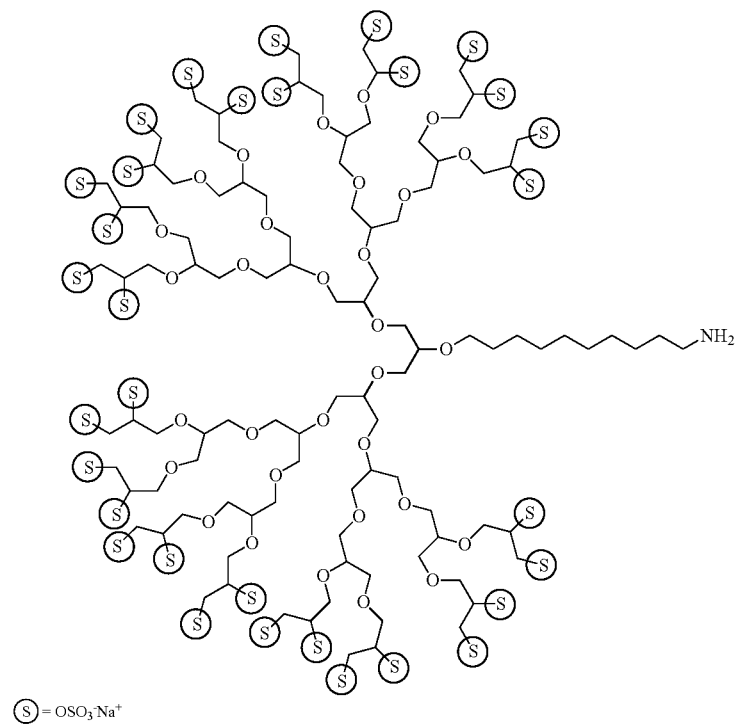

Ⓢ = OSO$_3^-$Na$^+$

The synthesis is accomplished as described in example 1d-e, giving 155 mg of product d12 as colorless amorphous solid (MW 5721 g/mol).

Example 4c-h

The synthesis of polyglycerol dendrimer systems with 24 sulfate groups and further reactive linkers is accomplished by using different bifunctional PEG-COOH NHS esters comprising an azido, propargyl, cyclooctinyl, pyridinyldisulfide, thioacetyl, or maleimido group. The reaction with compound d01 is conducted according to example 2a/4c (yields 65-86%). Table 2 summarizes achievable products d13 to d17.

TABLE 2

Reactive linkers coupled to d12 and characterization of resulting product.
(dotted line indicates bond to amino group in d12 forming amide)

| compound | Linker structure | Product MW (g/mol) | Ratio linker:dendrimer |
|---|---|---|---|
| d13 | maleimide-CH$_2$CH$_2$-C(O)-NH-CH$_2$CH$_2$-(O-CH$_2$CH$_2$)$_3$-O-CH$_2$CH$_2$-C(O)--- | 6119 | 87 |
| d14 | maleimide-CH$_2$CH$_2$-C(O)-NH-CH$_2$CH$_2$-(O-CH$_2$CH$_2$)$_7$-O-CH$_2$CH$_2$-C(O)--- | 6295 | 82 |

TABLE 2-continued

Reactive linkers coupled to d12 and characterization of resulting product.
(dotted line indicates bond to amino group in d12 forming amide)

| compound | Linker structure | Product MW (g/mol) | Ratio linker:dendrimer |
|---|---|---|---|
| d15 | pyridyl-S-S-CH2CH2-C(O)-NH-CH2CH2-(O-CH2CH2)7-O-CH2CH2-C(O)- | 6341 | 75 |
| d16 | N3-CH2CH2-(O-CH2CH2)5-O-CH2CH2-C(O)- | 6082 | 90 |
| d17 | HC≡C-CH2-O-CH2CH2-(O-CH2CH2)5-O-CH2CH2-C(O)- | 6095 | 94 |

The scope of the invention regarding polyglycerol dendrimer systems of type d12 is not limited to the Examples and may include other numbers n of sulfate groups, e.g. by doubling the hydroxyl groups via allylation/dihydroxylation giving 64 sulfate groups after sulfation, which give compounds in analogy to d13-d17.

Example 5

Synthesis of polyglycerol/amido dendrimer System with 24 Sulfate Groups and Reactive Groups for Bioconjugation based on aminomethyl-tris(Propionic Acid) and Triglycerol (Compounds d18-d22)

Example 5a

Synthesis of aminomethyl-tris(Propionic Acid)-tris(Triglycerolamide)

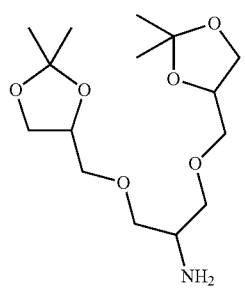

+

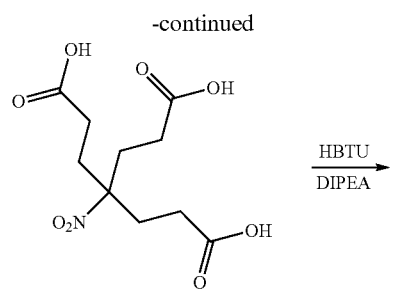

HBTU
─────→
DIPEA

[structure with O2N-C(CH2CH2C(O)NH-triglycerol)3]

H2/Pd
─────→
N4+HCO2−

-continued

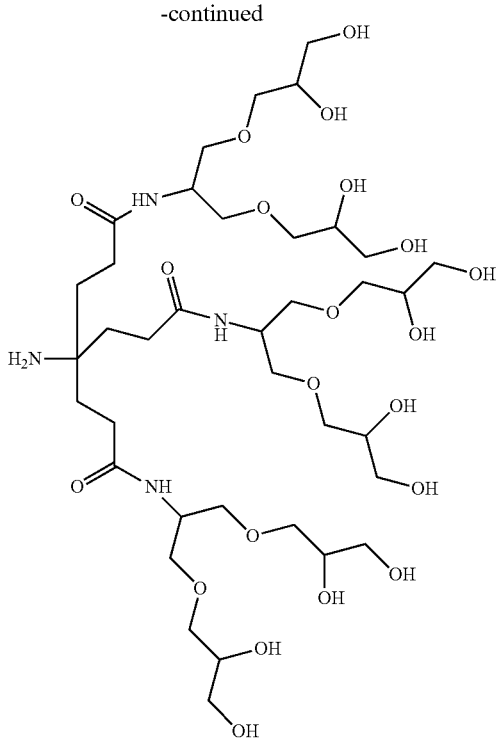

To a solution of nitromethane-trispropionic acid (1.5 g, 5.4 mmol) and DIPEA (3.9 g, 30 mmol) in 15 mL DMF, a solution of HBTU (9.3 g, 24 mmol) in 2 mL DMF is given. After 30 min stirring at room temp. a solution of (7.3 g, 23 mmol) triglycerolamine, acetal-protected (1,3-bis[2,2-dimethyl-1,3-dioxolan-4-yl)methoxy]-2-propylamine; according to Wyszogrodzka M. et al., Chemistry 2008, 14, 9202) in 2 mL DMF. is added, followed by stirring at room temp. for 24 h. The reaction mixture is evaporated to dryness and filtrated through a short silica column with cyclohexane/ethylacetate. The product-containing fractions are collected, evaporated, and the residue is dissolved in 20 mL methanol, to which 1.7 mL conc. HCl is added to cleave the acetal protecting groups by stirring another 24 h. After evaporation to dryness, the residue is purified by RP C-18 chromatography (Licroprep) using water/methanol; yield 2.7 g (53%) intermediate product (H-NMR, ESI MS). Reduction of the nitro group to an amino group is accomplished by dissolving 2.7 g intermediate in 120 mL methanol, to which Pd/C (0.3 g) and ammonium formate (1.27 g, 20 mmol) is added. The mixture is hydrogenated at 5 bar/room temp. for 48 h, followed by filtration over celite, evaporation and RP C-18 chromatography as described above, yield 1.9 g (74%) aminomethyl-tris(propionic acid)-tris(triglycerolamide) as viscous oil.

Example 5b

Linker Modification with 11-azidoundecane carboxylic acid

To a solution of 11-azidoundecane carboxylic acid (0.11 g, 0.5 mmol) and DIPEA (0.16 g, 1.2 mmol) in 2 mL DMF, HBTU (0.2 g, 0.56 mmol) is added and the mixture is stirred for 1 h, followed by the addition of aminomethyl-tris(propionic acid)-tris(triglycerolamide) (0.3 g, 0.33 mmol; example 5a). The mixture is stirred at room temp. for 48 h, evaporated to dryness and purified by RP C-18 chromatography (Licroprep) using water/methanol; yield 0.26 g (71%) as viscous oil.

Example 5c

Formation of Polyglycerol/Amido Dendrimer with Azidodecylcarbonyl Linker (Example 5b) Through Allylation/Dihydroxylation, Sulfation and Azide Reduction to Give Aminodecylcarbonyl Dendrimer System with 24 Sulfate Groups (Compound d18)

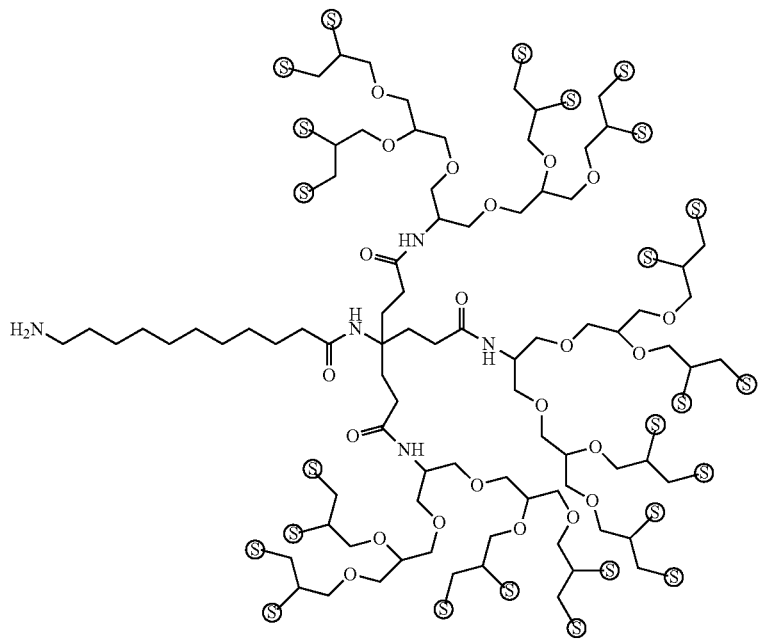

Ⓢ = $OSO_3^- Na^+$

The synthesis is accomplished as described in example 1d-e giving 120 mg of product d18 as colorless amorphous solid (MW 4432 g/mol).

Example 5c-h

The synthesis of polyglycerol/amido dendrimer systems with 24 sulfate groups and further reactive linkers is accomplished by using different bifunctional PEG-COOH NHS esters comprising an azido, propargyl, cyclooctinyl, pyridinyldisulfide, thioacetyl, or maleimido group. The reaction with compound d01 is conducted according to example 2a/4c (yields 65-86%). Table 3 summarizes achievable products d19 to d22. Another option is the derivatization of the amino group with anhydrides, such as diglycolic acid anhydride by known methods to introduce a free carboxylic acid (product d22) or conversation of the amino group into an isothiocyanate group (product d23; see also example 2i).

TABLE 3

Reactive linkers coupled to d18 and characterization of resulting product.
(dotted line indicates bond to amino group in d18 forming an amide)

| compound | Linker structure | Product MW (g/mol) | Ratio linker:dendrimer |
|---|---|---|---|
| d19 | | 4830 | 90 |
| d20 | | 5006 | 79 |
| d21 | | 4876 | 86 |
| d22 | | 4548 | 98 |

The scope of the invention regarding polyglycerol dendrimer systems of type d18 is not limited to the examples and may include other numbers n of sulfate groups, e.g. by doubling the hydroxyl groups via allylation/dihydroxylation giving 48 sulfate groups after sulfation, which give compounds in analogy to d19-d22.

Example 6

Synthesis of polyglycerol dendrimer System with 24 Sulfate Groups, NHS ester Reactive Group and Reductively Cleavable Disulfide Unit in the Linker (Compound d24)

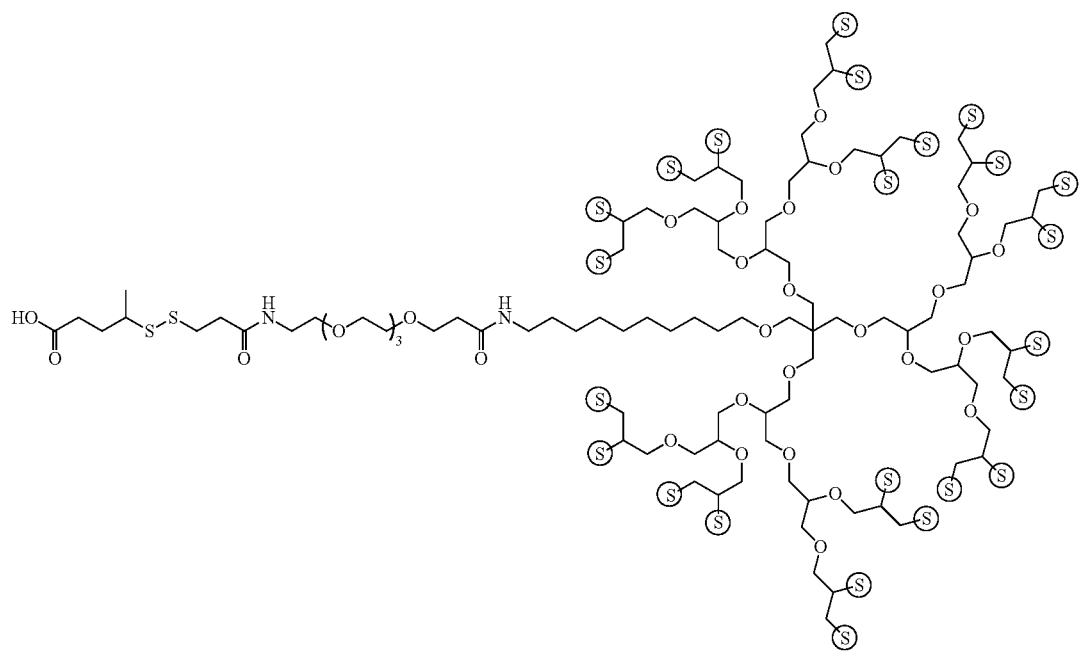

$\text{(S)} = OSO_3^-Na^+$

A solution of compound d09 (example 2h) (25 mg, 5.3 µmol) and 20 mg ion exchange resin Dowex® 50 W in 0.5 mL methanol/DMF 1:1 is shaken for 3 h, filtrated, and evaporated to dryness. The residue is dissolved in PBS buffer (50 mM; pH 7.4, incl. 1 mM EDTA)/methanol 1:1, to which 4-(2-pyridyldithio)butanoic acid (2.4 mg, 10.6 µmol; Widdison et al., J. Med. Chem. 2006, 49, 4392) is added. After 18 h stirring, the residue is evaporated and dialysed against 20% NaCl and dest. water (reg. cellulose, MWCO 1000), yield 21 mg of compound d24 as lyophilisate (MW 4764 g/mol).

Example 7

Synthesis of polyglycerol/amido dendrimer System with 24 Sulfate Groups and Triglycine Motif for Sortase-Mediated Enzymatic Ligation (d25)

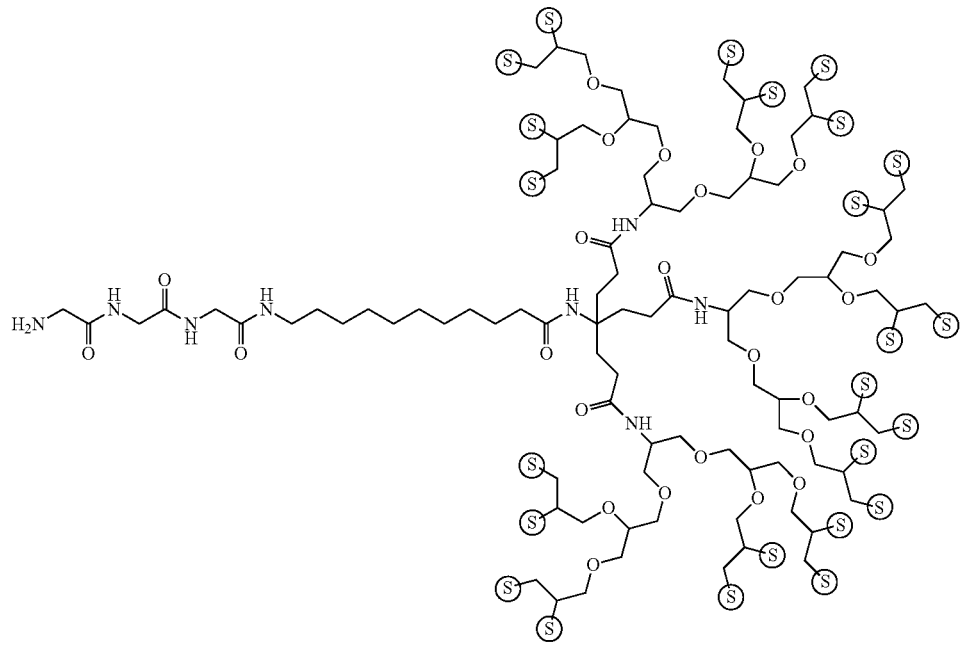

Boc-GlyGlyGly-OH (Bachem; 25 mg, 0.085 mmol) and DIPEA (11 mg, 0.17 mmol) are dissolved in 3 mL DMF and HATU (38 mg, 0.1 mmol) is added. After 1 h, compound d18 (95 mg, 0.021 mmol) is added. The mixture is stirred at 50° C. for 48 h. The product is precipitated by the addition of diethylether and collected by filtration. The residue is repeatedly washed with dichloromethane, and then suspended in 5 mL of a mixture of dichloromethane/trifluoroacetic acid 1:1, followed by 5 h stirring at room temp.

Example 8

Synthesis of Conjugates of dendrimer Systems with Fluorescent Dye ICC

Example 8a-c

Conjugation of amino dendrimer Compounds d01, d12 and d18 with Cyanine Dye

Cyanine dyes for labeling, such as Cy3 or ICC, employing different functional groups and substitution patterns, are synthetically accessible according to known literature. ICC dye (NHS ester) is a published VIS dye (abs/fluoresc. ~550 nm/575 nm) (Gröger et al., Bioconjugate Chem 2013, 24, 1507).

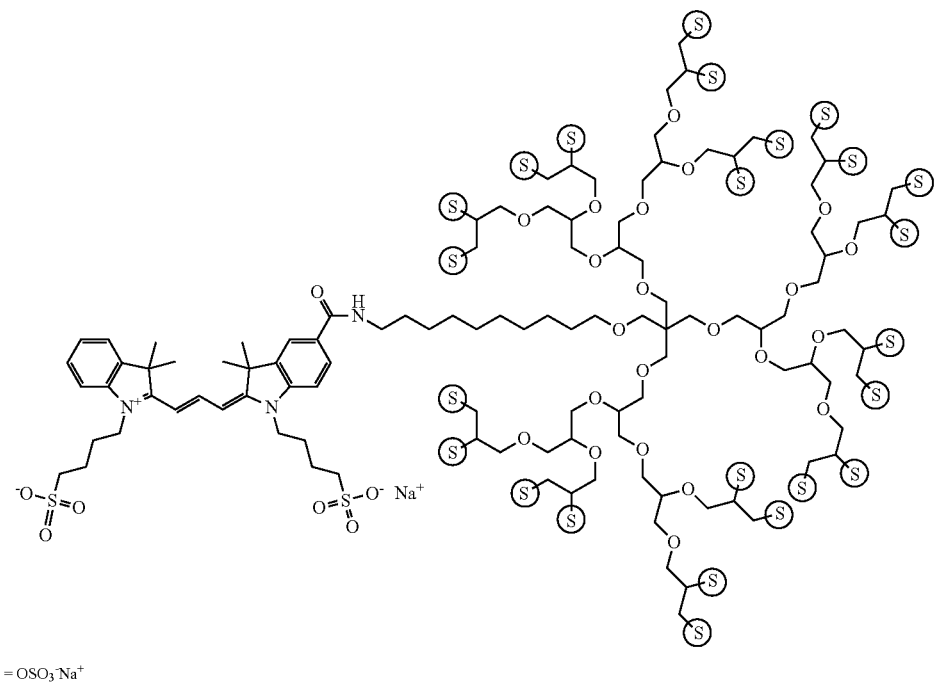

Ⓢ = OSO₃⁻Na⁺

10 mg (2.33 µmol) of compound d01 is dissolved in 1 mL DMF/water (9:1) and ICC NHS ester (MiDye550 NHS ester, Iris Biotech., Germany) (8.9 mg, 12 µmol) is added, followed by shaking at 40° C. for 72 h. The product (ICC-d01) is precipitated by addition of dichloromethane, and purified by RP C-18 chromatography (Licroprep) using water/methanol. The degree of coupling is determined by spectrophotometry (ICC dye $\lambda_{max}$ at 550 nm, ε 120.000 L⁻¹ M⁻¹) giving 54% degree of coupling. The dendrimers d12 and d18 are covalently conjugated with ICC dye NHS ester in analog fashion.

Other fluorescent dye NHS esters can be conjugated as described here, such as cyanine dye ITCC NHS ester, Cy3 to Cy7 NHS esters, rhodamine or fluorescein NHS esters. Also, commonly known isothiocyanate (ITC) derivatives of such dyes, such as FITC, can be used.

Another method for dye conjugation is to use amino dendrimers (e.g. d01, d12, d18) in combination with 2-iminithiolane and maleimido dyes (e.g. ICC maleimide) giving, as example, ICC-IT-d01 or ICC-IT-d18.

Example 9

Synthesis of dendrimer with UV-Detectable Linker (d26)

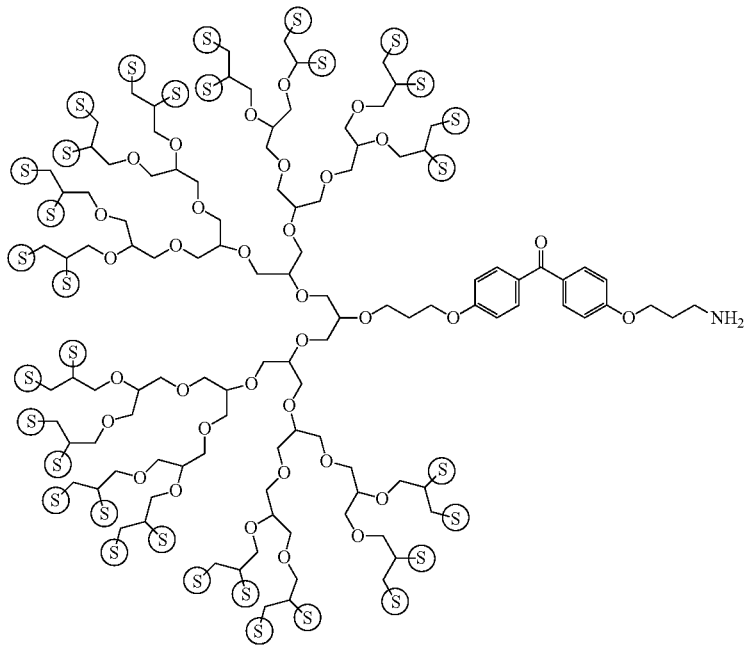 [SMILES: NCCCOc1ccc(C(=O)c2ccc(OCCCOC(COC(COC(COCC(COCC(S)CS)OCC(S)CS)COCC(COCC(S)CS)OCC(S)CS)COC(COCC(COCC(S)CS)OCC(S)CS)COCC(COCC(S)CS)OCC(S)CS)COC(COC(COCC(COCC(S)CS)OCC(S)CS)COCC(COCC(S)CS)OCC(S)CS)COC(COCC(COCC(S)CS)OCC(S)CS)COCC(COC(S)CS)OCC(S)CS)cc2)cc1]

The synthesis of d26 is accomplished in analogy to example 4, using 4,4'-di-(3-bromopropyloxy)benzophenone (Yan et al., Bioorg. Med. Chem. 2013, 21, 508) instead of 1,10-dibromodecane, as linker. Dendrimer d26 can then be further modified as described in examples 4c-h to be used for protein conjugation. 4,4'-di-(3-bromopropyloxy)benzophenone linkers can be used to built up dendrimers of the type of examples 1-3.

Example 10

Synthesis of Dendrimer with VIS-Detectable Cyanine Dye Linker (d28)

Example 10a

Synthesis of Polyglycerol Dendrimer System with 24 Sulfate Groups and Aminohexyl Linker (Compound d27)

Compound d27 is an analog to d01 with aminohexyl group and is synthesized according to example 1a-e using 1,6-dibromohexane as starting material; d27 molecular weight 4240 g/mol.

Example 10b

Conjugation with Indocyanine Moiety as VIS-Detectable Linker and NHS Ester Reactive Group (d28)

5,5'-Dicarboxy-1,1'-dimethylindocarbocyanine, monoacetate is synthesized according to known procedures. To a solution of 0.1 g (0.2 mmol) of this dye and DIPEA (0.11 g, 0.8 mmol) in 3 mL DMF is added a solution of HBTU (0.31 g, 0.8 mmol) in 0.5 mL DMF. After 90 min stirring at room temp., d027 (0.17 g, 0.04 mmol) is added portionwise as a solid and the resulting mixture stirred at 60° C. for 72 h. The product is precipitated by adding 3 mL diethylether and collected by centrifugation. Purification by RP C-18 chromatography (Licroprep) using water/methanol yields 0.12 g intermediate after lyophilisation. Conversion into the NHS ester is conducted by adding HSTU (75 mg, 0.2 mmol) to a solution of intermediate and 35 µL DIPEA in 1 mL DMF and stirring for 18 h at room temp., followed by precipitation in diethylether (repeated circles of DMF/dietyhlether), giving 0.10 g product d28 (mol. weight 4743 g/mol).

Example 11

Synthesis of Conjugates of dendrimer Systems with Proteins and Antibodies

Example 11a

General Procedure for the Conjugation Using Dendrimer Systems with Maleimido Groups (d02, d03, d13, d14, d19, d20)

A solution of 2 mg of protein in 1 mL of 50 mM phosphate buffer pH 7.4/10 mM EDTA is reacted with 10 mol-eq. 2-iminothiolane for 60 min. To this mixture is added 14 mol-eq. of maleimido-functionalized dendrimer (e.g. d02, d03, d13, d14, d19, d20), followed by incubation for 18 h. The mixture is subjected to purification into TRIS-buffered saline (TBS; pH 7.4) using NAP10 column or Slide-A-Lyzer dialysis cassettes (reg. cellulose, MWCO 10 kDa).

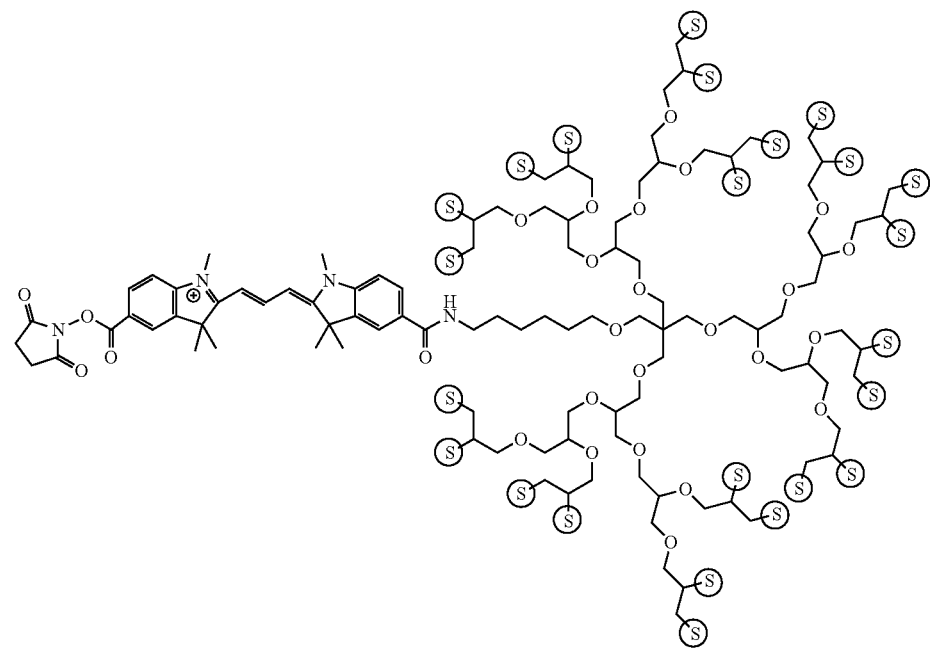

$\text{S}$ = $OSO_3^-Na^+$

Example 11b

General Procedure for the Conjugation Using Dendrimer Systems with Pyridyldisulfide Group (d04, d05, d15, d21)

A solution of 2 mg of protein in 1 mL of 50 mM phosphate buffer pH 7.4/10 mM EDTA is reacted with 10 mol-eq.

2-iminothiolane for 60 min. To this mixture 10 mol-eq. of maleimido-functionalized dendrimer (e.g. d04, d05, d15, d21) is added, followed by incubation for 3 h. The mixture is subjected to purification into TRIS-buffered saline (TBS; pH 7.4) using NAP10 column or Slide-A-Lyzer dialysis cassettes (reg. cellulose, MWCO 10 kDa).

Example 11c

General Procedure for the Conjugation Using Dendrimer Systems with Isothiocyanate or NHS Ester Group (d10, d11, d23)

A solution of 2 mg of protein in 1 mL of PBS pH7.4 is reacted with 10 mol-eq. of isothiocyanate or NHS ester dendrimer (e.g. d10, d11, d23) for 24 h. The mixture is subjected to purification into TRIS-buffered saline (TBS; pH 7.4) using NAP10 column or Slide-A-Lyzer dialysis cassettes (reg. cellulose, MWCO 10 kDa).

Example 12

Synthesis of Conjugates of Dendrimer Systems with Enzymes

Example 12a

Conjugation of Dendrimer Systems with Maleimido Groups (d02, d13, d19) with the Enzyme L-asparaginase L-asparaginase is a homotetramer of 4 units of 34 kDa molecular weight, which can be modified at a disulfide bridge in each of the monomer units (Balan et al., Bioconjugate Chem 2007, 18, 61). L-asparaginase (10 mg, 0.29 μmol monomer; L-asparaginase 5000E, Medac, Germany) is dissolved in 2 mL of 50 mM phosphate buffer pH8/10 mM EDTA. Dithiotreithol (DTT; 80 mg) is added and the solution shaken for 1 h. Excess DTT is removed via SEC (Sephadex G50; phosphate buffer pH8/10 mM EDTA). To the resulting solution (approx. 8 mg in 4 mL, as measured by UV), a solution of 2.3 μmol (8 mol-eq.) of maleimido dendrimer (e.g. d02, d13, d19) in approx. 0.2 mL of water is added, followed by incubation for 24 h under gentle shaking. Purification is achieved by ultrafiltration (centriprep flasks, reg. cellulose, MWCO 20.000).

Example 12b

Conjugation of dendrimer Systems with Maleimido Group (d02) with the Enzyme DNase The synthesis is accomplished as described in example 11a yielding DNase-d02 as solution in TBS pH 7.4.

Example 12c

Conjugation of Dendrimer Systems with Isothiocyanate Group (d10) with the Enzyme DNase To a solution of 2 mg (65 nmol) DNase (desoxyribonuclease I from bovine pancreas, 31 Da) in 1 mL PBS pH7.4 is given 5 mol-eq. isothiocyanate dendrimer d10 (1.4 mg) in 0.2 mL PBS, followed by reaction at room temp. for 18 h. Purification is accomplished in Float-A-Lyzer dialysis cassettes (cellulose ester, MWCO 10 kDa) into TBS pH 7.4.

TABLE 4

Protein conjugates with dendrimer systems according examples 11 and 12

| protein | dendrimer | conjugate product according to general formula I |
|---|---|---|
| saporin | d02, d13, d19 | saporin-d02 |
| | | saporin-d13 |
| | | saporin-d19 |
| ovalbumin | d02, d03, d20, d28 | ova-d02 |
| | | ova-d03 |
| | | ova-d20 |
| | | ova-d28 |
| apoptin | d02, d13 | apo-d02 |
| | | apo-d13 |
| diphtheria toxin | d02, d13 | dph-d02 |
| | | dph-d13 |
| human serum albumin (HSA) | d21 | HSA-d21 |
| rCys-Protein G | d02, d13, d19 | ProtG-d02 |
| | | ProtG-d13 |
| | | ProtG-d19 |
| bevacizumab | d10, d11, d13 | bev-d11 |
| | | bev-d23 |
| IgG | d22 | IgG-d22 |
| | d28 | IgG-d28 |
| L-asparaginase | d02, d13, d19 | asp-d02 |
| | | asp-d13 |
| | | asp-d19 |
| DNase | d02, d10 | DNase-d02 |
| | | DNase-d10 |

Protein conjugates with dendrimer systems according to table 4 can be additionally conjugated with fluorescent dyes in order to detect the conjugates in biological systems. Fluorescence labeling is a known procedure and can be accomplished with a variety of reactive fluorophores. Here, the dye ICC NHS ester (Gröger et al., Bioconjugate Chem 2013, 24, 1507) is used in the examples demonstrating results of cellular uptake by FACS and microscopy.

Example 13

Synthesis of Conjugates of Dendrimer Systems with Small Molecule Peptides and Peptidomimetics Example 13a Synthesis of Dendrimer Conjugate with Monomethyl Auristatin E

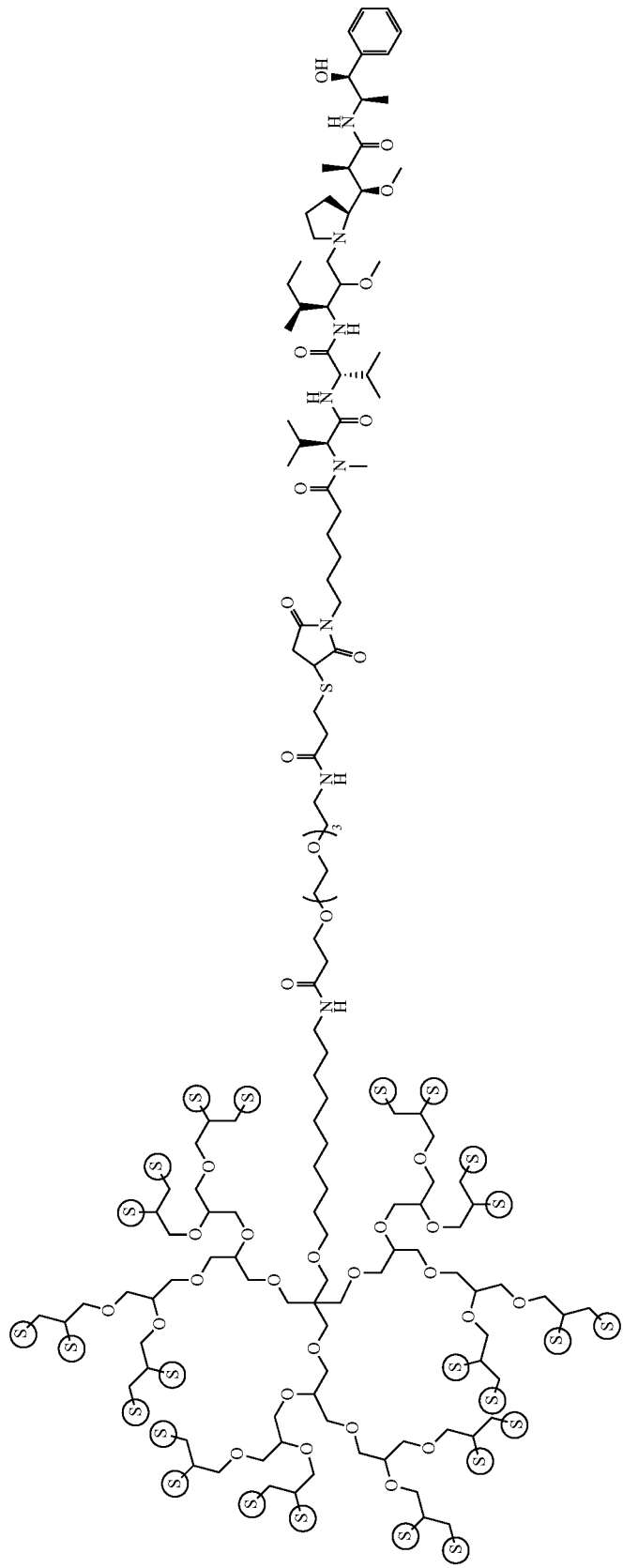

Maleimidocaproyl-monomethyl auristatin E (mc-MMAE) can be synthesized according to the literature (Doronina et al., 2006, 17, 114). Conjugation is achieved by dissolving dendrimer d09 (2 mg, 0.43 μmol) in 0.5 mL of an aqueous 50 mM hydroxylamine solution, followed by adding maleimidocaproyl-monomethyl auristatin E (0.37 mg in 0.5 mL DMF/PBS 1:1). After 18 h incubation at 25° C., the product is precipitated with dichloromethane, followed by HPLC purification (water/methanol) giving MMAE-d09 (1.1 mg).

Other not limiting examples of structures of dendrimers d01 with auristatin effector molecules which are synthesized according to methods described herein may include:

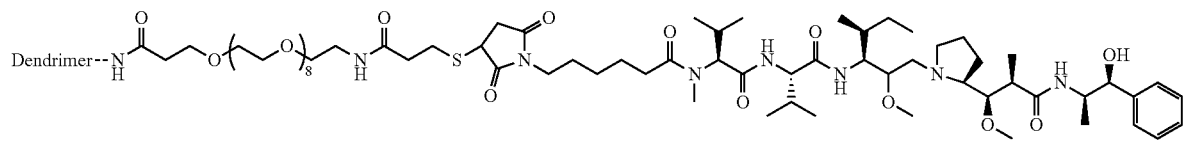

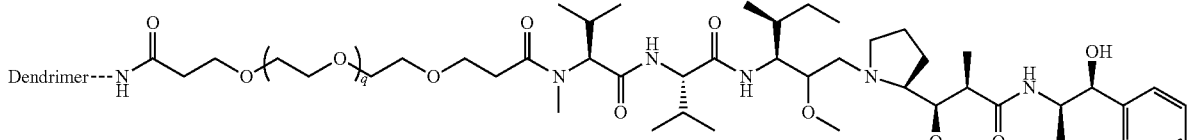

q = 1-20

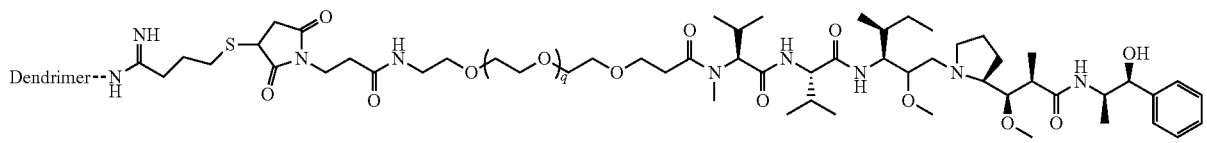

q = 1-20

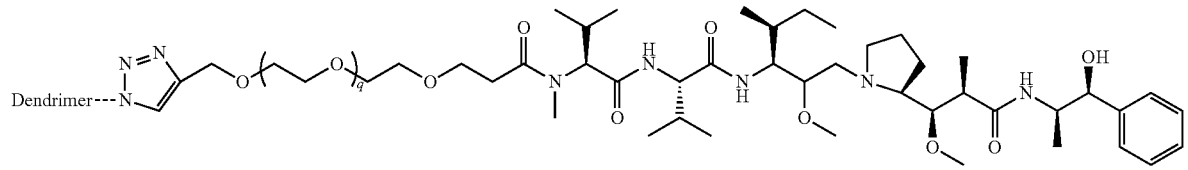

q = 1-20

Example 13b

Synthesis of dendrimer Conjugate with Stapled Peptide

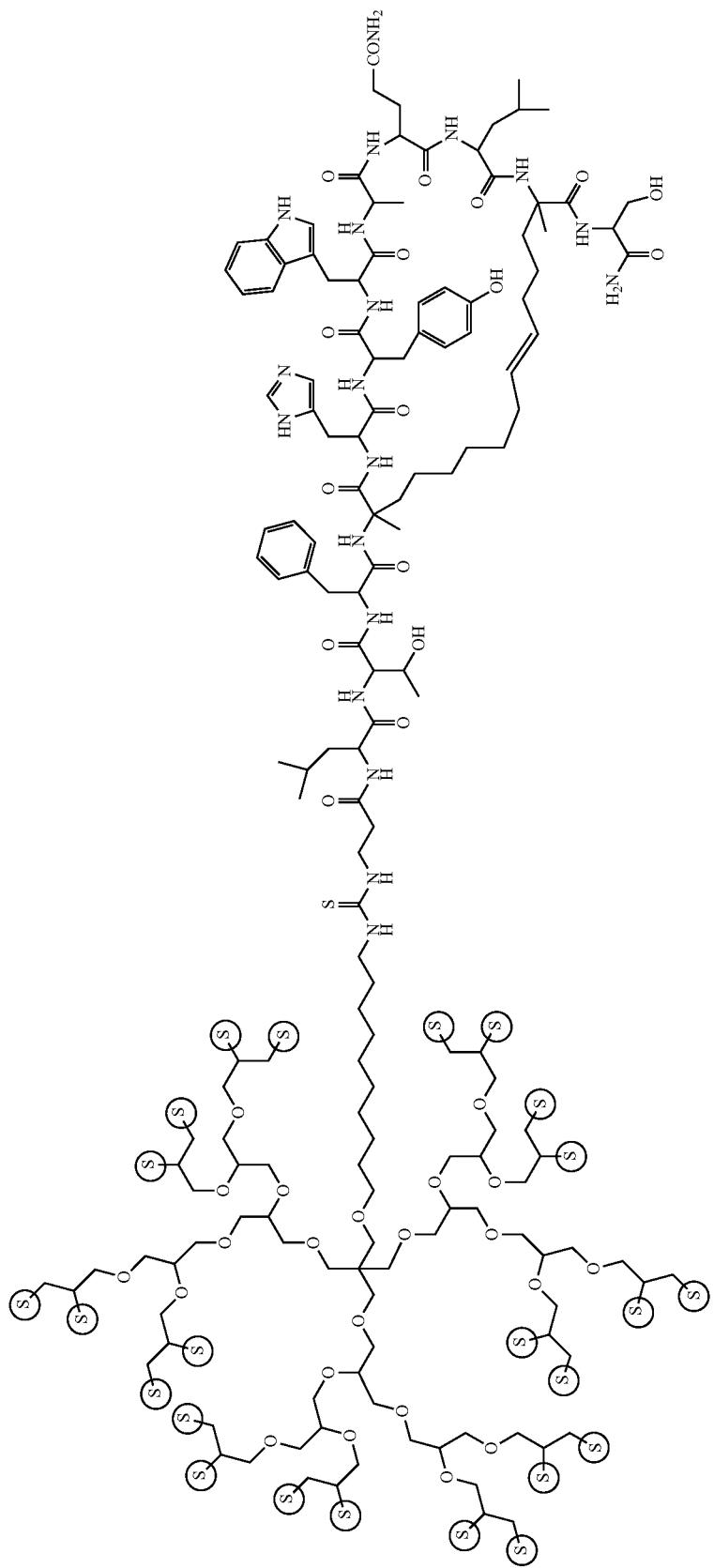

Stapled peptide for activation of p53 pathway (ATSP-3900 with N-terminal β-alanine) can be synthesized according to the literature (Chang et al., PNAS 2013, 110, E3445). Conjugation is achieved by dissolving dendrimer d10 (2 mg, 0.46 μmol) in 0.5 mL 50 mM Phosphate buffer pH8. To this solution, a solution of β-Alanyl-ATSP-3900 (0.65 mg, 0.40 μmol) in 0.2 mL DMF is added, followed by reaction at 40° C. for 24 h. Purification is achieved by HPLC (water/methanol) giving ATSP3900-d10 conjugate (0.8 mg).

Example 13c

Synthesis of dendrimer Conjugates with Alpha-Helical Peptides Derived from Natural Binding Motifs The peptide sequences P1 to P7 (as C-terminal amides) were synthesized by common solid-phase peptide synthesis. These peptides carry a N-terminal cystein for conjugation of maleimido dendrimers to the thiol group. Conjugation to dendrimers d02, d03, d13, d14, d19 was performed. As example, the procedure employing dendrimer d02 is described:

1 mg peptide is dissolved in 200 μL DMF and further diluted with 50 mM phosphate buffer (up to 500 μL). To this solution is added 5 mol-eq. of TCEP (stock solution in water) followed by 0.9 mol-eq. of dendrimer, dissolved in 200-300 μL water. The mixture is shaken gently at 25° C. for 18 h. Purification is achieved by HPLC (water/acetonitrile) or SEC (Sephadex LH-20, water/DMF), or a combination of both, giving conjugates listed in table 5.

TABLE 5

Peptide conjugates with dendrimers according to example 13 c

| # | original protein | Synthesized peptide sequence for conjugation | Conjugates |
|---|---|---|---|
| P1 | BIM | CGMRPEIWIAQELRRIGDEFNA (SEQ ID NO: 1) | d02-P1 |
| P2 | BIM | CGDMRPEIYI(Aib)QELRRIGD(Aib)Y (SEQ ID NO: 2) | d02-P2 |
| P3 | Bcl9 | CGLSQEQLEHRERSLQTLRDIQRMLF (SEQ ID NO: 3) | d02-P3, d03-P3 |
| P4 | Bcl9/2 | CGLSKEQLEHRERSLQTLRDIERLL (SEQ ID NO: 4) | d02-P4, d03-P4 |
| P5 | PUMA | CGEEQWAREIGAQLRRMADDLNAQYER (SEQ ID NO: 5) | d02-P5 |
| P6 | BID | CGEDIIRNIARHAAQVGASADRSI (SEQ ID NO: 6) | d02-P6 |
| P7 | c-myc | CPKVVILKKATAYILSVQAEEQKL (SEQ ID NO: 7) | d02-P7 |

Example 14

Synthesis of Conjugates of dendrimer Systems with Small Molecule Inhibitors

Example 14a

Synthesis of dendrimer Conjugate with Staurosporine

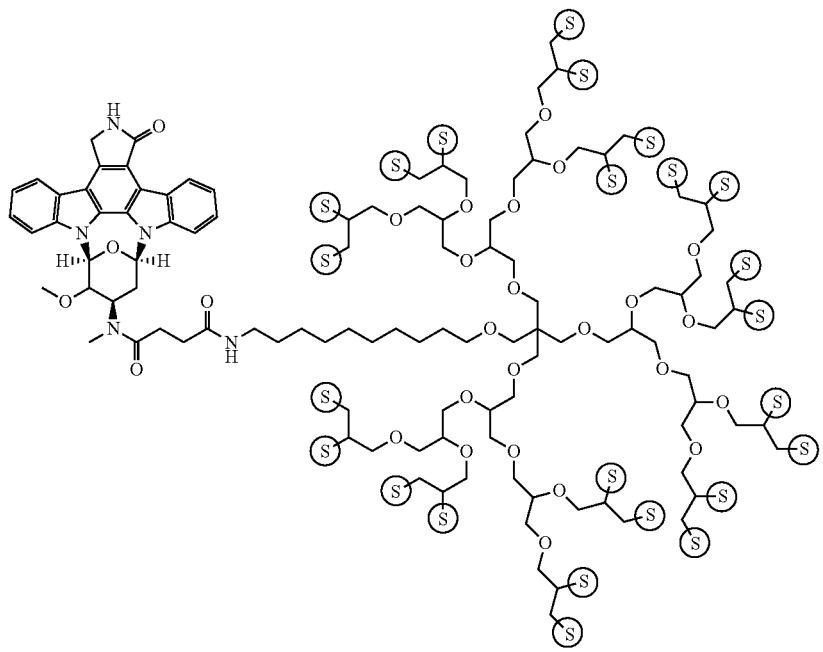

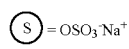
= OSO₃⁻Na⁺

Staurosporine is a kinase inhibitor which can be conjugated to carrier molecules while maintaining its inhibitory activity. Succinoyl-staurosporine is synthesized as described (Caravatti et al., Bioorg. Med. Chem. Lett. 1994, 4, 399) and conjugated to d01 in DMF using HATU/DIPEA coupling conditions.

Example 14b

Synthesis of dendrimer Conjugate with Maytansine Derivative

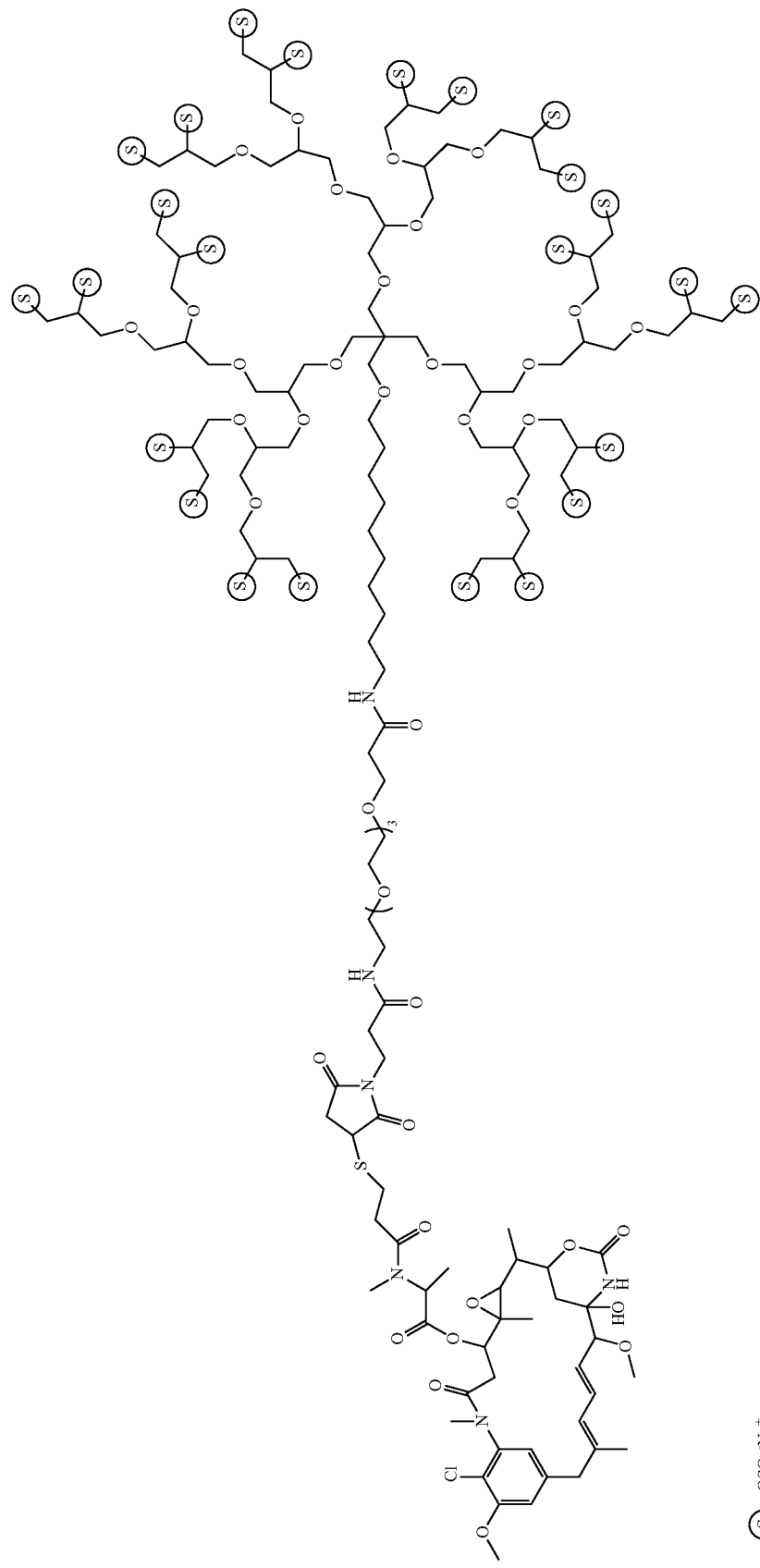

N$^{2'}$-deacetyl-N$^{2'}$-(3-mercapto-1-oxopropyl)-maytansine is a published derivative suited for covalent conjugation to biomolecules via disulfide bonds or maleimido groups (Erickson et al. Bioconjugate Chem. 2010, 21, 84). The covalent conjugation to dendrimer systems of types d02, d03, d13, d19, d20 (maleimides) is possible. Exemplary, A solution of N$^{2'}$-deacetyl-N$^{2'}$-(3-mercapto-1-oxopropyl)-maytansine (5 mg, 6.8 µmol) and dendrimer d02 (24 mg, 5.2 µmol) in 0.5 mL DMF/50 mM phosphate buffer pH7.0+5 mM EDTA (9:1) is reacted for 3 h at room temp., the product precipitated by adding 1 mL dichloromethane. Excess maytansine is removed by repeated circles of precipitation from DMF/dichloromethane, giving 21 mg may-d02 (mol. weight 5432 g/mol).

Example 15

Cellular Uptake of Dendrimer-ICC Dye Conjugates (Example 8) and Dendrimer-Protein Conjugates (Example 11)

Figure 8:
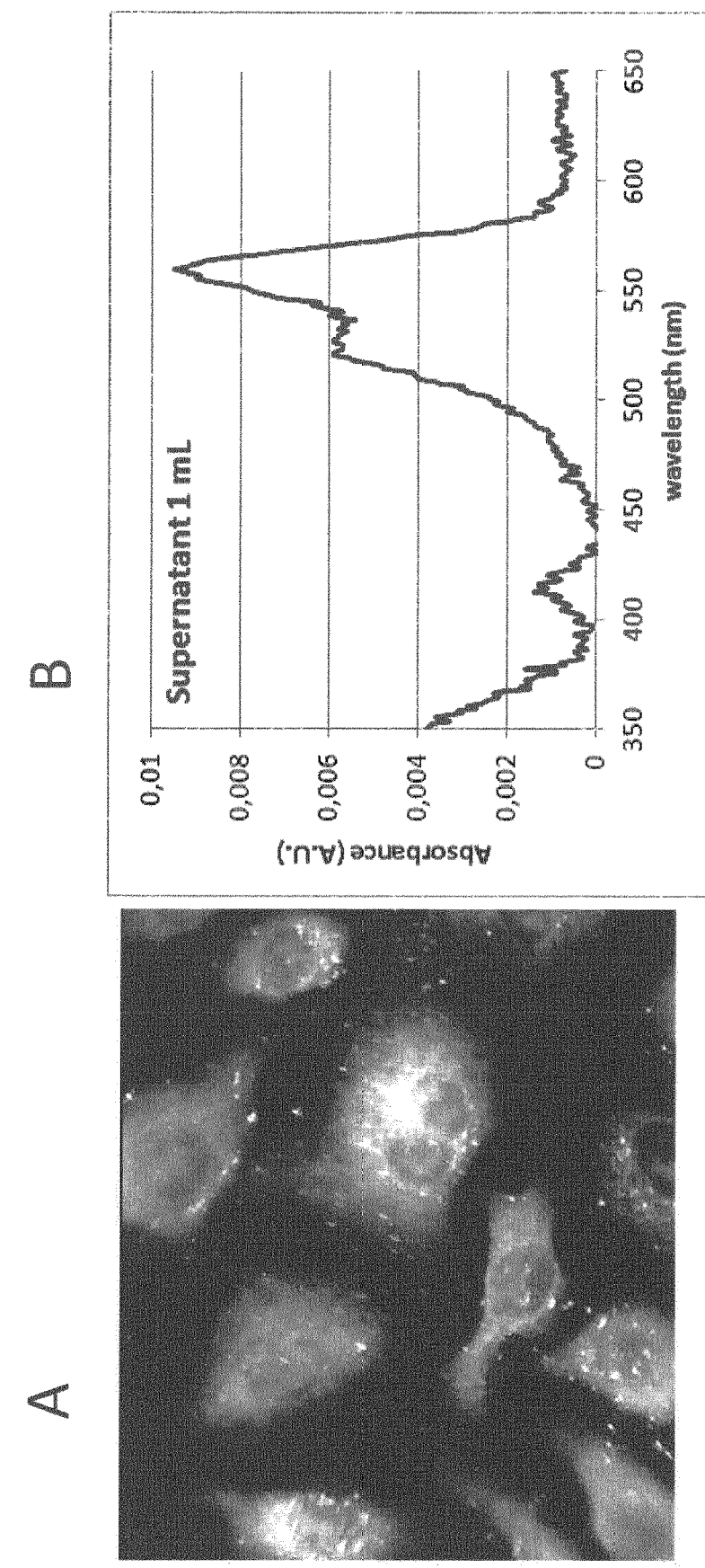
FIG. 8A depicts a microscopic image of SKBR3 cells showing fluorescence of ICC-d02 as homogeneous distribution allowing visualization of the cell body.
FIG. 8B shows the absorption spectrum of cell lysate of SKBR3 after incubation with ICC-d02 giving 5 Mio molecules/cell recovered from intracellular compartment.

The human cancer cell lines A2780 and QGP-1 are cultured in RPMI medium, with 10% fetal calf serum (FCS), 2% glutamine, and penicillin/streptomycin added. All cells are seeded into medium at $1 \times 10^5$ cells/ml, cultured at 37° C. with 5% $CO_2$, and split 1:5 two times a week. The epithelial human cancer cell lines A549, MCF7, HaCaT, and HepG2 are propagated in DMEM medium (PAN Biotech), with 10% fetal FCS, 2% glutamine, and penicillin/streptomycin. Cells are seeded into medium at $1 \times 10^5$ cells/ml (37° C. with 5% $CO_2$, split 1:5 two times a week). HT29 cells are cultured in McCoy's medium (PAN biotech), with 10% FCS), 2% glutamine, and penicillin/streptomycin. Cells are seeded into medium at $1 \times 10^5$ cells/ml (37° C. with 5% $CO_2$, split 1:10 two times a week). For cellular microscopy, cells are seeded at $2 \times 10^5$ cells/ml in a 24-well culture plate on glass coverslips (Sigma), cultured for 24 hours at 37° C., then cultured with medium containing $10^{-6}$ M of ICC-d01, ICC-d12, ICC-d18 or respective derivatives with 48 sulfate groups, or dendrimer conjugates with proteins (examples 12 and 13) or $10^{-6}$ M glycerol-ICC (control) for up to 24 hours at 37° C. Afterwards, cells are fixed with cold acetone, rinsed and covered with 4,6-diamidino-2-phenylindole (DAPI, Abcam) for nuclear counterstain. Image acquisition is performed using a Leica DMRB microscope (Leica). Images are taken with a digital camera (Spot 32, Diagnostic Instruments) with the same exposure time for all pictures. FIG. 8A shows an example of intracellular distribution in the cytosolic areas (ICC-d01, example 8). To quantify the cellular uptake mediated by the sulfated dendrimers, ICC-d01 (example 8) is used to incubate $10^7$ SKBR3 tumor cells with $10^{-6}$ M ICC-d01 for 24 h. This amount and time is sufficient to measure the supernatant after pooling and cell lysis with DMSO. FIG. 8B shows the resulting absorption spectrum (ICC ext.coeff (559 nm) 150,000 M$^{-1}$ cm$^{-1}$) giving $10^{-17}$ moles per cell, which corresponds to approx. 5 Mio molecules per cell.

For FACS studies, $2 \times 10^5$ cells/ml cells are cultured in 24-well plates with normal culture medium or medium containing different concentrations of test substances for 3 or 24 hours. Thereafter, cells are washed with PBS and detached with 200 µl/well accutase (PAA) and washed two times with PBS. Cells are fixed with 500 µl 3% paraformaldehyde for 10 min at 4° C., stopped with 2 ml PBS and centrifuged with 250×g, for 10 min at 4° C. Supernatants are removed and cells were suspended in 200 µl PBS with 0.5% bovine serum albumin (Roth).

Fixed cells are kept at 4° C. until analysis in a FACS Calibur instrument (Becton-Dickinson). Table 5 shows examples of FACS analysis.

TABLE 5

Values of uptake measured by FACS, relative to ICC-d01 (range from different cell lines: HT29, HepG2, QGP-1, A431, MCF-7, A2780) after incubation for 24 h. All conjugates were additionally conjugated with ICC NHS ester, and values were corrected by fluorescence due to differing dye-to-protein ratio or dendrimer loading.

| Compound | % uptake |
| --- | --- |
| ICC-d01 (dendrimer dye only) | 100 |
| ICC-IT-d01 (dendrimer dye only) | 85-100 |
| ICC-d18 (dendrimer dye only) | 110-125 |
| ICC-IT-d18 (dendrimer dye only) | 95-110 |
| Sap (without dendrimer) | 5-8 |
| Sap-d02 | 55-70 |
| Diphtheria toxin (without dendrimer) | 8-10 |
| Dph-d02 | 45-68 |
| L-asparaginase (without dendrimer) | 4-7 |
| Asp-d02 | 85-95 |
| DNase (without dendrimer) | 4-12 |
| DNase-d02 | 50-65 |
| IgG (without dendrimer) | 3-5 |
| IgG-d02 | 30-45 |

Example 16

Activity of Protein-dendrimer Conjugates in Tumor Cells

For cytotoxicty measurements, $2 \times 10^5$ cells were incubated with 1 ml culture medium containing increasing concentrations of test substances. After 72 hs treatment, cell number, viability and cell diameter as parameter of apoptotic processes were analyzed in a cell counter and analyzer system (CASY®, Schärfe Systems). In addition, drug cytotoxicity was assessed in vitro using the MTT assay (cellular reduction of 3-(4,5-dimethylthiazol-2-yl)-2,5-diphenyltetrazolium bromide) as a test for metabolic activity of the cells. $1 \times 10^4$ cells per well were seeded in 96-well plates in 100 µl culture medium containing increasing concentration of the test substance. 10 µl MTT (5 mg/ml in PBS, obtained from Sigma) was added to each well and the plates were incubated for 4 hrs, 24 hrs, 48 hrs or up to 72 h. The resulting formazan product was dissolved with acid isopropanol and the absorbance at a wavelength of 570 nm (Ex570) was read on a Microplate Spectrophotometer (Anthos htII, Microsystems). In a couple of experiments, medium with test substances was removed after 48 hs, cells were counted and identical cell numbers with new medium without test substances were seeded in new plates. MTT assay was performed after further incubation for 72 hours.

As examples, table 6 shows that conjugates of ribosomal-inhibiting toxins exhibit an increased cytotoxicity due to cellular uptake and intracellular activity. Effects are obtainable by using e.g. compounds Sap-d02, Sap-d13 or Sap-d19. Similar effects are obtainable in different tumor cells lines, such as HT29 colon tumor cells, HepG2 liver tumor cells, QGP-1 pancreatic tumor cells, A431 epidermoid tumor cells;

TABLE 6

IC$_{50}$ values of inhibition of cell proliferation
measured by MTT test (range from different cell
lines: HT29, HepG2, QGP-1, A431, MCF-7, A2780.

| Compound | IC$_{50}$ |
| --- | --- |
| Sap (without dendrimer) | >1 μM |
| Sap-d02 | 2-5 nM |
| Sap-d13 | 4-8 nM |
| Diphtheria toxin (without dendrimer) | >0.5 μM |
| Dph-d02 | 1-3 nM |
| L-asparaginase (without dendrimer) | >1.5 μM |
| Asp-d13 | 10-20 nM |
| DNase (without dendrimer) | >2 μM |
| DNase-d10 | 4-9 nM |

Example 17

Activity of Peptide-Dendrimer Conjugates in Tumor Cells

Cell culture measurements were performed as described in example 16. Table 7 shows results for the different peptide-dendrimer conjugates.

TABLE 7

IC$_{50}$ values of inhibition of cell proliferation
measured by MTT test (range from different cell
lines: HT29, HepG2, QGP-1, A431, MCF-7, A2780.

| Compound | IC$_{50}$ |
| --- | --- |
| d02-P1 | 0.9-2.1 μM |
| P1 (peptide without dendrimer) | >10 μM |
| d02-P2 | 0.8-1.7 μM |
| d03-P3 | 0.6-1.2 μM |
| P3 (peptide without dendrimer) | >10 μM |
| d03-P4 | 0.4-1.1 μM |
| P4 (peptide without dendrimer) | >10 μM |
| d02-P5 | 0.8-2.0 μM |
| P5 (peptide without dendrimer) | >10 μM |
| d02-P6 | 1.2-2.3 μM |
| P6 (peptide without dendrimer) | >10 μM |
| d02-P7 | 1.1-1.8 μM |
| P7 (peptide without dendrimer) | >10 μM |

Example 18

Selectivity of Intracellular Uptake of Dendrimer Conjugates with Proteins: Effects of Inhibitors on Uptake of L-Asparaginase Conjugate Asp-d02 (Example 12a)

Studies on cellular uptake measured by FACS were conducted as described in example 13. Compound Asp-d13 is incubated at a concentration of 10$^{-7}$ M in QGP-1 tumor cells for 3 h and 6 h. Incubation is done in the presence of one of the following two substrates: (1) 0.1 mM genistein, an inhibitor for endocytotic uptake (Rejman et al., Mol. Ther. 2005, 12, 468-474) or (2) 50 mM rifamycin, an inhibitor of uptake via organic anion transporter proteins (OATP; Bi et al., Drug Metab Dispos. 2012, 40, 1085-92). The results demonstrate that FACS signals relative to Asp-d13 without inhibitor (defined as 100%) decrease in the presence of rifamycin to 37-40%, whereas no significant decrease can be measured in the presence of genistein (80-85%), see table 7 for data. For L-asparaginase coupled to a polyglycerolsulfate (mean molecular weight of 12000 Da; used according to WO2011/095311) endocytosis could be identified due to inhibition by genistein.

TABLE 7

Relative values of inhibition of uptake into QGP-1
cells in presence of rifamycin or genistein.

| Compound | time | w/o inhibitor (%) | +genistein (%) | +rifamycin (%) |
| --- | --- | --- | --- | --- |
| Asp-d02 | 3 h | 100 | 81 | 58 |
| Asp-d02 | 6 h | 100 | 95 | 53 |
| Asp-polyglycerolsulfate | 3 h | 100 | 50 | 76 |
| Asp-polyglycerolsulfate | 6 h | 100 | 55 | 72 |

Example 19

Activity of Protein-Dendrimer Conjugates in Tumor Cells in Comparison to Sulfated Polymer In this example, saporin conjugate Sap-d02 (example 11) is compared with an analog conjugate using a polyglycerolsulfate of polymeric, nondefined nature with comparable molecular weight (average value at 6000 g/mol; synthesized according to Gröger et al., Bioconjugate Chem 2013, 24, 1507). This polymer is functionalized with the linker maleimido-PEG(4)-COOH NHS ester as described in example 2a, and further purified via RP chromatography. Conjugation to saporin is accomplished as described in example 11. Comparative cytotoxicity measurements are conducted according to example 16 giving IC$_{50}$ values from MTT test in 4 different cell lines (see table 8).

TABLE 8

IC$_{50}$ values of inhibition of cell proliferation measured by MTT test
(range from different cell lines: HT29, HepG2, QGP-1, MCF-7).

| Compound | IC$_{50}$ |
| --- | --- |
| Sap (without dendrimer) | >1 μM |
| Sap-d02 | 2-5 nM |
| Sap-polyglycerol sulfate | 38-45 nM |

Example 20

Chemoselective and Site-Specific Conjugation Methods of Dendrimers with Proteins Employing an N-Terminal Cystein (Cystag)

Example 20a

Dendrimers can be conjugated with protein and antibody therapeutics, as well as synthetic peptides, when these polyamino acids are provided with a cystein tag, thereby enabling chemoselective conjugation to cystein with dendrimers carrying maleimido, pyridinyldisulfide or other thiol-selective groups know to the skilled artisan (such as bromoacetyl, vinylsulfone).

General protocol for conjugation of proteins (25-30 kDa) with Cystag: 1 mL of a solution of protein (conc. 2 mg/mL) in PBS containing 1 mM EDTA is incubated with a solution of TCEP in PBS (yielding 1 mM TCEP in the mixture) for 3 h at room temp., followed by the addition of 2 mol-eq. maleimido-containing or pyridinyldisulfide-containing, sulfated dendrimers (e.g. d02-d05, d13-d15) and reaction of further 2 h at room temp. Purification is accomplished in Float-A-Lyzer dialysis cassettes (cellulose ester, MWCO 10 kDa) into TBS pH7.4.

Example 20b

Proteins with N-terminal cystein or cystein surrogates can be fused with other macromolecules employing a thioester moiety by the process of native chemical ligation (NCL) (Wong C T et al, Mol Biosyst. 2013, 9, 826-33). Surprisingly, sulfated dendrimers can be synthesized as thioesters and enable NCL-type conjugation to proteins with N-terminal cystein.

Synthesis of sulfated dendrimers with thioester group: A solution of sulfated dendrimer with NHS ester (d11; 10 mg) in DMF (1 mL) is reacted with 10 mol-eq. of 3-thiopropionic acid methylester (Xiao et al., Bioorg Med Chem Lett 2013, 23, 6046-6051) for 24 h at 40° C. After repeated precipitation in DMF/ethylacetate and lyophilization from dest. water, 11 mg of product d29 were obtained as yellow solid.

General protocol for conjugation of proteins (25-30 kDa) with Cystag: 1 mL of a solution of protein (conc. 2 mg/mL) in NCL-buffer containing MPAA and TCEP in 50 mM phosphate buffer pH7.0 is incubated 2.5 mol-eq. of dendrimer d29 for 24 h at room temp. Purification is accomplished in Slide-A-Lyzer dialysis cassettes (reg. cellulose, MWCO 20 kDa) into PBS pH7.4. The product contains a free cystein according to the mechanism of NCL and can be additionally conjugated to a fluorescence dye (such as ICC maleimide).

Example 21

Chemoselective Conjugation Via Reductive Amination Using a Sulfated Dendrimer with Carbaldehyde Group

Example 21a

Synthesis of Sulfated Dendrimer d31 with Carbaldehyde Group

The azido group in dendrimer d06 (example 2e) is reduced to the amine by TCEP. To a solution of d06 (50 mg, 0.011 mmol) in 1 mL of a mixture of water/methanol (1:1) TCEP (20 mg, 0.067 mmol) is added and the mixture is stirred at room temp. for 18 h. After evaporation, the residue is dialysed against 20% NaCl and dest. water (reg. cellulose, MWCO 1000), yield 45 mg (90%) of compound d30 after lyophilisation (molecular weight 4631 g/mol). Modification with a carbaldyehyde is accomplished by reaction with 4-formylbenzoic acid N-hydroxysuccinimidyl ester (Hooker, J M et al., Nano Letters 2007, 7, 2207-2210) in DMF/water, yielding sulfated dendrimer d31 as solid precipitate (molecular weight 4763 g/mol).

Example 21b

Chemoselective Conjugation of Sulfated Dendrimers d31 to Proteins Via Reductive Amination The process is performed with protein solutions of 2.5 mg/mL in 50 mM phosphate buffer pH7.0. General procedure: A solution of 1 mg protein (0.4 mL) and 3 mol-eq. of dendrimer d31 is treated with a stock solution of sodiumcyanoborohydride ($NaBH_3CN$) in water yielding a final concentration of 1 mM $NaBH_3CN$ in the mixture, which is gently shaken for 48 h at 20° C. Purification is accomplished in Slide-A-Lyzer dialysis cassettes (reg. cellulose, MWCO 20 kDa) into TBS pH7.4. Dendrimer conjugation is determined by gel electrophoresis, yielding conversion of 50-70% of protein into conjugates (dendrimer-to-protein ratio unknown). Used proteins were ovalbumin, saporin, diphtheria toxin, and an unspecific IgG. Purification is afforded by SEC HPLC. Analysis of dendrimer-to-protein ratio is performed by gel electrophoresis.

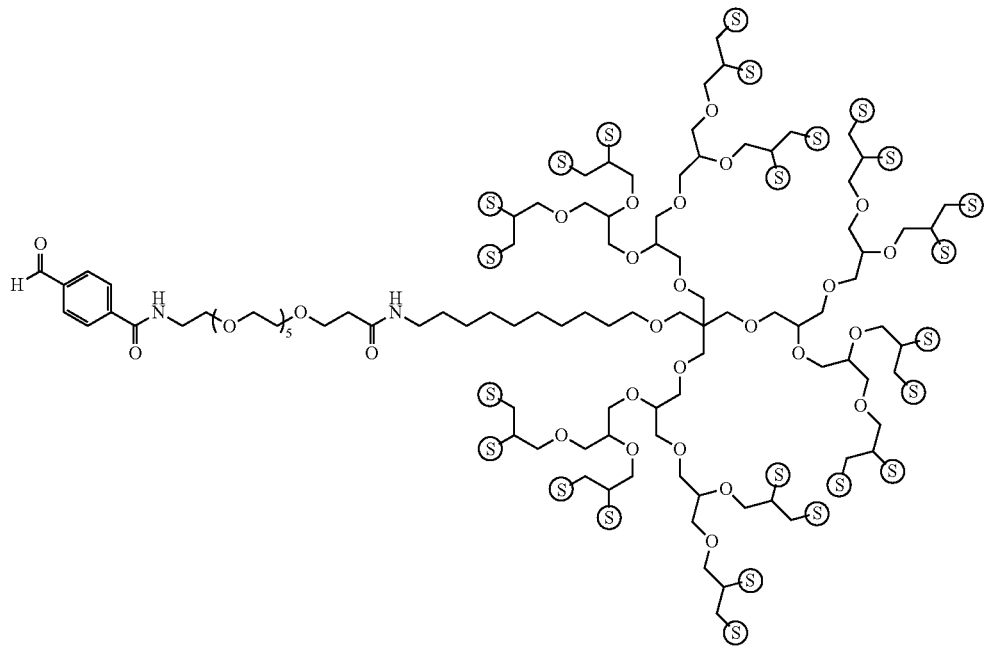

$S = OSO_3 \; Na^+$

Example 22

Conjugation of Sulfated Dendrimer to Proteins Via Acid-Cleavable Bond: Synthesis of Sulfated Dendrimer with Hydrazone Linker and Maleimido Group

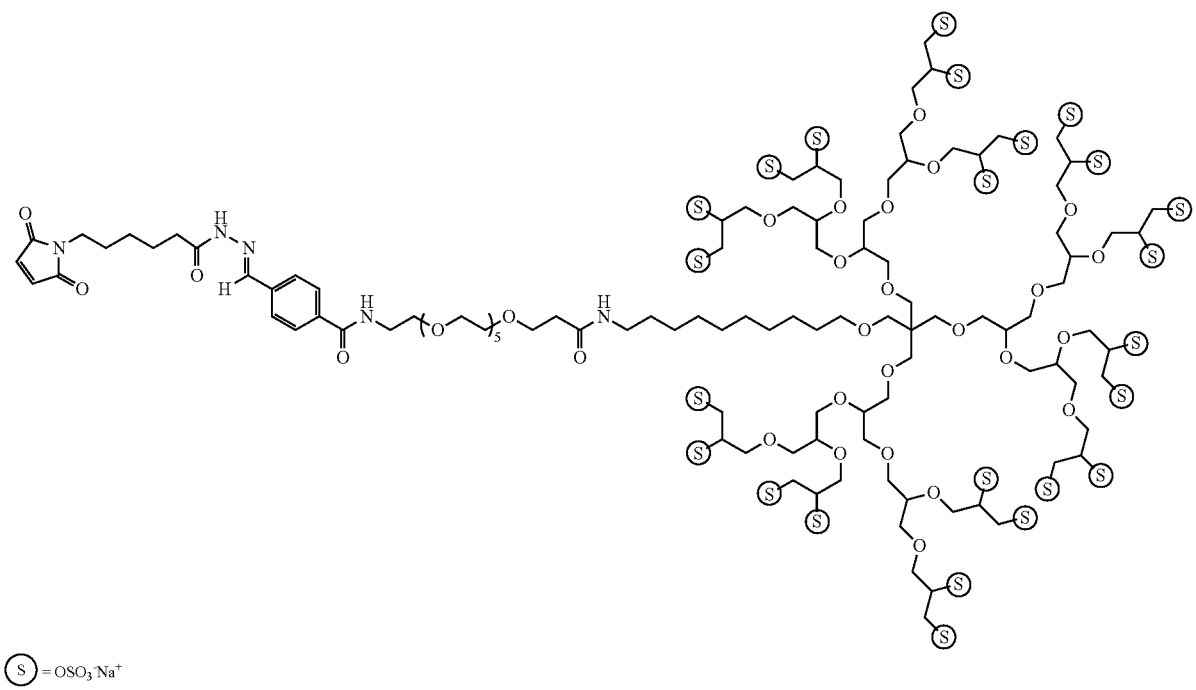

$\text{\textcircled{S}} = OSO_3^-Na^+$

Dendrimer d31 is fused with EMCH (ε-maleimidocaproic acid hydrazide) according to methods published (Walker G F et al., Molecular Therapy 2005, 11, 418-425).

These types of modification can be extended to other aromatic, aliphatic aldehyde moieties, as well as ketone moieties (such as 4-acetylbenzoic acid) yielding hydrazones, carboxyhydrazones, as well as imines.

What is claimed is:

1. A pharmaceutical composition, comprising a conjugate of the formula

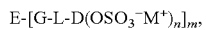

E-[G-L-D(OSO$_3^-$M$^+$)$_n$]$_m$, wherein E is a therapeutic or diagnostic effector molecule,
wherein D(OSO$_3^-$M$^+$)$_n$ is a dendrimer D carrying a number n of sulfate groups OSO$_3^-$M$^+$, wherein the number n of sulfate groups is selected from 6, 8, 12, 16, 18, 24, 30, 32, 36, 40, 48, 72 or 96,
wherein M is a cationic inorganic or organic counter ion to the anionic sulfate group,
wherein L is a linker or spacer between D and E,
wherein G is a connecting functional group forming the attachment between L and E, and wherein m is an integer from 1 to 20 and
wherein each of the dendrimers D of said conjugate has the same molecular weight and
wherein the number n of sulfate groups is the same for each dendrimer D,
wherein the linker L is covalently bound to a focal point of the dendrimer D at a position, whereby from this focal point, the dendrimer is grown to reach its dendritic structure
and wherein the dendrimers D(OSO$_3^-$M$^+$)$_n$ have the following relations between n and molecular weight, which are calculated for M$^+$ being a sodium ion:

| number of sulfates (n) | Molecular weight of D(OSO$_3^-$M$^+$)$_n$ not exceeding |
|---|---|
| 6 | 2000 Da |
| 8 | 2400 Da |
| 12 | 4000 Da |
| 16 | 5500 Da |
| 18 | 6000 Da |
| 24 | 8000 Da |
| 30 | 10000 Da |
| 32 | 11000 Da |
| 36 | 12000 Da |
| 40 | 13000 Da |
| 48 | 16000 Da |
| 72 | 24000 Da |
| 96 | 32000 Da. |

2. The pharmaceutical composition according to claim 1, wherein the repeating units of monomers to build the dendrimer D are selected from the group consisting of 1,2-substituted glycerol, 1,3-substituted glycerol, pentaerythritol, glucose, mannose, galactose, lysine, tris(hydroxymethyl)aminomethane, tris(propionic acid)aminomethane, 1,1'-bis(hydroxymethyl)-propionic acid, succinic acid, glutaric acid, maleic acid, glycolic acid, diglycolic acid, adipic acid, lactic acid, citric acid, propionic acid (2-aminoethyl)amide, propyleneimine, ethyleneimine, propyleneoxide, and ethyleneoxide.

3. The pharmaceutical composition according to claim 1, wherein the connection of said monomers in the dendrimer D is based on functional groups selected from ether, thioether, carboxylic ester, sulfonylester, sulfonamide, carboxylamide, amine, carbamate, thiocarbamate, urea, thiourea, hydrazone, imine, disulfide, phosphate, phosphonate, triazole, acetal, and ketal.

4. The pharmaceutical composition according to claim 1, wherein D contains terminal groups selected from 1,2-disulfatoalkyl, 1,3-disulfatoalkyl, 1,2,4-trisulfato-3-alkyl, N,N'-di(1-sulfatoalkyl)amine, tris(sulfatomethyl)methyl, and 1,2,3,4,5-pentasulfatoalkyl.

5. The pharmaceutical composition according to claim 1, wherein L is a C$_{4-100}$-alkyl group, selected from the group consisting of aliphatic cyclic, branched or linear units in which one or more methylene groups may independently be replaced by a unit selected from the group consisting of O, S, NH, NH—O, C(=O)NH, OC(=O)NH, OC(=O)O, NHC(=O)NH, NHC(=S)NH, C(=NH)NH, C(=O), S(=O)$_2$, S(=O), S(=O$_2$)O, S—S, CH=N, CH=N—NH, C=N—NHC(=O), OP(=O)(O$^-$M$^+$)O, P(=O)(O$^-$M$^+$)O, arylene, ethenylene or ethinylene, and triazolylene, in which any hydrogen atom may independently be replaced by methyl, ethyl or hydroxymethyl.

6. The pharmaceutical composition according to claim 1, wherein E is a therapeutic or diagnostic effector molecule.

7. The pharmaceutical composition according to claim 6, wherein the effector molecules are selected from the group consisting of small molecules with a molecular weight of approximately 600 to 2000 Da, peptides, proteins, glycans, and nucleic acids.

8. The pharmaceutical composition according to claim 6, wherein the effector molecule is a therapeutic effector molecule comprising substances which may interfere with intracellular mechanisms of proliferation, apoptosis, synthesis of connective tissue material (e.g. collagen, fibronectin), immune function, senescence, or immune defence.

9. The pharmaceutical composition according to claim 7, wherein the effector molecules are cytostatic agents.

10. The pharmaceutical composition according to claim 7, wherein the proteins are selected from the group consisting of globular proteins, glycoproteins, toxins, enzymes, antibodies, antibody fragments, engineered antibody and protein constructs, wherein said antibodies, antibody fragments, engineered antibody and protein constructs optionally comprise single domain antibodies (sdAb), single chain Fv antibodies (scFv), or single chain-Fv-Fc antibodies (scFv-Fc).

11. The pharmaceutical composition according to claim 6, wherein E is directed against molecules involved in proliferation and apoptosis of tumor cells.

12. The pharmaceutical composition according to claim 1, wherein G is a connecting functional group forming the covalent attachment between E and L, selected from the group consisting of O, S, NH, NH—O, C(=O)NH, OC(=O)NH, OC(=O)O, NHC(=O)NH, NHC(=S)NH, C(=NH)NH, C(=O), S(=O)$_2$, S(=O), S(=O$_2$)O, S—S, CH=N, CH=N—NH, C=N—NHC(=O), OP(=O)(O$^-$M$^+$)O, P(=O)(O$^-$M$^+$)O, arylene, ethenylene ethinylene, and triazolylene.

13. The pharmaceutical composition according to claim 1, for use (i) in treating a disease selected from the group comprising cancer, inflammation, autoimmune disease, metabolic disease and fibrosis, or (ii) in anti-proliferative, pro-proliferative, anti-apoptotic, pro-apoptotic, anti-fibrotic, pro-fibrotic, anti-lipogenic, anti-diabetic, immune-stimulatory and anti-aging treatment.

14. The pharmaceutical composition according to claim 1, wherein the conjugate is a defined dendrimer system of a single molecular weight.

15. The pharmaceutical composition according to claim 1, wherein $M^+$ is a sodium ion.

16. The pharmaceutical composition according to claim 7, wherein the effector molecules are peptide or peptidomimetic structures, wherein said peptide or peptidomimetic structures optionally comprise cyclic or open-chain peptides with natural or non-natural structural modifications.

17. The pharmaceutical composition according to claim 7, wherein the small molecules have a molecular weight of 600 to 2000 Da.

18. The pharmaceutical composition according to claim 1, wherein the effector molecule is a peptide which binds targets selected from the group consisting of p19INK4D, GSK-3, myc, INK4A, p53, KRas, NRas, Hras, p27, KIP1, GSK3 beta, HER4, Src, PTEN, Bcl-2, Bcl-xL, mcl-1 Ataxin-1, catenin, IRAK1, IRAK2, IRAK4, VEGFR1, ZAP70, Aurora A, Aurora B, and Aurora C.

19. The pharmaceutical composition according to claim 18, wherein the effector molecule is a peptide which binds targets selected from the group consisting of myc, Bcl-2, Bcl-xL, mcl-1, catenin, and p53.

20. The pharmaceutical composition according to claim 1, wherein the effector molecule is an alpha-helical peptide derived from apoptosis sensitizing proteins which is selected from the group consisting of BIM, BID, NOXA, and PUMA.

21. The pharmaceutical composition according to claim 1, wherein the effector molecule is a peptide selected from the group consisting of:

CGMRPEIWIAQELRRIGDEFNA;
CGDMRPEIYI(Aib)QELRRIGD(Aib)Y;
CGLSQEQLEHRERSLQTLRDIQRMLF;
CGLSKEQLEHRERSLQTLRDIERLL;
CGEEQWAREIGAQLRRMADDLNAQYER;
CGEDIIRNIARHAAQVGASADRSI; and
CPKWILKKATAYILSVQAEEQKL.

22. The pharmaceutical composition according to claim 1, wherein the effector molecule is a toxin polypeptide selected from the group consisting of diphtheria toxin, diphtheria toxin lacking receptor-binding activity, *pseudomonas* exotoxin A, truncated forms of *pseudomonas* exotoxin that lacks the receptor-binding domain Ia, ricin toxin, saporin, dianthin, gelonin, thricosanthin, pokeweed antiviral protein (PAP), bouganin, anthrax protective antigen, alpha toxin, abrin, and apoptosis-inducing polypeptides.

23. The pharmaceutical composition according to claim 1, wherein the effector molecule is a toxic polypeptide selected from the group consisting of desoxyribonuciease I (DNase I), desoxyribonuclease II (DNase II), polypeptides targeting alpha-tubulin, polypeptides targeting beta-tubulin, polypeptides targeting dynein, conjugates polypeptides targeting kinesin, polypeptides targeting $NEDD_1$, polypeptides targeting transforming acidic coiled-coil protein TACC, and polypeptides targeting colonic hepatic tumor overexpresses gene chTOG.

24. The pharmaceutical composition according to claim 1, wherein the effector molecule is bevacizumab or IgG.

25. The pharmaceutical composition according to claim 1, wherein the effector molecule is a protein selected from the group consisting of wild-type p53, wild-type p21, apoptosis-inducing factor 1 ($AIF_1$), $ASK_1$, apoptosis-inducing protein (AIP), caspase-2, caspase-3, caspase-6, caspase-7, caspase-8, caspase-9, caspase-10, Bax, serine protease, Smac, cytochrome c, Apaf-1, and apoptin.

* * * * *